United States Patent [19]
Shiojima et al.

[11] Patent Number: 6,066,316
[45] Date of Patent: May 23, 2000

[54] FINE DISPERSION COMPOSITION OF WAX, HAIR COSMETIC PREPARATION AND GLAZING AGENT

[75] Inventors: Yoshihiro Shiojima; Takayuki Omura; Yasunari Nakama; Fuminori Harusawa, all of Kanagawa, Japan

[73] Assignee: Shiseido Co., Ltd., Tokyo, Japan

[21] Appl. No.: 09/044,866

[22] Filed: Mar. 20, 1998

[30] Foreign Application Priority Data

Mar. 21, 1997 [JP] Japan ..................................... 9-087362
Sep. 30, 1997 [JP] Japan ..................................... 9-282833

[51] Int. Cl.$^7$ ..................................................... A61K 7/08
[52] U.S. Cl. .................. 424/70.19; 424/70.1; 424/70.21; 424/70.31; 424/401; 514/937; 514/938
[58] Field of Search ..................................... 424/401, 70.1, 424/70.19, 70.31, 70.21; 514/937, 938

[56] References Cited

U.S. PATENT DOCUMENTS 4,980,167  12/1990  Harashima .............................. 424/401
5,360,581  11/1994  Rizvi et al. .
5,641,480   6/1997  Vermeer .

FOREIGN PATENT DOCUMENTS 0 217 250 A2    4/1987   European Pat. Off. .
0 394 078      10/1990   European Pat. Off. .
0 408 174 A1    1/1991   European Pat. Off. .
0 446 094 A1    9/1991   European Pat. Off. .
2 666 015       8/1990   France .
04433597        3/1995   Germany .
3-2112          1/1991   Japan .
4-230616        8/1992   Japan .
5-220383        8/1993   Japan .
7-173025        7/1995   Japan .
2 269 384       2/1994   United Kingdom .

*Primary Examiner*—Thurman K. Page
*Assistant Examiner*—Brian K. Seidleck
*Attorney, Agent, or Firm*—Snider & Associates; Ronald R. Snider

[57] ABSTRACT

This invention is to provide a fine dispersion composition of wax which is stable in wide temperature range and is favorable in safety such as skin irritation, and is to provide a hair cosmetic preparation which is excellent in hair dressing power and has less stickiness and can give smoothness and easiness of combing to a hair, and to provide a glazing agent. A fine dispersion composition and a hair cosmetic preparation and a glazing agent comprising the same which comprises amphoteric surfactant and/or semi-polar surfactant, nonionic surfactant and wax, a hair cosmetic preparation which comprises said fine dispersion composition of wax and one or more of a specific effective ingredient, and a glazing agent which comprises said fine dispersion composition of wax.

24 Claims, 5 Drawing Sheets

FINE DISPERSION COMPOSITION OF WAX, HAIR COSMETIC PREPARATION AND GLAZING AGENT

RELATED APPLICATIONS

This application claims a priority of Japanese Patent Application No. 9-87362 filed Mar. 21, 1997 and Japanese Patent Application No. 9-282833 filed Sep. 30, 1997 which are incorporated herein by reference.

FIELD OF THE INVENTION

The present invention relates to a fine dispersion of wax which is excellent in stability and is favorable in safety (i.e., less skin irritation) in particular and relates to a hair cosmetic preparation comprising the same, an improvement of a feel of use, and a glazing agent.

DESCRIPTION OF THE PRIOR ART

Wax is an oily component which is solid or semisolid in ordinary temperature and is widely used in the field of cosmetic, glazing agent and paint, because its film has water repellency.

For example, some wax are used as a base in the case where these wax are used for a cosmetic. However, such cosmetic sometimes causes stickiness and glaringness in a coated portion. Accordingly, wax is largely used as various kinds of emulsions.

Japanese Unexamined Patent Publication No. Hei 3-2112, Japanese Unexamined Patent Publication No. Hei 4-230616, Japanese Unexamined Patent Publication No. Hei 5-220383, Japanese Unexamined Patent Publication No. Hei. 7-173025, and the like exists in conventional as for an art of fine dispersion of wax.

However, a fine dispersion was prepared by using nonionic, anionic, or cationic surfactant in these above-described arts. Though safety such as skin irritation was favorable in the case where only nonionic surfactant was used, stability with time was spoiled because HLB of system was changed with temperature.

Also, though stability with temperature was improved in the case where a fine dispersion was prepared with a combination of nonionic and anionic surfactant, only anionic surfactant or only cationic surfactant, a problem of safety such as skin irritation occurred.

In a conventional hair cosmetic preparation, the preparation used together with resin and an oily components such as silicone oil, high molecular silicone, ester oil, hydrocarbon oil, and the like which are solubilized, emulsified, and dissolved are largely used for the purpose of giving glossiness, smoothness and favorable hair set retention to a hair.

On the contrary, wax was sometimes compounded to a hair cosmetic preparation for purpose of giving hair dressing power. However wax was largely used as various kinds of emulsions, since such hair cosmetic preparation sometimes causes stickiness and glaringness in coated portion.

In view of the foregoing problems of the prior art, a first object of the present invention is to provide a fine dispersion composition of wax which is stable in wide temperature range and is favorable in safety such as skin irritation, and a hair cosmetic preparation and a glazing agent comprising the same.

A second object of the present invention is to provide a hair cosmetic preparation which has excellent hair dressing power and less stickiness and can give smoothness and easiness of combing to a hair.

SUMMARY OF THE INVENTION

As a result of diligent studies of the inventors for attaining the above-mentioned object, it has been found that a fine dispersion composition wax can be prepared by using nonionic surfactant together with amphoteric surfactant. Also, the inventors has found that said fine dispersion composition has high safety and has an excellent property in adjustment power in the case where said composition is particularly used as a hair cosmetic preparation. Also the inventors has found that said fine dispersion composition is excellent as a glazing agent.

Also, it has been found that a hair cosmetic preparation that a fine particle which is solid or semisolid in ordinary temperature in said fine dispersion composition of wax, and an oily particle comprising one or more of a hydrocarbon oil and/or an ester oil are separately dispersed in water is excellent in hair dressing power and has excellent property with respect to smoothness of hair, less stickiness, and easiness of combing.

Namely, a fine dispersion composition of wax in accordance with the present invention comprises an amphoteric surfactant and/or a semi-polar surfactant, a nonionic surfactant, and a wax.

Also, in said fine dispersion composition of wax, HLB of the total nonionic surfactant is preferably 6 to 15.

Also, in said fine dispersion composition of wax, a weight ratio of amphoteric surfactant/(amphoteric surfactant+ nonionic surfactant) is preferably 0.03 to 0.5.

Also, in said fine dispersion composition of wax, a weight ratio of amphoteric surfactant/(amphoteric surfactant+ nonionic surfactant) is preferably 0.04 to 0.17 in the case were HLB of the total nonionic surfactant is 12 to 15.

Also, in said fine dispersion composition of wax in accordance with the present invention, it is preferable that said composition comprises a polyoxyethylene polyoxypropylene alkyl ether as the nonionic surfactant.

Also, in said fine dispersion composition of wax, it is preferable that said polyoxypropylene alkyl ether is represented by the following formula

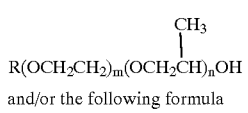

and/or the following formula

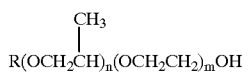

(wherein, R shows an alkyl group or an alkenyl group having a carbon number from 12 to 24, m is in the range of $5 \leq m \leq 30$, and n is in the range of $0 < n \leq 5$.).

Also, in said fine dispersion composition of wax which comprises said polyoxyethylene polyoxypropylene alkyl ether, it is preferable that a weighted average HLB of the whole nonionic surfactant is 5 to 15 in the formula which is formulated by Kawakami shown in the following.

(Formula of Kawakami)

$$HLB = 7 + 11.7 \log \frac{Mw}{Mo}$$

Mw ;Molecular weight of hydrophilic group portion of surfactant

Mo ;Molecular weight of lipophilic group portion of surfactant

Also, in said fine dispersion composition of wax which compounds said polyoxyethylene polyoxypropylene alkyl ether, a weight ratio of amphoteric surfactant/(amphoteric surfactant+nonionic surfactant) is 0.03 to 0.5.

Also, in said fine dispersion composition of wax in accordance with the present invention, said wax is an oily component which is solid or semisolid in ordinary temperature.

Also, in said fine dispersion composition of wax in accordance with the present invention, said composition can be obtained by cooling said system down to ordinary temperature after heating said system higher than the melting point of wax and within the solubilization critical temperature of system.

Also, in said fine dispersion composition of wax in accordance with the present invention can be prepared by using an emulsifier which has high shearing force under the condition which is higher than the melting point of said wax.

Also, a hair cosmetic preparation in accordance with the present invention comprises said fine dispersion composition of wax.

Also, a hair cosmetic preparation in accordance with the present invention, a fine particle which is comprised in said fine dispersion composition of wax, and an oily particle comprising one or more of a hydrocarbon oil and/or an ester oil are separately dispersed in water.

Also, a hair cosmetic preparation in accordance with the present invention, it is preferable that said hydrocarbon oil and/or said ester oil is liquid in ordinary temperature.

Also, a hair cosmetic preparation in accordance with the present invention, it is preferable that an amount of said hydrocarbon oil and/or ester oil is 1 to 50 wt % with respect to the whole amount of said composition.

Also, in a process for the preparation of said hair cosmetic preparation in accordance with the present invention, it is preferable to prepare by mixing said fine dispersion composition of wax and an emulsified composition of a hydrocarbon oil and/or an ester oil which are prepared in separately.

Also, in a process for the preparation of said hair cosmetic preparation in accordance with the present invention, it is preferable to compound a complex which is obtained by mixing an amphoteric surfactant and/or a semi-polar surfactant and higher fatty acid, as said emulsified composition.

Also, a glazing agent in accordance with the present invention comprises said fine dispersion composition of wax.

DETAILED DESCRIPTION

Figure 1:
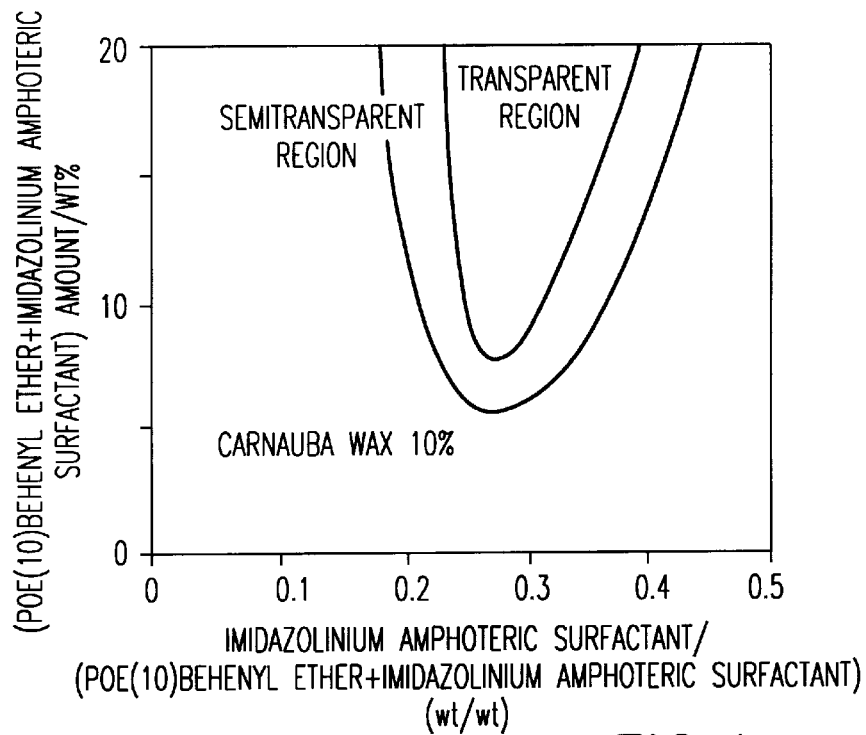
FIG. 1 is an explanatory view which shows the relation between a composition, an amount and a dispersion condition of surfactant in the case where nonionic surfactant of HLB 9 was used in the fine dispersion composition of the present invention.

In the following, an embodiment of the present invention will be explained in more detail.

The present invention is to provide a fine dispersion composition of wax which is excellent in stability and safety such as less skin irritation, a hair cosmetic which is favorable in feel of use and a glazing agent comprising the same.

The fine dispersion composition of wax and the hair cosmetic and the glazing agent were explained in separately.

Japanese Unexamined Patent Publication No. Hei 3-2112, Japanese Unexamined Patent Publication No. Hei 4-230616, Japanese Unexamined Patent Publication No. Hei 5-220383, Japanese Unexamined Patent Publication No. Hei 7-173025, and the like exists in conventional as for an art of fine dispersion of wax is cosmetic.

However, a fine dispersion was prepared by using nonionic, anionic, or cationic surfactant in these above-described arts. Though safety such as skin irritation was favorable in the case where only nonionic surfactant was used, stability with time was spoiled because HLB of system was changed with temperature.

Also, though stability with temperature was improved in the case where a fine dispersion was prepared with a combination of nonionic and anionic surfactant, only anionic surfactant or only cationic surfactant, a problem of safety such as skin irritation occurred.

The fine dispersion composition of wax described in the following is stable in wide temperature range and has less skin irritation. Various ingredients of the fine dispersion of wax are described in the following.

Solid Wax

Wax in the present invention means an oily component which is solid in ordinary temperature. For example, beeswax, candelilla wax, cotton wax, carnauba wax, bayberry wax, Chinese wax, spermaceti, montan wax, rice bran wax, lanolin, kapok wax, Japan wax, lanolin acetate, liquid lanolin, sugar cane wax, lanolin fatty acid isopropyl ester, hexyl laurate, lanolin hydrogenated, jojoba wax, hard lanolin, shellac wax, microcrystalline wax, paraffin wax, POE lanolin alcohol ether, POE lanolin alcohol acetate, POE cholesteryl ether, lanolin fatty acid polyethyleneglycol, fatty acid glycerides, hydrogenated castor oil, petrolatum, POE hydrogenated lanolin alcohol ether, and the like can be listed.

These wax can be used by mixing each other. Also, these wax can be used within the range that is solid in ordinary temperature, even when wax is mixed with other solid or liquid oily component.

As for these oily components, the following components can be listed.

As an examples of liquid fats and oils, avocado oil, camellia oil, turtle oil, macadamia nut oil, corn oil, mink oil, olive oil, rape seed oil, egg yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, chinese-wood oil, japanese-wood oil, jojoba oil, germ oil, triglycerol, glyceryl trioctanoate, pentaerythritol tetraoctanote, glyceryl triisopalmitate, and the like can be listed.

As an examples of solid fats and oils, cacao butter, coconut oil, hydrogenated coconut oil, palm oil, palm kernel oil, japanese wax kernel oil, hydrogenated oil, and the like can be listed.

As an examples of hydrocarbon oils, liquid petrolatum, ozokerite, squalene, pristane, paraffin, squalane, and the like can be listed.

Nonionic Surfactant

A nonionic surfactant is necessary in the present invention, and HLB of the nonionic surfactant is preferably 6 to 15, and more preferably 7 to 14.

As an examples of such nonionic surfactants: POE sorbitan fatty acid esters such as POE sorbitan monooleate, POE sorbitan monostearate, POE sorbitan tetraolelate, and the like; POE sorbitol fatty acid esters such as POE sorbitol monolaurate, POE sorbitol monooleate, POE sorbitol pentaoleate, POE sorbitol monosterate, and the like; POE glyceryl fatty acid esters such as POE glyceryl monostearate, POE glyceryl monoisostearate, POE glyceryl triisostearate, and the like; POE fatty acid esters such as POE monooleate, POE distearate, POE dioleate, ethyleneglycol distearate, and the like; POE alkyl ethers such as POE lauryl ether, POE oleyl ether, POE stearyl ether, POE behenyl ether, POE octyldodecyl ether, POE cholestanol ether, and the like; POE alkyl phenyl ethers such as POE octylphenyl ether, POE nonylphenyl ether, POE dinonylphenyl ether, and the like; pluronic surfactants such as pluronic and the like; tetra POE/tetra POP ethylene diamine condensates such as tetronic, and the like; POE beeswax/lanolin derivatives such as POE castor oil, POE hydrogenated castor oil, POE hydrogenated castor oil monoisostearate, POE hydrogenated castor oil triisostearate, POE hydrogenated castor oil monopyroglutamate monoisostearate, POE hydrogenated castor oil maleate, and the like; alkanolamide surfactants such as coconut fatty acid diethanolamide, lauric acid monoethanolamide, fatty acid isopropanolamide, and the like; POE propylene glycol fatty acid ester; POE alklamine; POE fatty acid amide; sucrose fatty acid ester; POE nonyl phenyl formaldehyde condensate; alkyl ethoxy dimethylamine oxide; trioleyl phosphate; and the like can be listed.

Also, it is preferable to use polyoxyethylene polyoxypropylene alkyl ether as the nonionic surfactant. Because, a prepared fine dispersion composition of wax s excellent in stability with time and is improved the change of external appearance (deterioration of transparency) due to aggregation of fine particle with time passage and creaming of dispersion article, in the case where polyoxyethylene polyoxypropylene alkyl ether is compared with polyoxyethylene alkyl ether which has the same oxyethylene chain length.

As an examples of the above-mentioned polyoxyethylene polyoxypropylene alkyl ethers, the polyoxyethylene polyoxypropylene alkyl ether which is represented by $$R(OCH_2CH_2)_m(OCH_2\overset{\underset{\displaystyle CH_3}{|}}{C}H)_nOH$$

and/or $$R(OCH_2\overset{\underset{\displaystyle CH_3}{|}}{C}H)_n(OCH_2CH_2)_mOH$$

(wherein, R shows an alkyl group or an alkenyl group having a carbon number from 12 to 24, m is in the range of $5 \leq m \leq 30$, and n is in the range of $0 < n \leq 5$.), is preferable.

Also, a weighted average HLB of total nonionic surfactant is preferably 5 to 15 in the formula which is formulated by Kawakami shown in the following, in the case where polyoxyethylene polyoxypropylene alkyl ether is used.

(Formula of Kawakami)

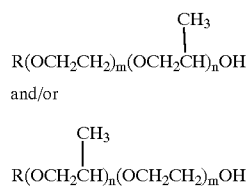

Mw ;Molecular weight of hydrophilic group portion of surfactant

Mo ;Molecular weight of lipophilic group portion of surfactant

As for an examples of such polyoxyethylene polyoxypropylene alkyl ether, POE/POP cetyl ether, POE/POP behenyl ether, POE/POP decyl tetradecyl ether, POE/POP monobutyl ether, POE/POP hydrogenated lanolin, POE/POP glyceryl ether, and the like that the values of m and n are within the range as shown above.

Amphoteric Surfactant and Semi-Polar Surfactant

As an examples of an amphoteric surfactant in the present invention, the surfactants shown in the following Formula (I) to (V) are exemplifed. Also, as an examples of a semi-polar surfactant in the present invention, the surfactant shown in the following Formula (VI) is exemplified.

Amide betaine amphoteric surfactants represented by Formula (I)

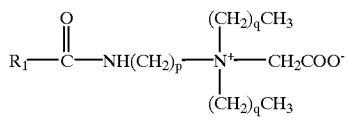

(Rebon 2000 (manufactured by Sanyo Chemical Industries Ltd.), Anon BDF (manufactured by NOF Corp.), and the like can be listed as a commercially available goods.).

Amide sulfobetaine amphoteric surfactants represented by Formula (II)

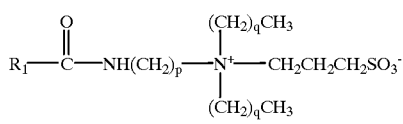

(Lonzaine CS (manufactured by Lonza Inc.), Mirataine CBS (manufactured by Miranol Inc.), and the like can be listed as a commercially available goods.).

Betaine amphoteric surfactants represented by Formula (III)

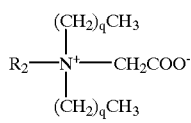

(Anon BL (manufactured by NOF Corp.), Dehyton AB-30 (manufactured by Henkel Corp.,), and the like can be listed as a commercially available goods.).

Sulfobetaine amphoteric surfactants represented by Formula (IV):

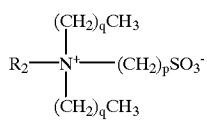

(Lonzaine 12CS (manufactured by Lonza Inc.), and the like can be listed as a commercially available goods.).

Imidazolinium amphoteric surfactant represented by Formula (V):

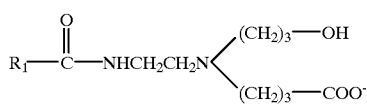

(Ovazoline 662-N (manufactured by Toho Chemical Industry Co., Ltd.), Anon GLM (manufactured by NOF Corp.), and the like can be listed as a commercially available goods.).

Tertiary amine oxide semi-polar surfactant represented by Formula (VI):

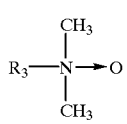

(Unisafe A-LM (manufactured by NOF Corp.), Wondamine OX-100 (manufactured by Shin-nihon co., ltd)), and the like can be listed as a commercially available goods.).

In Formula (I) to (VI), $R_1$ is preferably an alkyl group or an alkenyl group having average number of carbon atoms from 9 to 21, and more preferably an alkyl group or an alkenyl group having average number of carbon atoms from 11 to 17. Most preferably, $R_1$ is an alkyl group or an alkenyl group having average number of carbon atoms from 11 to 13. Hydrophilicity is too strong in the case where average number of carbon atoms is less than 9. On the other hand, solubility for water is deteriorated in the case where average number of carbon atoms is more than 21.

$R_2$ and $R_3$ shows an alkyl group or an alkenyl group having average number of carbon atoms from 10 to 18.

p, q, and s shows an integer from 2 to 4, an integer from 0 to 3, and an integer 1 or 2, respectively.

Among these amphoteric and/or semi-polar surfactants, one or more of selected from these surfactants is used in the present invention.

Water Dispersion Medium

In the present invention, a fine wax particle is preferable to be dispersed in a water dispersion medium. As an examples of the water dispersion medium, only water or water and ethanol, glycerin, polyethyene glycol, propylene glycol, dipropylene glycol, 1,3-butanediol, xylitol sorbitol, maltitol, chondroitin sulfate, hyaluronic acid, mucoitin sulfuric acid, caronin acid, soluble collagen, cholesteryl-12-hydroxystearate, sodium lactate, bile salt, dl-pyrrolidonecarboxylate, short-chain soluble collagen, diglycerine (EO) PO adducts, rosa roxburgii extract, yarrow extract, sweet clover extract, and the like can be listed.

Preparation of Fine Dispersion

First, the present inventors conducted the tests shown in the following and tried preparing a fine dispersion composition of wax.

TABLE 1

| Test Examples | 1 | 2 | 3 | 4 | 5 | 6 | 7 | 8 | 9 |
|---|---|---|---|---|---|---|---|---|---|
| Cationic surfactant Stearyldimethyl benzyl ammonium chloride | 15 | — | — | — | 5 | — | — | 10 | — |
| Anionic surfactant Sodium lauryl sulfite | — | 15 | — | — | — | 5 | — | — | 10 |
| Nonionic surfactant POE (10) behenyl ether | — | — | 15 | — | 10 | 10 | 10 | — | — |
| Amphoteric surfactant Lauryl dimethylamino acetic acid betaine | — | — | — | 15 | — | — | 5 | 5 | 5 |
| Wax Candelilla wax | 10 | 10 | 10 | 10 | 10 | 10 | 10 | 10 | 10 |
| Ion-exchanged water | 75 | 75 | 75 | 75 | 75 | 75 | 75 | 75 | 75 |
| External appearance | Cloudy | Cloudy | Cloudy | Cloudy | Cloudy | Cloudy | Transparent | Cloudy | Cloudy |

<Manufacturing Process>

Nonionic surfactant and amphoteric surfactant were dissolved into ion-exchanged water and the mixture was heated up to 80 to 90° C. Then, candelilla wax was added to the mixture and stirred with a propeller stirrer for 1 hour. A composition was obtained by cooling down the mixture with ice.

<Result>

As is clear from TABLE 1, each emulsified compositions had a tendency to became cloudy and its stability was not favorable in the case where cationic, anionic, nonionic, and amphoteric surfactant were used in separately (Test Examples 1 to 4). Also, the tendency to becoming cloudy and instability was the same as in the case where cationic or anionic surfactant and nonionic surfactant were combined (Test Examples 5 and 6) or where cationic or anionic surfactant and amphoteric surfactant were combined (Test Examples 8 and 9).

However, external appearance of the emulsified composition became transparent in the case where nonionic surfactant and amphoteric surfactant were combined (Test Example 7). Accordingly, this indicates that a fine dispersion composition of wax was obtained.

As a result of the measurement by dynamic light scattering method, a particle diameters of this fine dispersion composition was about 30 nm.

Study of Nonionic Surfactant

Next, the present inventors studied about optimum HLB of nonionic surfactant.

Namely, the following composition was used as basic prescription. Emulsification conditions were studied with changing HLB of nonionic surfactants.

<Basic Prescription 1>

| Candelilla wax | 10% |
|---|---|
| Amide betaine amphoteric surfactant | 5% |
| Nonionic surfactant | 10% |
| Ion-exchanged water | Balance |
| Total | 100% |

(Compounding weight ratio of amphoteric surfactant/(amphoteric surfactant+nonionic surfactant)=about 0.33)

<Basic Prescription 2>

| Candelilla wax | 10% |
|---|---|
| Amide betaine amphoteric surfactant | 1.5% |
| Nonionic surfactant | 13.5% |
| Ion-exchanged water | Balance |
| Total | 100% |

(Compounding weight ratio of amphoteric surfactant/(amphoteric surfactant+nonionic surfactant)=about 0.1)

These results are shown in TABLE 2.

TABLE 2

| Composition of Surfactant | | HLB | Emulsification Condition | Basic Prescription |
|---|---|---|---|---|
| POE (5) behenyl ether | 10% | 5 | Separation | 1 |
| POE (3) stearyl ether | 6% | 6 | Creamlike | 1 |
| POE (10) behenyl ether | 4% | | | |
| POE (3) stearyl ether | 4% | 7 | A semitransparent liquid phase | 1 |
| POE (10) behenyl ether | 6% | | | |
| POE (3) stearyl ether | 2% | 8 | A transparent liquid phase | 1 |
| POE (10) behenyl ether | 8% | | | |
| POE (10) behenyl ether | 10% | 9 | A transparent liquid phase | 1 |
| POE (10) behenyl ether | 9.25% | 10 | A transparent liquid phase | 1 |
| POE (50) lauryl ether | 0.75% | | | |
| POE (10) behenyl ether | 8.25% | 11 | A semitransparent liquid phase | 1 |
| POE (50) lauryl ether | 1.75% | | | |
| POE (15) oleyl ether | 13.5% | 12 | A transparent liquid phase | 2 |
| POE (20) behenyl ether | 13.5% | 13 | A transparent liquid phase | 2 |
| POE (20) behenyl ether | 6.75% | 14 | A semitransparent liquid phase | 2 |
| POE (30) behenyl ether | 6.75% | | | |
| POE (30) behenyl ether | 13.5% | 15 | Creamlike | 2 |

As is clear from TABLE 2, a uniform emulsion system could be formed in the case where HLB of nonionic surfactant was 6 to 15 in the condition that a weight ratio of amphoteric surfactant/(amphoteric surfactant+nonionic surfactant) was about 0.33 or 0.1. In particular, a semitransparent or transparent liquid phase could be formed in the case where HLB of nonionic surfactant was 7 to 14.

Accordingly, in the fine dispersion composition of wax in accordance with the present invention, HLB of nonionic surfactant is preferably 6 to 15, and more preferably 7 to 14 so as to obtain a transparent or transparent system.

Next, the present inventors studied about the types and dispersion condition of nonionic surfactants. The results in the composition of Basic Prescription 1 will be shown in the following.

TABLE 3

| HLB: | 5 | 6 | 7 | 8 | 9 | 10 | 11 |
|---|---|---|---|---|---|---|---|
| POE straight chain fatty acid | | | | | | | |
| C12 (Lauryl) | | Δ n = 3 | | | ○ n = 5 | ○ n = 7 | |
| C16 (Cetyl) | | | Δ n = 5 | | ○ n = 7 | | ○ n = 9 |
| C18 (Stearyl) | | | | Δ n = 6 | | ○ n = 8 | Δ n = 10 |
| C18 (Oleyl) | | | | Δ n = 6 | ○ n = 8 | Δ n = 10 | |
| C20 (Arachyl) | × n = 3 | | | | | ○ n = 10 | |
| C22 (Behenyl) | × n = 5 | | | | | ○ n = 10 | |
| POE branched chain fatty acid | | | | | | | |
| C18 (Isostearyl) | | | Δ n = 5 | | | ○ n = 10 | |
| C20 (Octyldodecyl) | | | | | | ○ n = 10 | |
| C24 (Decyltetradecyl) | | | | | Δ n = 10 | | ○ n = 15 |

(n: POE addition number of moles)

In TABLE 3, ○ means the condition that is formed a transparent liquid phase. Δ and × represents the conditions of semitransparent or creamlike and separation, respectively.

As is clear from TABLE 3, in the condition that Basic Prescription 1, i.e., the weight ratio of amphoteric surfactant/ (amphoteric surfactant+nonionic surfactant) was about 0.33, a transparent liquid phase could be formed when HLB of nonionic surfactant was about 9 to 11, in the case where various nonionic surfactants were separately used.

Next, as to the types and dispersion conditions of nonionic surfactants, the results in the composition of Basic Prescription 2 will be shown in the following.

TABLE 4

| HLB: | 12 | 13 | 14 | 15 |
|---|---|---|---|---|
| POE straight chain fatty acid | | | | |
| C12 (Lauryl) | | ○ n = 15 | | |
| C16 (Cetyl) | | | | |
| C18 (Stearyl) | | ○ n = 15 | Δ n = 20 | |
| C18 (Oleyl) | | ○ n = 15 | | |
| C20 (Arachyl) | | | ○ n = 18 | |
| C22 (Behenyl) | | | ○ n = 20 | Δ n = 30 |
| POE branched fatty acid | | | | |
| C18 (Isostearyl) | | ○ n = 15 | | |
| C20 (Octyldodecyl) | | ○ n = 16 | ○ n = 20 | |
| C24 (Decyltetradecyl) | | | ○ n = 20 | Δ n = 15 |

(n: POE addition number of moles)

In TABLE 4, ○ means the condition that is formed a transparent liquid phase. Δ and × represents the conditions of semitransparent or creamlike and separation, respectively.

As is clear from TABLE 4, in the condition that Basic Prescription 2, i.e., the weight ratio of amphoteric surfactant/ (amphoteric surfactant+nonionic surfactant) was about 0.1, a transparent liquid phase could be formed when HLB of nonionic surfactant was about 12 to 13, in the case where various nonionic surfactants were separately used.

Accordingly, in summing up TABLE 3 and 4, though the optimum HLB value of nonionic surfactant is different according to the weight ratio of surfactant, the optimum HLB value is about 6 to 15.

Also, in consideration of TABLE 2, two or more nonionic surfactants can be used with combining. HLB value in this case depends on a weighted average.

Further, the present inventors studied about POE cholesteryl, POE glyceryl, POE hydrogenated castor oil, and the like. However, it was difficult to prepare a transparent liquid phase in the case where these multi chain nonionic surfactants were used separately. As a matter of course, even in these multi chain nonionic surfactants, it is possible to obtain a preferable dispersion system by combining with the other nonionic surfactant. In particular POE straight or branched chain fatty chain acid ether can be used in favorable.

Correlation between Amphoteric Surfactant and Nonionic Surfactant

Next, the present inventors studied about correlation between amphoteric surfactant and nonionic surfactant.

Namely, wax dispersion system was prepared with changing a compounding ratio and an amount of amide betaine amphoteric surfactant (Trade name Rebon 2000SF) and nonionic surfactant (POE (10) behenyl ether) according to Basic Prescription 3 shown in the following.

| <Basic Prescription 3> | |
|---|---|
| Carnauba wax | 10% |
| Amide betaine amphoteric surfactant | X% |
| Nonionic surfactant | Y% |
| Ion-exchanged water | Balance |
| Total | 100% |

These results are shown in FIG. 1.

As is clear from FIG. 1, an extremely favorable ratio of surfactant=amphoteric surfactant/(amphoteric surfactant+ nonionic surfactant) existed in the vicinity of 0.3, in the case where POE (10) behenyl ether of HLB 9 was used as the nonionic surfactant. However, the range of its ratio had a tendency to broaden with an increase of the amount of (amphoteric surfactant+nonionic surfactant).

The preferable ratios of surfactants are different according to the change of HLB value of nonionic surfactants as a matter of course. Then, the results which was POE (20) behenyl ether of HLB 13 as the nonionic surfactant with the same composition as like FIG. 1 are shown in FIG. 2.

Figure 2:
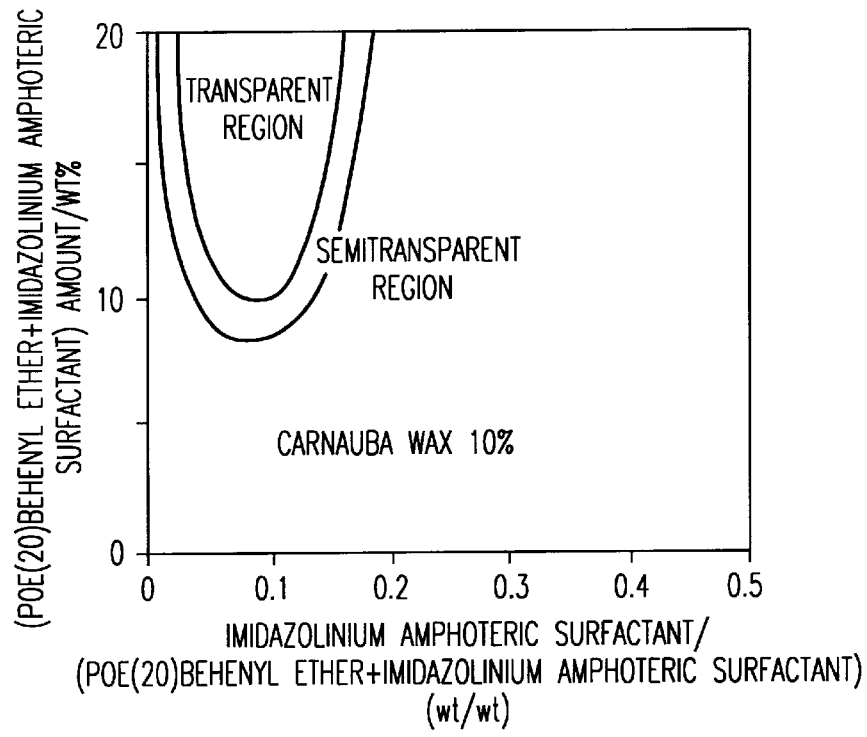
FIG. 2 is an explanatory view which shows the relation between a composition, an amount and a dispersion condition of surfactant in the case where nonionic surfactant of HLB 13 was used in the present invention.

As is clear from FIG. 2, an extremely favorable ratio of surfactant=amphoteric surfactant/(amphoteric surfactant+ nonionic surfactant) existed in the vicinity of 0.1, in the case where POE (20) behenyl ether of HLB 13 was used as the nonionic surfactant. However, the range of the preferable ratio was about 0.04 to 0.17.

Figure 3:
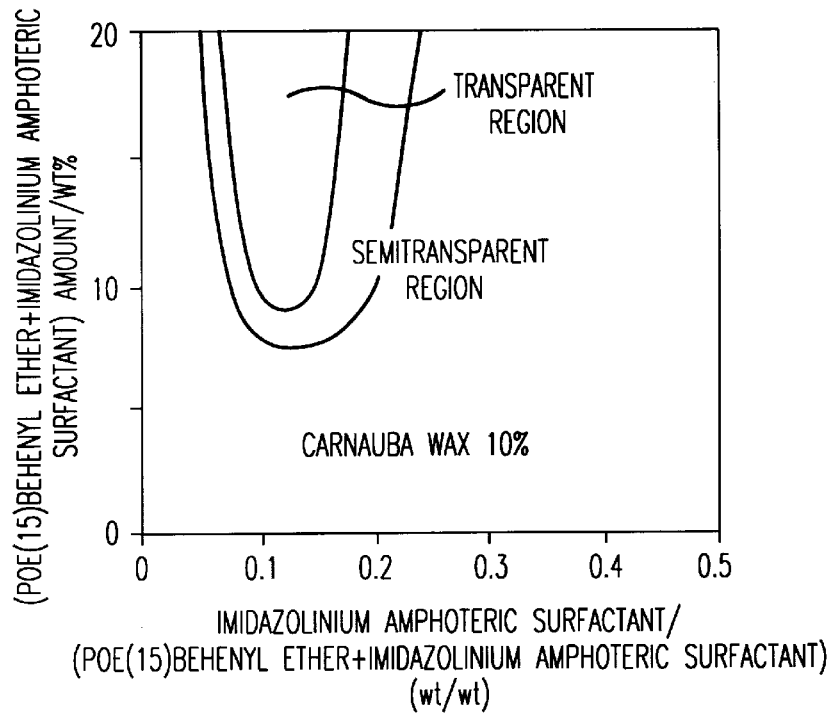
FIG. 3 is an explanatory view which shows the relation between a composition, ab amount and a dispersion condition of surfactant in the case where nonionic surfactant of HLB 12 was used in the fine dispersion composition of the present invention.
Figure 4:
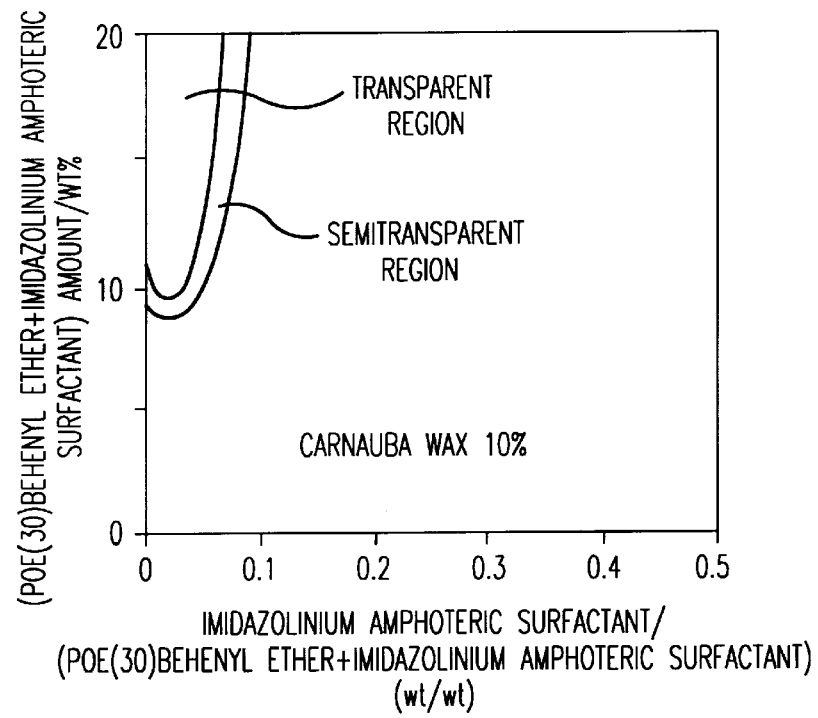
FIG. 4 is an explanatory view which shows the relation between a composition, an amount and a dispersion condition of surfactant in the case where nonionic surfactant of HLB 15 was used in the fine dispersion composition of the present invention.

Also, the results in the cases where POE (15) behenyl ether of HLB 12 and POE (30) behenyl ether of HLB 15 were used as the nonionic surfactant are shown in FIG. 3 and FIG. 4, respectively.

As is clear from the above-mentioned results, though a favorable ratios of surfactant=amphoteric surfactant/

(amphoteric surfactant+nonionic surfactant) are different according to HLB of the nonionic surfactant, the favorable ratios of surfactant is preferably about 0.03 to 0.5. In the case where the ratio of the surfactant is less than 0.03, temperature stability is spoiled since contribution of nonionic surfactant to system is enlarged. On the contrary, a fine dispersion composition of wax is difficult to obtain in the case where the ratio of surfactant is more than 0.5.

Next, the present inventors studied about safety and stability.

Safety

Safety was evaluated from ovalbumin degenerating rate.

<Testing method>

Safety was measured by using 220 nm absorption peak of ovalbumin degenerating rate in the case where a sample was added to ovalbumin pH buffering solvent so as that a concentration of the sample could be 1%, with using a water HPLC.

$$\{(Ho-Hs)/Ho\} \times 100$$

Ho: Highness of 220 nm absorption peak of ovalbumin

Hs: Evaluation of highness of 220 nm absorption peak in the case where the sample was added to ovalbumin buffering solvent was conducted according to the following evaluation standard.

⊚—Little skin irritation—less than 30% of ovalbumin degenerating rate

○—A little skin irritation—30% or more and less than 60% of ovalbumin degenerating rate Δ—Moderate skin irritation—60% or more and less than 80% of ovalbumin degenerating rate x—Strong skin irritation—80% or more of ovalbumin degenerating rate The results are shown in TABLE 5.

TABLE 5

| Surfactant | Evaluation |
| --- | --- |
| Sodium dodecyl sulfate (Anionic) | Δ |
| Lauryldimethyl ammonium chloride (Cationic) | x |
| POE (20) behenyl ether (Nonionic) | ⊚ |
| Regbon 2000SF (Amphoteric) | ○ |
| Sodium dodecyl sulfate + POE (20) behenyl ether (1:1) | ○ |
| Rebon 2000SF + POE (20) behenyl ether (1:1) | ⊚ |

(Rebon 2000SF; manufactured by Sanyo Chemical Industries Ltd., aminobetaine amphoteric surfactant)

As a result, skin irritation of a combination of the amphoteric surfactant and the nonionic surfactant is the same level with that of the nonionic surfactant and has high safety. Accordingly, a fine dispersion composition of wax which use together with the amphoteric surfactant has high safety.

Stability

A fine dispersion composition of wax was prepared according to Basic Prescription 4 shown in the following. Stability with time in the condition at 50° C. and after 1 week of the composition was evaluated. These results are shown in TABLE 6.

| <Basic Prescription 4> | |
| --- | --- |
| Candelilla wax | 10% |
| Surfactant | about 10 to 20% |
| Ion exchanged water | Balance |

TABLE 6

| | Prescription | | | | | |
| --- | --- | --- | --- | --- | --- | --- |
| | 1 | 2 | 3 | 4 | 5 | 6 |
| Candelilla wax | 10 | 10 | 10 | 10 | 10 | 10 |
| POE (3) stearyl ether | 5 | — | — | 7 | 10 | — |
| POE (10) behenyl ether | — | 10 | 15 | — | — | 6.5 |
| POE (20) behenyl ether | — | 1 | — | — | — | — |
| POE (40) hydrogenated castor oil | 10 | — | — | 10 | 6 | — |
| Rebon 2000SF (significant part about 30%) | — | — | 1 | — | — | 10 |
| Sofdazoline LHL-SF (significant part about 30%) | — | — | — | 1 | 10 | — |
| Ion-exchanged water | Balance | Balance | Balance | Balance | Balance | Balance |
| Weight ratio of surfactant Amphoteric/ (Amphoteric + Nonionic) | — | — | 0.020 | 0.017 | 0.16 | 0.32 |
| Stability (50° C., 1 week) | Separated | Separated | Separated | Separated | Not changed | Not changed |

(Sofdazoline LHL-SF; manufactured by Kawaken Fine Chemicals Co., Ltd., Imidazolinium amphoteric surfactant)

As is clear from TABLE 6, stability with time was spoiled in the cases where nonionic surfactant only was used and the weight ratio of surfactant (prescribed in above) was less than 0.03.

on the contrary, stability was favorable in the cases where amphoteric surfactant and nonionic surfactant was combined with a favorable surfactant ratio.

Next, the present inventors studied about polyoxyethylene polyoxypropylene alkyl ether as a nonionic surfactant.

Preparation of Fine Dispersion

First, the present inventors conducted the tests shown in the following and tried preparing a fine dispersion composition of wax.

TABLE 7

| Test Examples | 10 | 11 | 12 | 13 | 14 | 15 | 16 | 17 | 18 |
|---|---|---|---|---|---|---|---|---|---|
| Cationic surfactant Stearyldimethyl benzyl ammonium chloride | 15 | — | — | — | 5 | — | — | 10 | — |
| Anionic surfactant Sodium lauryl sulfate | — | 15 | — | — | — | 5 | — | — | 10 |
| Nonionic surfactant POE (10) POP (1) behenyl ether | — | — | 15 | — | 10 | 10 | 10 | — | — |
| Amphoteric surfactant Lauryl dimethylamino-acetic acid betaine | — | — | — | 15 | — | — | 5 | 5 | 5 |
| Wax Candelilla wax | 10 | 10 | 10 | 10 | 10 | 10 | 10 | 10 | 10 |
| Ion-exchanged water | 75 | 75 | 75 | 75 | 75 | 75 | 75 | 75 | 75 |
| External appearance | Cloudy | Cloudy | Cloudy | Cloudy | Cloudy | Cloudy | Transparent | Cloudy | Cloudy |

<Manufacturing Process>

Nonionic surfactant and amphoteric surfactant were dissolved into ion-exchanged water and the mixture was heated up to 80 to 90° C. Then, candelilla wax was added to the mixture and stirred with a propeller stirrer for 1 hour. A composition was obtained by cooling down the mixture with ice.

<Result>

As is clear from TABLE 7, each emulsified compositions had a tendency to became cloudy and its stability was not favorable in the case where cationic, anionic, nonionic, and amphoteric surfactant were used in separately (Test Examples 10 to 13). Also, the tendency to becoming cloudy and instability was the same as in the case where cationic or anionic surfactant and nonionic surfactant were combined (Test Examples 14 and 15) or where cationic or anionic surfactant and amphoteric surfactant were combined (Test Examples 17 and 18).

However, external appearance of the emulsified composition became transparent in the case where nonionic surfactant and amphoteric surfactant were combined (Test Example 16). Accordingly, this indicates that a fine dispersion composition of wax was obtained.

As a result of the measurement by dynamic light scattering method, a particle diameters of this fine dispersion composition was about 30 nm.

Study of Nonionic Surfactant

Next, the present invention studies about optimum HLB of nonionic surfactant.

Namely, the following composition was used as basic prescription. Emulsification conditions were studies with changing HLB of nonionic surfactants.

| <Basic Preparation 5> | |
|---|---|
| Carnauba wax | 10% |
| Amide betaine amphoteric surfactant | 6% |
| Nonionic surfactant | 9% |
| Ion-exchanged water | Balance |
| Total | 100% |

(Compounding weight ratio of amphoteric surfactant/(amphoteric surfactant+nonionic surfactant)=about 0.4)

| <Basic Prescription 6> | |
|---|---|
| Carnauba wax | 10% |
| Amide betaine amphoteric surfactant | 5% |
| Nonionic surfactant | 10% |
| Ion-exchanged water | Balance |
| Total | 100% |

(Compounding weight ratio of amphoteric surfactant/(amphoteric surfactant+nonionic surfactant)=0.33)

| <Basic Prescription 7> | |
|---|---|
| Carnauba wax | 10% |
| Amide betaine amphoteric surtactant | 1.5% |
| Nonionic surfactant | 13.5% |
| Ion-exchanged water | Balance |
| Total | 100% |

(Compound weight ratio of amphoteric surfactant/(amphoteric surfactant+nonionic surfactant)=about 0.1)

| <Basic Prescription 8> | |
|---|---|
| Carnauba wax | 10% |
| Amide betaine amphoteric surfactant | 0.75% |
| Nonionic surfactant | 14.25% |
| Ion-exchanged water | Balance |
| Total | 100% |

(Compounding weight ratio of amphoteric surfactant/(amphoteric surfactant+nonionic surfactant)=0.05)

These results are shown in TABLE 8.

TABLE 8

| Composition of Surfactant | HLB | Emulsification Condition | Basic Prescription |
|---|---|---|---|
| POE (7) POP (4) behenyl ether | 4 | Separation | 5 |
| POE (7) POP (2) behenyl ether | 5 | Creamlike | 5 |

TABLE 8-continued

| Composition of Surfactant | HLB | Emulsification Condition | Basic Prescription |
|---|---|---|---|
| POE (7) POP (1) behenyl ether | 6 | A semitransparent liquid phase | 5 |
| POE (10) POP (2) behenyl ether | 7 | A transparent liquid phase | 6 |
| POE (10) POP (1) behenyl ether | 8 | A transparent liquid phase | 6 |
| POE (15) POP (2) behenyl ether | 9 | A transparent liquid phase | 7 |
| POE (15) POP (1) behenyl ether | 10 | A transparent liquid phase | 7 |
| POE (20) POP (2) behenyl ether | 11 | A transparent liquid phase | 7 |
| POE (20) POP (1) behenyl ether | 12 | A transparent liquid phase | 7 |
| POE (30) POP (2) behenyl ether | 13 | A transparent liquid phase | 8 |
| POE (30) POP (1) behenyl ether | 14 | A transparent liquid phase | 8 |
| POE (30) POP (1) stearyl ether | 15 | Creamlike | 8 |
| POE (30) POP (1) lauryl ether | 16 | Separation | 8 |

As is clear from TABLE 8, a uniform emulsion system could be formed in the case where HLB of nonionic surfactant was 5 to 15 in the condition that a weight ratio of amphoteric surfactant/(amphoteric surfactant+nonionic surfactant) was about 0.05 or 0.04. In particular, a semitransparent or transparent liquid phase could be formed in the case where HLB of nonionic surfactant was 6 to 14.

Accordingly, in the fine dispersion composition of wax in accordance with the present invention, HLB of nonionic surfactant is preferably 5 to 15, and more preferably 6 to 14 so as to obtain a transparent or transparent system.

Further, the present inventors studied about POE cholesteryl, POE glyceryl, POE hydrogenated caster oil, and the like. However, it was difficult to prepare a transparent liquid phase in the case where these multi chain nonionic surfactants were used separately. As a matter of course, even in these multi chain nonionic surfactants, it is possible to obtain a preferable dispersion system by combining with the other nonionic surfactant. In particular, POE straight or branched chain fatty acid ether can be used in favorable.

Correlation between Amphoteric Surfactant and Nonionic Surfactant

Next, the present inventors studied about correlation between amphoteric surfactant and nonionic surfactant.

Namely, wax dispersion system was prepared with changing a compounding ratio and an amount of amide betaine amphoteric surfactant (Trade name Rebon 2000SF) and nonionic surfactant (POE (10) POP (1) behenyl ether) according to the Basic Prescription shown in the following.

| <Basic Prescription 9> | |
|---|---|
| Carnauba wax | 10% |
| Amide betaine amphoteric surfactant | X% |
| Nonionic surfactant | Y% |
| Ion-exchanged water | Balance |
| Total | 100% |

Figure 5:
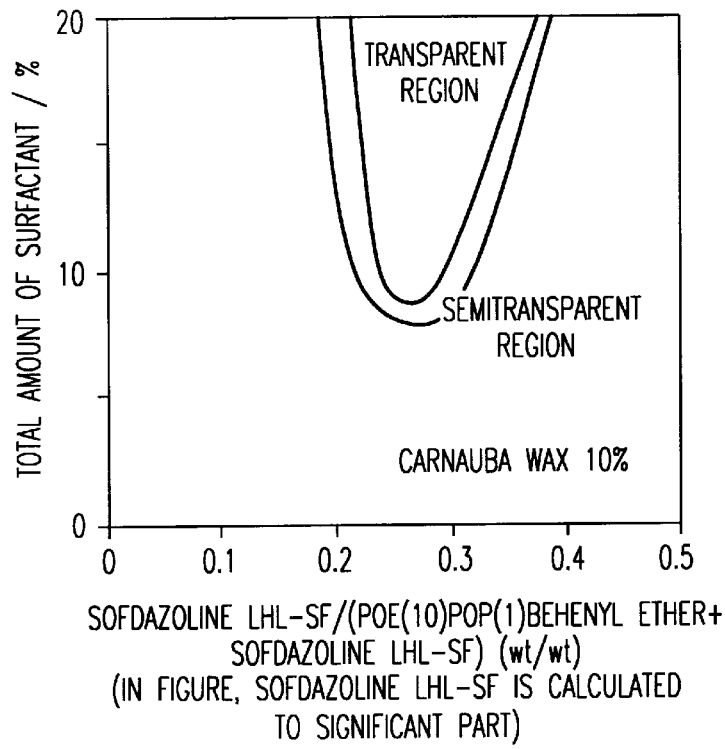
FIG. 5 is an explanatory view which shows the relation between a composition, an amount and a dispersion condition of surfactant in the case where nonionic surfactant of HLB 8 (polyoxyethylene polyoxypropylene alkyl ether) was used in the fine dispersion composition of the present invention.

These results are shown in FIG. 5.

As is clear from FIG. 5, an extremely favorable ratio of surfactant=amphoteric surfactant/(amphoteric surfactant+nonionic surfactant) existed in the vicinity of 0.3, in the case where POE (10) POP (1) behenyl ether of HLB 8 was used as the nonionic surfactant. However, the range of its ratio had a tendency to broaden with an increase of the amount of (amphoteric surfactant+nonionic surfactant).

The preferable ratios of surfactants are different according to the change of HLB value of nonionic surfactants as a matter of course. Then, the results which used POE (7) POP (1) behenyl ether of HLB 6 as the nonionic surfactant with the same composition as like FIG. 5 are shown in FIG. 6.

Figure 6:
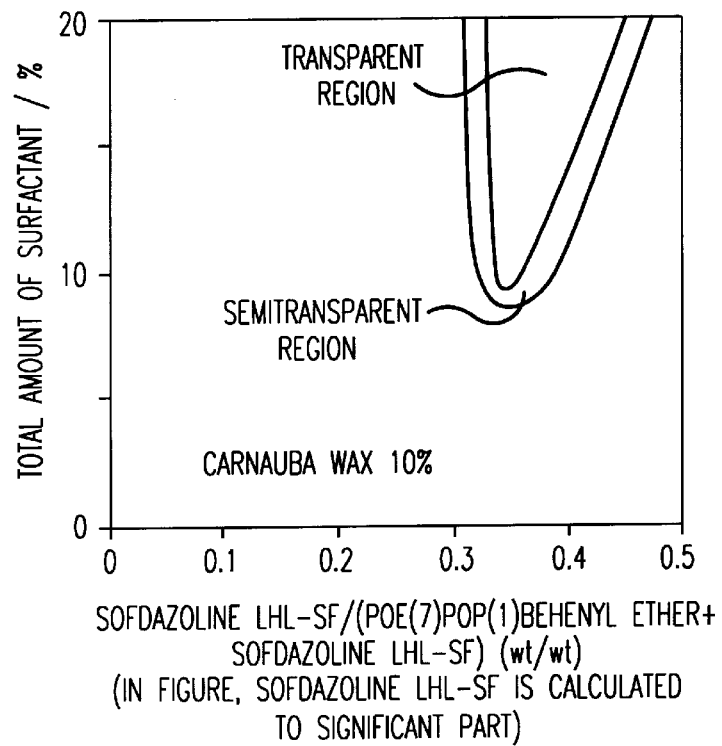
FIG. 6 is an explanatory view which shows the relation between a composition, an amount and a dispersion condition of surfactant in the case where nonionic surfactant of HLB 6 (polyoxyethylene polyoxypropylene alkyl ether) was used in the fine dispersion composition of the present invention.

As is clear from FIG. 6, an extremely favorable ratio of surfactant=amphoteric surfactant/(amphoteric surfactant+nonionic surfactant) existed in the vicinity of 0.35, in the case where POE (7) POP (1) behenyl ether of HLB 6 was used as the nonionic surfactant. However, the range of the preferable ratio was about 0.25 to 0.45.

Figure 7:
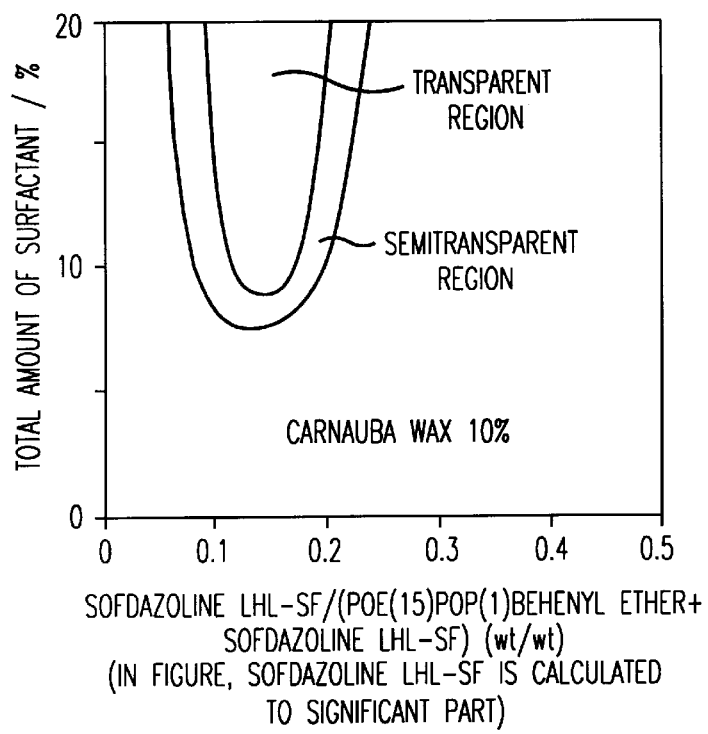
FIG. 7 is an explanatory view which shows the relation between a composition, an amount and a dispersion condition of surfactant in the case where nonionic surfactant of HLB 10 (polyoxyethylene polyoxypropylene alkyl ether) was used in the fine dispersion composition of the present invention.

Also, the results which used POE (15) POP (1) behenyl ether of HLB 10 as the nonionic surfactant with the same composition as like FIG. 5 are shown in FIG. 7.

As clear from FIG. 7, an extremely favorable ratio of surfactant=amphoteric surfactant/(amphoteric surfactant+nonionic surfactant) existed in the vicinity of 0.13, in the case where POE (15) POP (1) behenyl ether of HLB 10 was used as the nonionic surfactant. However, the range of the preferable ratio was about 0.05 to 0.25.

Figure 8:
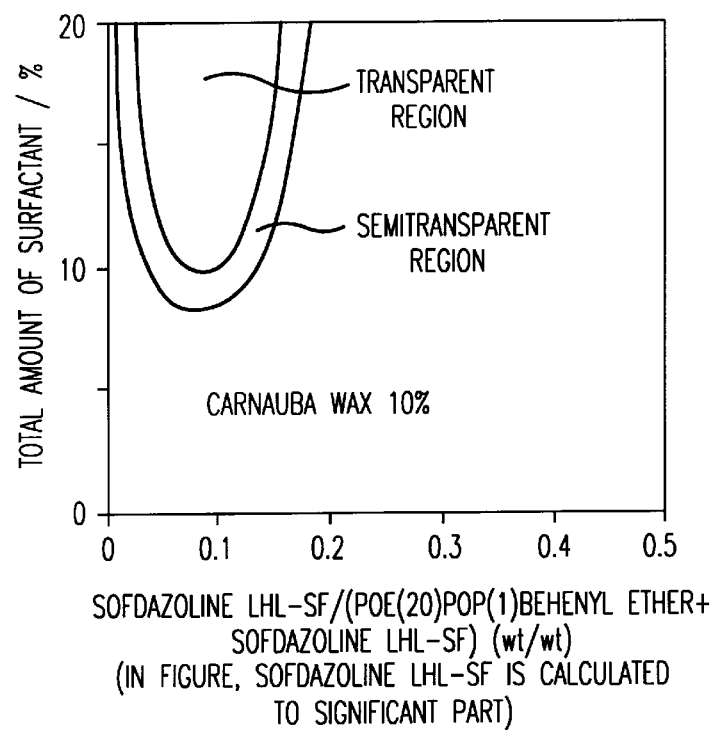
FIG. 8 is an explanatory view which shows the relation between a composition, an amount and a dispersion condition of surfactant in the case where nonionic surfactant of HLB 12 (polyoxyethylene polyoxypropylene alkyl ether) was used in the fine dispersion composition of the present invention.
Figure 9:
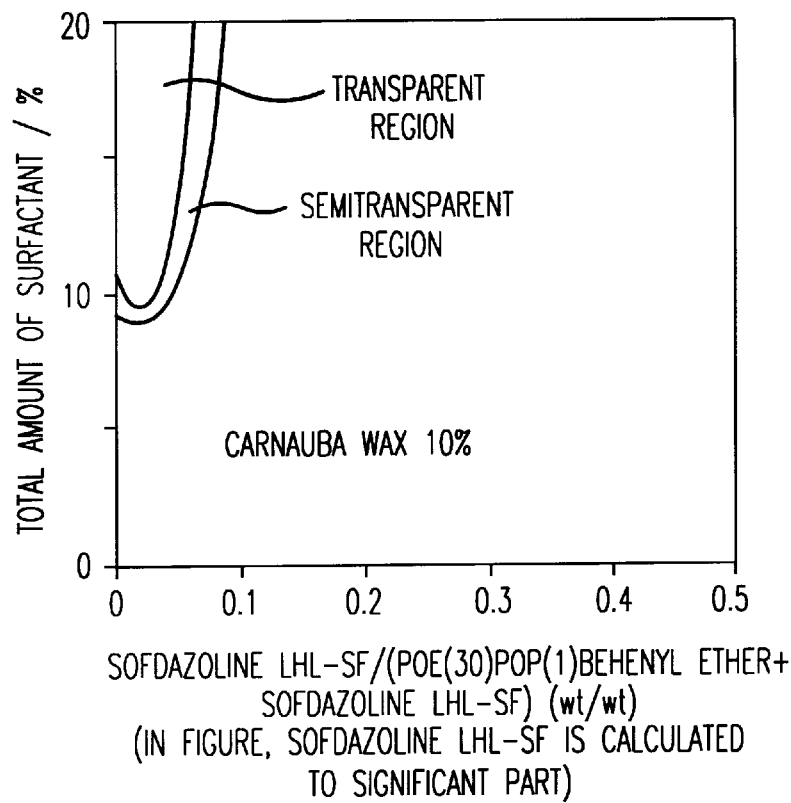
FIG. 9 is an explanatory view which shows the relation between a composition, an amount and a dispersion condition of surfactant in the case where nonionic surfactant of HLB 14 (polyoxyethylene polyoxypropylene alkyl ether) was used in the fine dispersion composition of the present invention.

Also, the results in the cases where POE (20) POP (1) behenyl ether of HLB 12 and POE (30) POP (1) behenyl ether of HLB 14 were used as the nonionic surfactant are shown in FIG. 8 and FIG. 9, respectively.

As is clear from the above-mentioned results, though a favorable ratios of surfactant=amphoteric surfactant/(amphoteric surfactant+nonionic surfactant) are different according to HLB of the nonionic surfactant, the favorable ratios of surfactant is preferably about 0.03 to 0.5. In the case where the ratio of the surfactant is less than 0.03, temperature stability is spoiled since contribution of nonionic surfactant to system is enlarged. On the contrary, a fine dispersion composition of wax is difficult to obtain in the case where the ratio of surfactant is more than 0.5.

Next, the present inventors studied about safety and stability.

Safety

Safety was evaluated from ovalbumin degenerating rate. Testing method and evaluation were described in above.

The results are shown in TABLE 9.

TABLE 9

| Surfactant | Evaluation |
|---|---|
| Sodium dodecyl sulfate (Anionic) | Δ |
| Lauryldimethyl ammonium chloride (Cationic) | x |
| POE (20) POP (1) behenyl ether (Nonionic) | ⊚ |
| Rebon 2000SF (Amphoteric) | ○ |
| Sodium dodecyl sulfate + POE (20) POP (1) behenyl ether (1:1) | ○ |
| Rebon 2000SF + POE (20) POP (1) behenyl ether (1:1) | ⊚ |

(Rebon 2000SF ; manufactured by Sanyo Chemical Industries Ltd., aminobetaine amphoteric surfactant)

As a result, skin irritation of a combination of the amphoteric surfactant and the nonionic surfactant is the same level with that of the nonionic surfactant and has high safety. Accordingly, a fine dispersion composition of wax which use together with the amphoteric surfactant has high safety.

Stability

A fine dispersion composition of wax was prepared according to Basic Prescription 10 shown in the following. Stability with time in the condition at 50° C. and after 1 week of the composition was evaluated. These results are shown in TABLE 10.

<Basic Prescription 10>

| | |
|---|---|
| Carnauba wax | 10% |
| Surfactant | about 15% |
| Ion-exchanged water | Balance |

TABLE 10

| | Prescription | | | | | |
|---|---|---|---|---|---|---|
| | 7 | 8 | 9 | 10 | 11 | 12 |
| Carnauba wax | 10 | 10 | 10 | 10 | 10 | 10 |
| POE (15) POP (1) stearyl ether | 5 | — | — | 4.85 | 13.5 | — |
| POE (10) POP (1) behenyl ether | — | 10 | 14.7 | — | — | 10.5 |
| POE (20) POP (1) behenyl ether | — | 5 | — | — | — | — |
| POE (40) POP (1) hydrogenated castor oil | 10 | — | — | 10 | — | — |
| Rebon 2000SF (significant part about 30%) | — | — | 1 | — | — | 15 |
| Sofdazoline LHL-SF (significant part about 30%) | — | — | — | 0.5 | 5 | — |
| Ion-exchanged water | Balance | Balance | Balance | Balance | Balance | Balance |
| Weight ratio of surfactant Amphoteric/ (Amphoteric + Nonionic) | — | — | 0.020 | 0.010 | 0.15 | 0.30 |
| Stability (50° C., 1 week) | Separated | Separated | Separated | Separated | Not changed | Not changed |

(Sofdazoline LHL-SF ; manufactured by Kawaken Fine Chemicals Co., Ltd., Imidazolinium amphoteric surfactant)

As is clear from TABLE 10, stability with time was spoiled in the cases where nonionic surfactant only was used and the weight ratio of surfactant (prescribed in above) was less than 0.03.

On the contrary, stability was favorable in the cases where amphoteric surfactant and nonionic surfactant was combined with a favorable surfactant ratio.

Preparation of Fine Dispersion Composition of Wax

A fine dispersion composition of wax of the present invention can be obtained by a preparation of microemulsion. As an example of the preparation of microemulsion, Japanese Patent Publication No. Hei 6-61454 and Japanese Patent Publication No. Hei 6-57316 are listed. An oily ultrafine particle of liquid is prepared by these techniques described in said publications. However, ultrafine particle of solid wax as like the present invention also can be prepared by using these techniques.

Namely, said fine dispersion composition of the present invention can be prepared by cooling down the system after heating the system higher than the melting point of the wax and within the stabilization critical temperature of the system.

A fine dispersion composition of wax of the present invention can be prepared by using an emulsifier which can give a strong shearing force such as a high-pressure homogenizer or mechanical force such as an ultrasonic emulsifier. It is preferable to emulsify the composition under the conditions over 400 atm, and more preferably, under the conditions over 600 atm and lower than 50° C.

<Hair Cosmetic Preparation>

A hair cosmetic preparation of the present invention can be used with favorable feel of use by adding the specific ingredients listed following to said fine dispersion composition of wax. As for (E)polyether compound that propylene oxide and/or ethylene oxide is additionally polymerized to the nucleus of polyhydric alcohol, (A)hydrocarbon oil and/or ester oil, (G)silicone derivative, and (I)water-soluble thickening agent, an oil-in-water emulsified composition which comprises these components were separately prepared as an emulsion part. The composition was obtained by mixing said fine dispersion composition of wax (wax part) with this emulsion part.

Emulsified Composition Comprising the Specific Ingredients (Emulsion Part)

Said oil-in-water emulsified composition can be used the composition which was prepared by ordinary method. Also, in considering skin irritation as like a fine dispersion composition of wax, a complex which can be obtained by mixing amphoteric surfactant and/or semi-polar surfactant and higher fatty acid as shown in Japanese Unexamined Patent Publication No. Hei-6-65596, can be used. However, stability of the emulsified composition after mixing was hardly influenced by the compounding ration of both ingredients.

Complex Obtained by Mixing Amphoteric Surfactant and/or Semi-polar Surfactant and Higher Fatty Acid Among the complex which are obtained by mixing the amphoteric surfactant and/or the semi-polar surfactant and the higher fatty acid used in the emulsion part of the present invention, the surfactants used for said fine dispersion composition of wax described above are used as an examples of the amphoteric surfactant and/or the semi-polar surfactant.

Higher Fatty Acid

As an examples of a higher fatty acid of the complex which is obtained by mixing the amphoteric surfactant and/or the semi-polar surfactant and the higher fatty acid which can be used in the emulsion part of the present invention, myristic acid, palmitic acid, stearic acid, behenic acid, oleic acid, 12-hydroxystearic acid, undecylenic acid, tall oil, isostearic acid, linoleic acid, linolenic acid, eicosapentaenoic acid (EPA), docosahexaenoic acid (DHA), and the like can be listed.

In addition to the specific ingredients described in the following, the hair cosmetic preparation of the present invention can use together the oily components which are compounded to a cosmetic preparation in general, the other surfactants, setting agent resin, viscosity modifier, pharmaceutical agent, antiseptic, UV-absorber, and the like within the quantitative and the qualitative range that the effects of the present invention are not spoiled, according to the object.

Next, various specific ingredients which are compounded for improving the feel of use in the case where the fine dispersion composition of the present invention is used in the hair cosmetic preparation.

(A)Hydrocarbon Oil and/or Ester Oil

As an examples of a hydrocarbon oil and/or ester oils used in the present invention, the component listed in the following are exemplified. For example, liquid petrolatum, isoparaffin, squalane, squalene, diisobutyl adipate, diisopropyl adipate, di (2-hexyldecyl) adipate, di(2-heptyl undecyl) adipate, isostearyl isostearate, isopropyl isostearate, ethyl isostearate, 2-octyldodecyl isostearate, butyl isostearate, hexyl isostearate, 2-hexyldecyl isostearate, isodecyl isononanoate, octyl isopalmitate, isostearyl 2-ethyl hexanoate, stearyl 2-ethyl hexanoate, cetyl 2-ethyl hexanoate, cetostearyl 2-ethyl hexanoate, hexadecyl 2-ethylhexanoate, octyldodecyl octanoate, 2-octyldodecanol, oleyl alcohol, isodecyl oleate, ethyl oleate, oleyl oleate, decyl oleate, cetyl caprate, monoglyceryl caprate, di (2-ethylhexyl) succinate, octyl salicylate, myristyl salicylate, octyldodecyl dimethyloctanoate, isocetyl stearate, ethyl stearate, octyl stearate, diisopropyl dimerate, pentaerythritol tetraisostearate, pentaerythritol tetra-2-ethylhexanoate, glyceryl triisostearate, 1,1,1-trimethylolpropane triisostearate, caprylic/capric acid triglyceride, isostearyl palmitate, isopropyl palmitate, octyl palmitate, 2-hexyldecyl palmitate, isostearyl hydroxystearate, isocetyl hydroxystearate, 2-ethylhexyl hydroxystearate, octyldodecyl hydroxystearate isostearyl pivalate, isodecyl pivalate, methyl castor oil fatty acid, arachyl propionate, 2-hexyldecanol, 2-hexyldecanoic acid, jojoba oil, isostearyl myristate, isocetyl myristate, isotridecyl myristate, isopropyl myristate, 2-octyldodecyl myristate, decyl myristate, butyl myristate, mink oil, ethyl mustelate, isostearyl laurate, hexyl laurate, and the like are listed.

An amount of said hydrocarbon oil and/or ester oil is 0.1 to 50 wt %, and more preferably 3 to 40 wt %. An excellent effects of the present invention such as less stickness of hand and smoothness of hair can not be obtained in the case where the amount of silylated peptide is less than 0.1 wt %. Also, in the case where the amount is more than 50 wt %, an improvement of feel of use was rarely observed.

Also, the weight ratio of wax/(hydrocarbon oil and/or ester oil) is preferably 0.1 to 10. An excellent feel of use of the present invention is spoiled in the case where the weight ratio is not within this range.

(B)Phospholipid, Protein or Protein Hydrolyzate and Derivatives Thereof

As an examples of the phospholipid used in the present invention, for example, phosphatidylcholine, phosphatidylinositol, phosphatidlethanlamine, phosphatidylserine, sphingomyelin, and the like, egg yolk lecithin, soybean lecithin extracted from egg yolk and soybean, products and hydrolyzates thereof. Also, as for the synthetic phospholipid. dialloylphosphatidylcholine, dipalmitoyl phosphatidylcholine and the like are listed.

Also, an examples of the protein or protein hydrolyzate and the derivatives thereof, for example, collagen, collagen, hydrolyzate, cationic collagen hydrolyzate, cocyl-hydrolyzed animal protein, keratin, elastin, elastin hyddrolyzate, casein, casein hydrolyzate, gelatin, gelatin hydrolyzate, soybean protein, wheat protein, glutelin, whey powder, fibroin, glucagon, egg white, egg white (nonthermal coagulation), egg white lysozyme, albumin fibrinogen, hemoglobin, globulin, and the hydrolyzate thereof are listed.

Either phospholipids or proteins may be used singly. However, it is preferable to compound both ingredients, i.e., one or more of phospholipid and one or more of protein or protein hydrolyzate and the derivatives of protein, in view of the repairing effect to a hair.

An amount of the phospholipid and/or proteins is 0.001 to 5 wt %, and more preferably 0.03 to 3 wt % with respect to the whole amount of the hair cosmetic preparation. The effect by compounding of phospholipid or proteins, i.e., less stickness and smoothness of hair cannot be obtained in the case where the amount is less than 0.001 wt %. On the contrary, in the case where the amount is more than 5 wt %, it is difficult to compound in solubility and bad odor is occurred.

(C)Keration Decomposition Derivatives

A keratin decomposition derivatives used in the present invention is manufactured by hydrolyzing keratin or by making alkali salt after oxidative destruction keratin. The keratin decomposition derivatives used in the present invention is also manufactured by the process in the following. After reduction destruction keratin, its derivative is made by chemical modifying of thiol group. Then, alkali salt is prepared.

As an examples of keratin, for example, animal hair, hair, feather, nail, horn, hoof, scale, and the like are listed. Among these, sheep wool, hair and feather are preferable in particular. These keratin can be used directly to oxidizing or reducing reaction. Also, these keratin can be conducted a pretreatment such as cutting or grinding to proper size, washing, degreasing and the like, as occasion demands.

Decomposition of keratin is conducted by one of these processes shown in the following.

(1)Hydrolyzing Reaction

① Hydrolysis by Acid

As an examples of acid, an inorganic acids such as hydrochloric acid, sulfuric acid, phosphoric acid, nitric acid, hydrogen bromide, and the like, and an organic acids such as formic acid, oxalic acid, and the like. These acids can be used with 3 to 85% concentration in general. However, it is desirable that the hydrolysis is always reacted under pH 4. Reaction temperature is preferably 40 to 100° C. and can be risen up to 160° C. under pressure. Reaction time is preferably 2 to 24 hours. A reactor which is neutralized with alkali such as sodium hydroxide, sodium carbonate, ammonium and the like, can be used directly. Further, the reactor can be used by purifying the reaction product by gel filtration, ion-exchanged resin, and the like.

Thus obtained acid hydrolyzate can obtain favorable result as compared with the alkali hydrolyzate, since polypeptide chain of keratin is not changed, excluding hydrolyzing, in the acid hydrolyzing.

② Hydrolysis by Alkali

As an examples of alkali, an inorganic alkalis such as sodium hydroxide potassium hydroxide, lithium hydroxide, barium hydroxide, sodium carbonate, potassium carbonate, lithium carbonate, sodium silicate, borax, and the like can be used. These alkalis are suitable within the concentration 1 to 20% in general. It is not preferable to use alkali more than need, since color phase of hydrolyzate solution becomes brown to black. Reaction is preferably conducted under the temperature within room temperature to 100° C. and for 30 minutes to 24 hours. It is necessary not to rise the temperature more than need and not to extend the reaction time. Hydrolysis by alkali has a advantage that the progress condition of the reaction is visible, since hydrolyzate of keratin are dissolved with the progress of reaction. Reaction is ended at the time that reaction mixture becomes uniform solution.

③ Hydrolyzing by Enzyme

As for enzyme, acidic proteases such as pepsin, protease A, protease B and the like, and neutral proteases such as papain, bromelain, thermolysin, trypsin, pronase, chymotrypsin, and the like are used. It is desirable that the pH value at hydrolyzing is adjusted within pH from 1 to 3 in the case where acidic protease such as pepsin is used and within pH from 5 to 8 in the case where neutral protease such as papain is used. It is convenient that the pH value is suitably adjusted by a buffering solution such as ammonium acetate/ammonia buffering solution, phosphoric acid buffering solution, and the like in general. Desirable reaction temperature is 30 to 45° C. and suitable reaction time is 3 to 24 hours, in general.

A molecular weight of the hydrolyzate is largely influenced by a using amount of enzyme, reaction temperature, and reaction time in hydrolyzing reaction by enzyme. Accordingly, it is necessary to determine the optimum condition about the using amount of enzyme, reaction temperature and reaction time with experimentally by examining a molecular-weight distribution of the obtained hydrolyzate by gel filtration technique.

The hydrolyzate by enzyme is preferable for compounding to a cosmetic, since hydrolyzate by enzyme has narrow molecular-weight distribution and is rarely form a free amino acid as compared with the hydrolyzate by acid and alkali.

It is desirable that an average molecular weight of the hydrolyzate which is obtained by the above-mentioned hydrolyzing reaction is 200 or more and 5000 or less. Because, adsorptivity of the keratin decomposition to a hair is determined by its molecular weight. The keratin decomposition which has about 1000 molecular weight are most ready to adsorb to a hair, and the keratin decomposition which has more than 5000 molecular weight are rarely adsorb to a hair. Also, it is preferable that as much as possible of many disulfide bond in keratin decomposition derivatives are existed. It is necessary to use the keratin which has high purity and to conduct hydrolyzing reaction under mold conditions.

(2) Oxidative decomposition reaction

Oxidation of keratin is conducted by the various known methods (N. H. Leon; Textile Progress, Volume 7, Page 1 (1975)). As for an oxidizer, organic or inorganic oxidizers which can electrophilically functions to disulfide bond (S—S bond, mentioned in the following) of keratin construction are preferable. For example, organic acid peroxide, inorganic peroxytho acid or its salt, permanganic acid or its salt, chromic acid or its related compounds, halogen, peroxide, oxyacid or its salt, and the like are exemplified. Among these oxidizers, peracetic acid, performic acid, and perbenzoic acid are preferable in particular.

Oxidizing reaction is conducted in liquid solvent by using excess amount of the oxidizer to the S—S bonds in the keratin, i.e., twice or more equivalent weight of the oxidizer, and more preferably 4 to 10 times equivalent weight of the oxidizer with respect to 1 of the S—S bond, in general. Though reaction can be done either the conditions of acidity or alkalinity, it is preferable to react under acidic condition, and in particular, to react under weak acidic condition. The conditions such as reaction temperature and pressure are different according to the kinds of the oxidizer and keratin which are used, and are not limited in particular. Though reaction temperature is sufficient with room temperature in general, the temperature can be risen as occasion demands. Also, though pressure is enough with normal pressure, the reaction can be conducted under reduced pressure or pressurization.

Thus, S—S bonds of the keratin are cloven and sulfonic acid (—$SOH_3$) is formed.

(3) Reducing Decomposition and Chemical Modifying Reaction

As for a reducing agents used for reducing the keratin, a reducing agent which gives thiol group (—SH) by cleaving S—S bonds in its structure or an organic or inorganic reducing agent which nucleophilically functions to S—S bond are preferable in general.

As an examples of the reducing agents, organic reducing agents such as mercaptoethanol, thioglycolic acid, benzyl mercaptan, 1,4-dithiothreitol, tributyl-phosphine, and the like, and inorganic reducing agents such as sulfides, e.g., sodium hydrogen sulfite, and the like, and metal hydrides e.g., lithium aluminium hydride are listed.

An amount of the reducing agent is used twice to 10 times equivalent to S—S bonds in the keratin, in general. The pH value reaction system is within the range of 2 to 12, and in particular within the range of 6 to 11. It is not preferable in the case where the pH value is not within this range, since hydrolyzing is reacted at the same time. Though reaction temperature is sufficient with room temperature, reaction time can be shortened by heating. Reaction time is required for 2 to 3 hours or more in general. Also, it is necessary that thiol group which formed by this reduction is not oxidized. Further, a good results can be obtained by operating under the atmosphere of inactive gas.

Thus obtained reducing decompositions made its derivatives (keratin reducing derivatives mentioned in the following) by chemical modifying thiol group of the reducing decompositions. As for the derivatives of the thiol group, the derivatives listed in the following are exemplified.

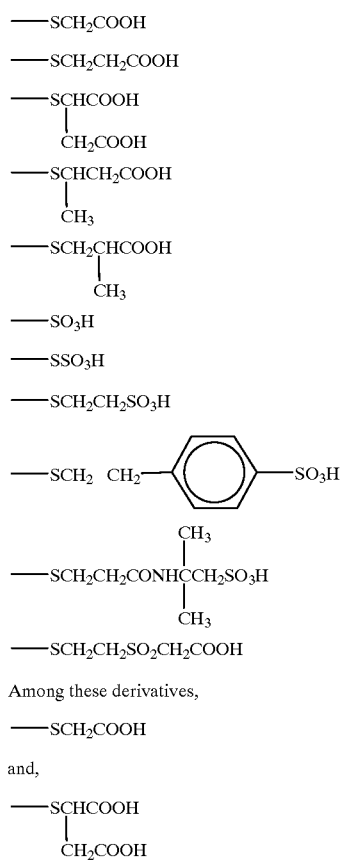

Among these derivatives,

—$SCH_2COOH$ and,

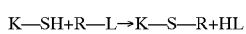

are preferable in particular.

Chemical modification method of thiol group is conducted according to the know method, e.g., N. H. Leon; Textile Progress, Volume 7, Page 1 (1975), "Organic Sulfuric Compound" written by Shigeru OHBA, published by Kagaku Dojin (1986), and "Polymer Experimental Course" written by Masami OKU, published by Kyoritsu Shuppan (1975). As for the representative methods, the methods shown in the following exists.

①method Using Nucleophilical Displacement Reaction of SH Group $$K—SH+R—L \rightarrow K—S—R+HL$$

(wherein, K, R, and L shows a residue of a keratin compound, a chemical modification group which is introduced, and eliminative atom or group of halogen atom, acid residue or the like, respectively.

As for a compound reacted by this method, for example, a halide such as iodoacetic acid, bromoacetic acid, chloroacetic acid, and the like are listed.

②method Using Nucleophilical Displacement Reaction to Double Bond between Carbon of SH Group

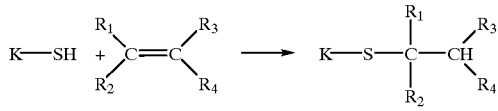

(wherein, one or more among $R_1$, $R_2$, $R_3$, and $R_4$ shows a group which has a carboxyl or a sulfonic group in inside, a rest shows an alkyl group or hydrogen atom, and K has a meaning explained above).

As for a compound reacted by this method, for example, acrylic acid, methacrylic acid, crotonic acid, maleic acid, fumaric acid, vinylcarboxymethyl sulfonic acid, vinyl sulfonic acid, styrene sulfonic acid, 2-acrylamide-2-methyl propane sulfonic acid, and the like can be listed.

③ Method Using Displacement Reaction between SH Group and Sulphite Compound

K—SH+NaHSO$_3$→K—S—SO$_3$H

K—SH+Na$_2$SO$_3$→K—S—SO$_3$H

Air (wherein, K has a meaning explained above)

④ Method Oxidizing SH Group to Sulfonic Group

K—SH→K—SO$_3$H

Oxidation (wherein, K has a meaning explained above)

As for a oxidizer used for this reaction, for example, halogen and permanganate are exemplified.

As for alkali salt of oxidative decomposition and reducing derivative of the keratins, inorganic alkali metallic salts such as sodium, potassium and the like, or salts of organic base such as ammonium salt, ethanolamine, diethanolamine, triethanolamine, 2-amino-2-methylpropanol, amino mercaptopropanediol, triisopropanolamine, glycin, histidine, arginine, and the like are listed. Though these alkali salts can be compounded to a hair treatment agent by preparing another system, it is possible to form salt in the system which compounds oxidative decompositions of keratin or reducing derivatives of keratin and alkali materials. As for the alkali materials in this case, for example, inorganic alkali materials such as sodium hydroxide, potassium hydroxide, sodium carbonate, potassium carbonate, and the like, and organic alkali materials such as ammonia, ethanolamine, diethanolamine, triethanol-amine, 2-amino-2-methyl-1-propanol, 2-amino-2-methyl-1,3-propanediol, 2-amino-1-butanol, triisopropanol-amine, diisopropanolamine, monoisopropanolamine, arginine, histidine, hydroxylysine, and the like are listed. These materials are preferable to be compounded with 0.1 to 8 equivalent weight with respect to a carboxyl group or a sulfonic group in keratin oxidative decomposition or keratin reducing derivative.

Thus obtained keratin decomposition derivatives can be used separately or by mixing two or more for a hair cosmetic preparation of the present invention.

A preferable amount of the keratin decomposition derivative used in the present invention in 0.001 to 5 wt %, and more preferably 0.01 to 3 wt %.

In the case where the amount of the keratin decomposition derivative is less than 0.001 wt %, glossiness and moisture to a hair, and hair protecting effect are not given and an improvement effect of easiness of combing is not sufficiently displayed. On the contrary, an increase of the effect which is correspond to the increase of amount is not observed in the case where the amount of the keratin decomposition derivative is more than 5 wt %. Further, stickiness and odor of base are occurred in the case where the amount of the keratin decomposition derivative is extremely increased.

Also, a weight ratio of wax/(keratin decomposition derivatives selected from the group consisting of keratin hydrolyzate, alkali salt of keratin oxidative decomposition, and alkali salt of the derivative in thiol group of keratin material reducing decomposition) is preferably 6 to 150000. An excellent feel of use of the present invention will be spoiled in the case where the weight ratio is not within this range.

1. Synthesis of Keratin Decomposition Derivative

<Synthesizing Example 1>

Synthesis of Keratin Material Oxidative Decomposition Derivative (I) 10 g of a wool fiber was soaked in 700 g of 8% peracetic acid solution for 1 day at room temperature and oxidative reaction was conducted. The obtained oxidation treatment wool was filtrated and washed with water. When the obtained oxidation treatment wool was soaked in 700 g of 1N ammonia water for 1 day at room temperature, about 90 g of wool was solubilized to ammonia water. After eliminating about 1 g of an insolubilized portion, pH was adjusted to 4.0 by adding 2N hydrochloric acid to ammonia solution of keratose which was the obtained wool keratin oxidative decomposition. Then, α-keratose was separated out as a precipitation. After filtrating α-keratose and washing with acetone, 5.4 g of α-keratose was obtained by drying.

(II) After pressuring and heating a wool fiber in a high pressure vessel with 6 kg/cm$^2$ of saturated steam for 6 hours, a porous expanded material was obtained by releasing the wool fiber suddenly to an air. 10 g of a ground of the porous expanded material, 250 g of formic acid, and 50 g of 30% hydrogen peroxide were entered into a three-necked flask capability of 500 ml and the mixture was soaked for 1 day. In this time, there was no formation of powder, a bubble-like mass was floated in the upper layer of the mixture. After filtrating this reaction mixture, its filtrate was poured into 1.5 L of water and was adjusted pH to 4 with hydrochloric acid. 4.5 g of α-keratose was obtained by separating precipitation which was obtained with filtrating and washing it with 500 ml of water. Further, 350 ml of water was added to an insolubilized portion which obtained the reacted mixture with filtrating, and it was adjusted pH to 11 with ammonia water and was soaked for 1 day. The pH value was adjusted to 4 by adding hydrochloric acid to a filter paper and the filtrate portion. Then, 0.7 g of α-keratose was obtained by obtaining a separated precipitation. 1.4 g of the insolubilized portion was mainly β-keratose.

<Synthesizing Example 2>

Synthesis of Keratin Reducing Decomposition Derivative (I) 10 g of a wool fiber was soaked in 600 ml solution of 8M urea and 0.01M Tris buffer and 6 ml of 2-mercaptoethanol was added to the mixture as a reducing agent. Then, the mixture was adjusted to pH 10 with 5N caustic potash solution and reducing reaction was conducted under the stream of nitrogen at room temperature. After about 3 hours, about 85% of wool was solubilized to the reacted solution. 16.5 g of acetic acid iodide was gradually added to the mixture while adjusting so as not to decrease the value of pH of the system lower than 7. The pH value of the system was finally adjusted to 8.5, carboxymethylated reaction was conducted for 2 hours under room temperature. After removing an insolubilized portion by filtrating the reacted solution, the obtained filtrate was added to a cellulose tube. The filtrate was dialyzed to ion-exchanged water and low-molecular impurities such as urea were removed. According as urea was dialyzed, HGT (a component which has high content of glycin and tyrosine) which is water-insoluble component was separated and the material in the cellulose tube was clouded. After ending the dialysis, HGT was removed by centrifugal separation. The obtained S-carboxymethylkelatin (SCMKA) was separated out as a precipitation from the neutral transparent solution of SCMKA with being insoluble by isoelectric point precipitation method. After dividing this by filtration and washing with ethanol, 4.2 g of SCMKA was obtained by drying.

(II) 5.3 g of S-(1,2-dicarboxyethyl)-keratin was obtained by the same operation with Synthesizing Example 2 (I) except for using a porous expanded material which was obtained by using a feather in place of a wool fiber, which was heated in a high pressure vessel for 6 hours with superheated steam of 6 kg/cm$^2$, 240° C., and suddenly released to the air and for using 17.5 g of maleic acid in place of acetic acid iodide.

(III) 4.2 g of S-(2-carboxyethyl)-keratin was obtained by the same operation with Synthesizing Example 2 (I) except for using a grind of horse's hoof in place of a wool fiber and using 11 g of acrylic acid in place of acetic acid iodide.

(IV) 4.8 g of S-(sulphophenylvinyl)-keratin was obtained by the same operation with Synthesizing Example 2 (I) except for using 28 g of styrene sulfonic acid in place of acetic acid iodide.

(V) 8 g of a wool fiber was dispersed to 300 ml of n-propanol and 300 ml of 0.1N Tris buffer and was replaced with nitrogen. 3.2 ml of tri-n-butylphosphine was added to the dispersion and was stirred for 24 hours at room temperature. After filtrating the dispersion, 400 ml of water, 9.28 g of maleic acid and about 30 ml of 5N potassium hydroxide were added to an insolubilized portion and the mixture was adjusted pH at 8.0 while stirring for 6 hours at room temperature. Then, about 20 ml of 28% ammonia solution was added to the mixture and adjusted pH to 11.5 and the mixture was further stirred for 18 hours at room temperature. Then the insolubles were removed by filtrating the reaction solution and an obtained filtrate was entered into a cellulose tube. The filtrate was dialyzed to ion-exchanged water and low-molecular impurities such as urea were removed. After ending the dialysis, the insolubles in the cellulose tube was removed by centrifugal separation and a neutral transparent solution was obtained. 5.5 ml of 1N hydrochloric acid was added to the neutral transparent solution and pH was adjusted to 4.4. A separated precipitation was obtained by filtration and was washed with ethanol. 3.9 g of S-(1,2-dicarboxyethyl)-keratin was obtained by drying the precipitation.

(VI) 4.5 g of keratin-S-(2-acrylamide-2-methyl propane sulfonic acid) was obtained by the same operation with Synthesizing Example 2(V) except for using a grind of a porous expanded material which was obtained by using a wool in place of a wool fiber which was heated in a high pressure vessel for 6 minutes with saturated steam of 6 kg/cm$^2$ and suddenly released to the air and for using 16.5 g of 2-acrylamide-2-methyl propane sulfonic acid in place of maleic acid.

<Synthesizing Example 3>

Synthesis of Keratin Hydrolyzate Derivative (I) 10 g of a wool fiber was soaked in 300 g of 1% sodium hydrogensulfite solution and the solution was adjusted pH to 6.7 with 5N caustic soda solution. 0.2 g of papain was further added to the solution and hydrolyzing reaction was conducted for 15 hours at 60° C. About 80% of the wool was solubilized. An impurities were removed by filtration. Sulfite in the obtained filtrate was removed by using a membrane of molecular cutoff 500 according to ultrafiltration method and the hydrolyzate solution was thickened. 7.7 g of the hydrolyzate having a molecular weight 500 to 2000 was obtained by freezing and drying the hydrolyzate solution.

(II) 10 g of a wool fiber was soaked in 300 g of 75% phosphoric acid solution and the solution was hydrolyzed for 5 hours at 120 to 130° C. After cooling the solution and removing an insolubilized portion, 4 to 5 times amount of water was added to the solution and the insolubilized portion was further removed by centrifuging. Then, calcium carbonate or barium hydroxide was added to the solution. After adjusting pH to 6.7, a precipitation was obtained by filtrating. Then, 8.0 g of the hydrolyzate having a molecular weight 500 to 2000 was obtained by drying the solution. (According to the manufacturing process of Synthesizing Examples 3, (I) and (II), it was understood that cystine in the wool was not destroyed in the process of hydrolysis, because the weight of S—S bonds has 50 mol per the hydrolysate of $10^5$g.)

(III) A porous expanded material was obtained by heating 100 g of a feather in high pressure vessel for 6 minutes with superheated steam of 6 kg/cm$^2$, 240° C. After grinding the expanded material, 3 L of 0.3N caustic soda was added and hydrolyzed for 18 hours at 60° C. After hydrolysis, the reaction solution was neutralized with 1N hydrochloric acid and was filtrated. Salt in an obtained filtrate wad removed by using a membrane of molecular cutoff 500 according to ultrafiltration method and the keratin hydrolyzate solution was thickened. 7.2 g of keratin hydrolyzate was obtained by freezing and drying the keratin hydrolyzate solution. A molecular weight of the keratin hydrolyzate was 1800 in the case where the weight was measured according to gel filtration method.

(IV) 100 g of a grind of horse's hoof whose grain size were determined to 0.25 to 1 mm was degreased with 50% methanol and 50% chloroform solution. Then, soluble protein was removed with 1% ammonia water and entered to a three-necked flask. 20 g of sodium hydroxide and 400 g of ion-exchanged water were added to the solution and hydrolyzed for 4 hours while stirring at 90° C. After cooling and adjusting pH to 8 with hydrochloric acid, the reaction water was filtrated, 68 g of keratin hydrolyzate was obtained by the same operation with Synthesizing Example 3 (III) after the operation of removing salt in the hydrolyzate. A molecular weight of the keratin hydrolyzate was 2500 in the case where the weight was measured according to gel filtration method.

(D) Silylated Peptide

Silylated peptide used in the present invention is that a functional group which comprises only silicon atom is covalently bonded to an amino group of peptide which comprises an amino group of amino acid side chain which is represented by the following Formula (1) or (2), Silylated peptide represented by, Formula (1):

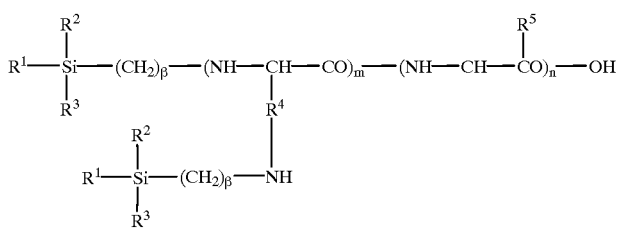

(wherein, $R^1$, $R^2$ and $R^3$ shows an alkyl group or a hydroxyl group having a carbon number from 1 to 3, each carbon number of $R^1$, $R^2$ and $R^3$ can be same or different, $R^4$ shows a residue excluding terminal amino group of basic amino acid which has an amino group in terminal of side chain, $R^5$ shows an amino acid side chain excluding $R^4$, $\beta$ is 1 or 3, m is 0 to 200, n is 0 to 200, and m+n is 1 to 200. (In here, m and n only shows a number of the amino acid and does not show amino acid sequence.)).

Silylated peptide represented by,

Formula (2):

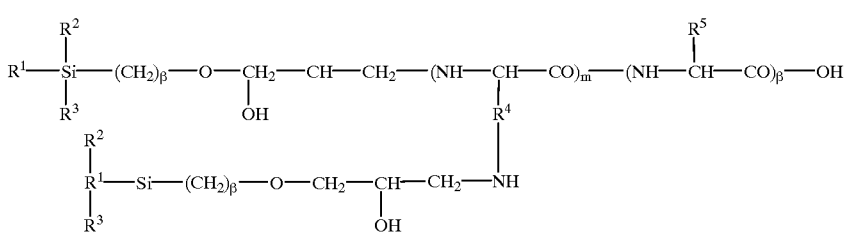

(wherein, $R^1$, $R^2$ and $R^3$ shows an alkyl group or a hydroxyl group having a carbon number from 1 to 3, each carbon number of $R^1$, $R^2$ and $R^3$ can be same or different, $R^4$ shows a residue excluding terminal amino group of basic amino acid which has an amino group in terminal of side chain, $R^5$ shows an amino acid side chain excluding $R^4$, $\beta$ is 1 or 3, m is 0 to 200, n is 0 to 200, and m+n is 1 to 200. (In here, m and n only shows a number of the amino acid and does not show amino acid sequence.)).

Silylated peptide represented in Formula (1) is, for example, obtained by condensation reaction with, a silylated compound shown by the following Formula (3):

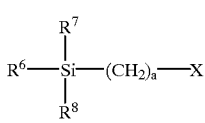

(wherein, $R^6$, $R^7$ and $R^8$ shows an alkyl group having a carbon number from 1 to 3, an alkoxy group having a carbon number from 1 to 3, a hydroxyl group or halogen atom, $R^6$, $R^7$ and $R^8$ can be same or different, a is 1 or 3, X shows halogen atom such as Cl, Br, F, and I), and peptide shown by the following Formula (4):

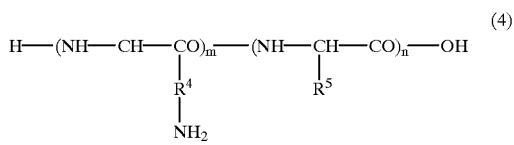

(wherein, $R^4$ shows a residue excluding amino group of basic amino acid having an amino group in the terminal of side chain, $R^6$ shows a side chain of amino acid excluding $R^4$, m is 0 to 200, n is 0 to 200, and m+n is 1 to 200).

Also, silylated peptide represented in Formula (2), is obtained by condensation reaction with, for example, a silylated compound shown by the following Formula (5):

$$R^6\text{—}\underset{\underset{R^8}{|}}{\overset{\overset{R^7}{|}}{Si}}\text{—}(CH_2)_a\text{—}O\text{—}CH_2\text{—}CH\underset{O}{\overset{}{\diagdown\diagup}}CH_2 \qquad (5)$$

(wherein, $R^6$, $R^7$ and $R^8$ shows an alkyl group having a carbon number from 1 to 3, an alkoxy group having a carbon number from 1 to 3, a hydroxyl group or halogen atom, $R^6$, $R^7$ and $R^8$ can be same or different, a is 1 or 3), and the peptide represented by Formula (4) shown above.

Property of Silylated Peptide

As is clear from chemical constitutional formula, silylated peptide represented by Formula (1) or (2) has silyl functional group portion comprising silicate atom according to the silylated compound represented by Formula (3) and (5) and peptide portion according to the peptide represented by Formula (4). Accordingly, an excellent spreadability, friction decrease, giving effect of glossiness or brightness, and giving effect of water repellency of silyl functional group portion and sorption effect to a hair, volume up of hair along with the sorption, giving effect of tension of hair, and protecting and moisturizing effect by film-forming of peptide portion can be coincidentally displayed in the case where the silylated peptide is compounded with a hair cosmetic preparation. Also, since the peptide has a good sorption to a damaged hair, said silylated peptide can be absorbed silyl function group to the damaged hair which is hard to adsorb with silicone of high molecular weight through the peptide portion. Accordingly, silylated peptide can improve a touch of the damaged hair and can contribute to recover the damaged hair.

Accordingly, said silylated peptide gives glossiness or brightness to a hair, makes a hair smooth, improves an easiness of hair combing, prevents a creation of a split hair and a lobed hair and recovering strength of a damaged hair, in the case where a hair cosmetic preparation was manufactured with compounding this silylated peptide.

Also, the silylated peptide represented by Formula (1) or (2) is that low molecular weight silyl functional group is bonded to the peptide portion and is absorbed to a hair with a normal sorption mechanism. Accordingly, the silylated peptide can be reversibly desorbed from a hair by washing with a washing agent which is not comprised peptide.

In the silylated peptide represented by Formula (1) or (2), the reason why $R^1$, $R^2$, $R^3$ was predetermined is that the silylated peptide represented by Formula (1) or (2) has water solubility and is to maintain a favorable preservation stability in water-soluble hair cosmetic preparation. Also, the reason why a is predetermined to 1 or 3 is that a preservation stability of the silylated compound represented by Formula (3) and (5) was bad in the case where a was 2. Also, in the case where a was more than 3, the property of the silyl functional group could not be sufficiently displayed, since the percentage of the silyl functional group in the whole molecular became small.

Peptide Portion in Silylated Peptide

In the silylated peptide represented by Formula (1) or (2), though $R^4$ is a residue excluding an amino group of basic amino acid having the terminal amino group of side chain. As for the amino acid having the amino group in the terminal of side chain, for example, lysine, arginine, hydroxylysine, and the like are listed. Also, $R^5$ shows a side chain of amino acid excluding $R^4$. As an examples of such amino acids, for example, glutamic acid, aspartic acid, alanine, serine, threonine, valine, methionine, leucine, isoleucine, tyrosine, phenylalanine, proline, hydroxyproline, and the like are listed. In the silylated peptide represented by Formula (1) or (2), m is 0 to 200 and preferably, 0<m≦50, and more preferably, 0<m≦10. Also, n is 0 to 200, and preferably 1 to 100, and more preferably, 2 to 40. Also, m+n is 1 to 200, and preferably 2 to 100, and more preferably, 3 to 50. These reasons are explained in the following.

In the case where the value of m is more than 200, silyl functional carbon which bonds to the amino group of side chain is increased and sorption effect to a hair of the peptide is decreased. Also, in the case where the value of n is more than 200, the property of silyl functional group portion can not be sufficiently displayed, since the percentage of silyl functional group portion becomes small. Further, in the case where the value of m+n is more than 200, preservation stability is decreased because the property of the peptide such as sorption or penetration to a hair is decreased as compared with the low molecular weight peptide and the peptide becomes easy to aggregate in preservation.

Though the value of m, n, or m+n are an integer in theory, a measured value becomes an average value in the case where the peptide portion is the hydrolyzed peptide as mentioned in the following, because said peptide is obtained as a mixture which has different molecular weight.

As an examples of the peptide represented by Formula (4), amino acid, peptide, alanine of amino acid or peptide, glycin, valine, leucine, isoleucine, proline, phenylalanine, tyrosine, serine, threonine, methionine, arginine, histidine, lysine, asparagine, aspartic acid, glutamine glutamic acid, cystine, cysteine, cysteic acid, tryptophan, hydroxyproline, O-phosphoserine, citrulline, and the like are listed.

The peptide listed above are the hydrolyzed peptide which can be obtained by partially hydrolyzing natural peptides, synthetic peptides and proteins with acid, alkali or enzyme.

As an examples of natural peptides, for example, glutathione, bacitracin A, insulin, glucagon, oxytocin, vasopressin, and the like are listed. Also, as an examples of synthetic peptides, for example, polyglycine, polylysine, polyglutamic acid, polyserine, and the like are listed.

As an examples of hydrolyzed peptide, the hydrolyzed peptides which are obtained by partially hydrolyzing proteins derived from animals and vegetables such as collagen (including gelatine which is the denaturation of collagen), keratin, silk fibroin, sericin, casein, conchiolin, elastin, vitelline protein of egg such as fowl, duck and the like, ovalbumin protein, soybean protein, wheat protein, corn protein, rice (rice bran) protein, potato protein, and the like and proteins derived from microbes such as yeast of Saccharomyces, Candida, Endomycoptis, yeast protein decomposed from a so-called brewer's yeast and sake yeast, proteins extracted from mushrooms, proteins separated from Chlorella, and the like, with acid, alkali or enzyme are listed.

As an examples of an esters of amino acid or peptide, ester with hydrocarbon alcohols having a carbon number from 1 to 20 in a carboxyl group amino acid or peptide, e.g., methylester, ethylester, propylester, isopropylester, laurylester, cetylester, 2-ethylhexylester, 2-hexyldecylester, stearylester, and the like are listed.

<Synthesis of Silylated Peptide>

The silylated peptide represented by Formula (1), is obtained by contact reaction with the silylated compounds represented by Formula (2) or Formula (5) and the peptides represented by Formula (4). As for the silylated compounds represented by Formula (3) or Formula (5), a commercially available materials as a silane coupler can be used. As an examples of the silane coupler, for example, TSL8390, TSL8219, TSL8395, TSL8326, TSL8325, TSL8320, TSL8355, TSL8350 (Trade name) manufactured by Toshiba Silicone Co., Ltd., SH6040, SH6076 (Trade name) manufactured by Nihon Unicar Co., Ltd., KMB403, KMB402, KMB703 (Trade name) manufactured by Sin etsu Silicone Co., Ltd., and the like are listed.

As a reaction of the silylated compound represented by Formula (3) or Formula (5) with the peptides represented by Formula (4), for example, the silylated compound was firstly hydrolyzed for 5 to 20 minutes at 30 to 50° C. in water. Then, an alkoxy group or a halogen atom which bonds with silicon atom is transformed to a hydroxyl group. Both are contacted by dripping the silylated compound which was hydroxylated, down to the solution of the peptide represented by Formula (4).

In said reaction, the peptide is preferably 30 to 50 wt % solution. Also, drip of the silylated compound which was hydroxylated was ended up within the time of 30 minutes to 5 hours.

It is preferable to maintain the pH value in reaction system to 8 to 11, and more preferably 9 to 10 with dripping alkali solution such as sodium hydroxide, potassium hydroxide and the like in the same time with reaction. Because the pH value after the reaction was decreased by formation of hydrogen halide with reaction at the reaction time in the case where the silylated compound represented by Formula (3) was used. Also, the pH value was not decreased by reaction, in the case where the silylated compound represented by Formula (5) was used. However, pH of the peptide solution is preferably adjusted to 8 to 11, and more preferably, 9 to 11, since reaction proceeds with basicity.

Though reaction can proceeds under ordinary temperature, the more temperature rises high, the more reaction rate becomes fast. However, it is preferable to adjust to 70° C. or less and more preferably 40 to 60° C., because the hydrolysis of the silylated compound is accelerated in the case where temperature becomes high under the condition of high pH value.

The progress and the termination of reaction can be confirmed by measuring the amount of amino nitrogen of the peptide in reaction according to Van Slyke method.

After the reaction, the reaction solution was neutralized and properly concentrated. Then the reaction solution was prepared with ion-exchanged resin, dialysis membrane, electrodialysis, gel filtration and ultrafiltration, and was provided for preparing a hair cosmetic in liquid or by powdering.

In the silylated peptide represented in said Formula (1), an introduction rate of silyl functional group (i.e., a functional group comprising only one of silicon atom) to an amino group of the peptide is preferably 50% to 85%. There is a possibility that the property based on the silylated compound is not fully displayed, in the case where the introduction rate of silyl functional group is less than 50%. Also, there is a possibilities that hydrophobic nature is increased and hydrophilic nature is decreased, in the case where the introduction rate is more than 85%.

Also, in the silylated peptide represented in said Formula (2), an introduction rate of silyl functional group to an amino group of the peptide is preferably 50% to 75%. There is a possibility that the property based on the silylated compound is not fully displayed, in the case where the introduction rate of silyl functional group is less than 50%. Also, there is a possibilities that hydrophobic nature is increased and hydrophilic nature is decreased, in the case where the introduction rate is more than 75%.

Also, an amount (content in hair cosmetic preparation) of the silylated peptide represented by Formula (1) or (4), is preferably 0.05 to 30 wt %, and more preferably 0.5 to 15 wt %. Namely, the effects for giving glossiness or moisture to a hair, protecting a hair, improving an easiness of hair combing and emulsion stability of high molecular silicone, are not sufficiently displayed in the case where the amount of the silylated peptide is less than 0.05 wt %. Also, an increase of the effect which is correspond to the increase of the amount is not observed in the case where the amount of the silylated peptide is more than 30 wt %. Further, stickiness is occurred in the case where the amount of the silylated peptide is extremely increased. In compounding to a hair cosmetic preparation, said silylated peptide can be used separately and by mixing two or more.

Next, synthesizing examples of the silylated peptides used in the present invention are explained.

<Synthesizing Example 1>

20% sodium hydroxide solution was dripped down to 50 g (10.6 millimol as a stoichiometrical mol number obtained by the measurement of amino nitrogen) of 30% solution of hydrolyzed collagen (hydrolyzate of collagen, average value of m=2, average value of n=18, average value of m+n=20). The pH value was adjusted to 9.5 and the solution was heated to 55° C.

As a silylating agent, 2.3 g of a silylated compound that $R^6$=$CH_3$, $R^7$=$OCH_3$, $R^8$=$OCH_3$, and a=3 in Formula (5) (1.0 equivalence weight to the amount of amino nitrogen of hydrolyzed collagen) was dissolved into water so as to became 15% solution. The solution was adjusted pH to 3.5 with hydrochronic acid and was stirred for 15 minutes at 50° C. Then, the solution was transformed to a hydroxyl group by hydrolyzing a methoxy group (—$OCH_3$).

The silylated compound solution which was transformed to the hydroxyl group was dripped down to the hydrolyzed collagen solution which was stirring at 55° C., for 30 minutes. After dripping, the solution was further stirred for 5 hours at 55° C. Then, the reaction was finished.

After the reaction, the introduction rate of silyl functional group was 67%, when the introduction rate of the hydrolyzed collagen of silyl functional group to amino nitrogen was found by measuring amino nitrogen.

After neutralizing the reaction solution with diluted hydrochloric acid, the solution was desalted by electrodialyser and was adjusted pH to 6.5. Then, 63 g of 20% of reaction product (silylated hydrolyzed collagen) solution was obtained by adjusting the concentration of the solution.

<Synthesizing Example 2>

20% sodium hydroxide solution was dripped down to 50 g (15 millimol as a stoichiometrical mol number obtained by the measurement of amino nitrogen) of 30% solution of hydrolyzed wheat protein (hydrolyzate of wheat protein, average value of m=1.2, average value of n=8.8, average value of m+n=10). The pH value was adjusted to 9.5 and the solution was heated to 55° C.

As a silylating agent, 3.1 g of a silylated compound that $R^6$=Cl, $R^7$=$CH_3$, $R^8$=Cl, and a=3 in Formula (5) (0.9 equivalence weight to the amount of amino nitrogen of hydrolyzed wheat protein) was dissolved into water so as to be 15% solution. The solution was stirred for 15 minutes and transformed Cl atom which directly bonds to silicon atom to a hydroxyl group.

The silylated compound solution which was transformed to the hydroxyl group was dripped down to the hydrolyzed wheat protein solution which was stirring at 55° C., for 1 hour. After dripping, the solution was further stirred for 5 hours at 55° C. Then, the reaction was finished.

After neutralizing the reaction solution with diluted hydrochloric acid, the solution was desalted by electrodialyser. 55 g of 20% of reaction product (silylated hydrolyzed wheat protein) solution was obtained by adjusting the concentration of the solution. The introduction rate of silyl functional group was 62%.

<Synthesizing Example 3>

20% sodium hydroxide solution was dripped down to 50 g (42 milli mol as a stoichiometrical mol number obtained by the measurement of amino nitrogen) of 30% solution of hydrolyzed keratin (hydrolyzate of wool, average value of m=0.6, average value of n=4.4, average value of m+n=5). The pH value was adjusted to 9.5 and the solution was heated to 55° C.

As a silylating agent, 75 g of a silylated compound that $R^6$=$CH_3$, $R^7$=$OC_2H_5$, $R^8$=$OC_2H_5$, and a=3 in Formula (5)

(0.8 equivalence weight to the amount of amino nitrogen of hydrolyzed keratin) was dissolved into water so as to be 15% solution. The solution was adjusted pH to 3.5 with hydrochronic acid and was stirred for 15 minutes at 50° C. Then, the solution transformed an ethoxy group (OC$_2$H$_5$) which directly bonds to silicon atom to a hydroxyl group.

The silylated compound solution which was transformed to the hydroxyl group was dripped down to the hydrolyzed keratin solution which was stirring at 55° C. for 30 minutes. After dripping, the solution was further stirred for 5 hours at 55° C. Then, the reaction was finished.

After neutralizing the reaction solution with diluted hydrochloric acid, the solution was desalted by electrodialyser. 58 g of 20% of reaction product (silylated hydrolyzed keratin) solution was obtained by adjusting the concentration of the solution. The introduction rate of silyl functional group was 59%.

<Synthesizing Example 4>

20% sodium hydroxide solution was dripped down to 50 g (18.4 millimol as a stoichiometrical mol number obtained by the measurement of soybean protein) of 30% solution of hydrolyzed soybean protein (hydrolyzate of soybean protein, average value of m=0.5, average value of n=5.5, average value of m+n=6). The pH value was adjusted to 9.5 and the solution was heated to 55° C.

As a silylating agent, 75 g of silylated compound that R$^6$=OCH$_3$, R$^7$=OCH$_3$, R$^8$=OCH$_3$, and a=1 in Formula (5) (0.9 equivalence weight to the amount of amino nitrogen of hydrolyzed soybean protein) was dissolved into water so as to be 15% solution. The solution was adjusted pH to 3.5 with hydrochronic acid and was stirred for 15 minutes at 50° C. Then, the solution transformed a methoxy group which directly bonds to silicon atom to a hydroxyl group.

The silylated compound solution which was transformed to the hydroxyl group was dripped down to the hydrolyzed soybean protein solution which was stirring at 55° C., for 30 minutes. After dripping, the solution was further stirred for 5 hours at 55° C. Then, the reaction was finished.

After neutralizing the reaction solution with diluted hydrochloric acid, the solution was desalted by electrodialyser. 53 g of 20% of reaction product (silylated hydrolyzed soybean protein) solution was obtained by adjusting the concentration of the solution. The introduction rate of silyl functional group was 60%.

<Synthesizing Example 5>

20% sodium hydroxide solution was dripped down to 50 g (30 millimol as a stoichiometrical mol number obtained by the measurement of yeast protein) of 30% solution of hydrolyzed yeast protein (hydrolyzate of yeast protein, average value of m=1.2, average value of n=6.8, average value of m+n=8). The pH value was adjusted to 9.5 and the solution was heated to 55° C.

As a silylating agent, 75 g of a silylated compound that R$^6$=CH$_3$, R$^7$=OC$_2$H$_5$, R$^8$=OC$_2$H$_5$, and a=3 in Formula (5) (0.8 equivalence to the amount of amino nitrogen of hydrolyzed yeast protein) was dissolved into water so as to be 15% solution. The solution was adjusted pH to 3.5 with hydrochronic acid and was stirred for 15 minutes at 50° C. Then, the solution transformed an ethoxy group which directly bonds to silicon atom to a hydroxyl group.

The silylated compound solution which was transformed to the hydroxyl group was dripped down to the hydrolyzed yeast protein solution which was stirring at 55° C., for 30 minutes. After dripping, the solution was further stirred for 5 hours at 55° C. Then, the reaction was finished.

After neutralizing the reaction solution with diluted hydrochloric acid, the solution was desalted by electrodialyser. 48 g of 20% of reaction product (silylated hydrolyzed yeast protein) solution was obtained by adjusting the concentration of the solution. The introduction rate of silyl functional group was 57%.

<Synthesizing Example 6>

10 g of L-lysine hydrochloride (molecular weight 182.6, 54.7 millimol) was dissolved into 100 ml of water. 20% sodium hydroxide solution was dripped down to the solution. The pH value was adjusted to 9.5 and the solution was heated to 55° C.

As a silylating agent, 17.8 g of a silylated compound that R$^6$=OCH$_3$, R$^7$=OCH$_3$, R$^8$=OCH$_3$, and a=3 in Formula (5) (0.7 equivalence weight to the amount of amino nitrogen of L-lysine hydrochloride) was dissolved into water so as to be 15% solution. The solution was adjusted pH to 3.5 with hydrochronic acid and was stirred for 15 minutes at 50° C. Then, the solution transformed an methoxy group to a hydroxyl group.

The silylated compound solution which was transformed to the hydroxyl group was dripped down to the L-lysine hydrochloride solution which was stirring at 55° C., for 30 minutes. After dripping, the solution was further stirred for 5 hours at 55° C. Then, the reaction was finished.

After the reaction, the introduction rate of silyl functional group was 65%, when the introduction rate of silyl functional group was found by measuring the amount of amino nitrogen. It was understood that the amino group of peptide terminal as well as the amino group of side chain were reacted. After neutralizing the reaction solution with diluted hydrochloric acid, the solution was desalted by electrodialyser and was adjusted pH to 6.5. 118 g of 15% of reaction product (silylated L-lysine) solution was obtained by adjusting the concentration of the solution.

<Synthesizing Example 7>

10 g of glycyl-L-alanine (molecular weight 146.1, 68.4 millimol) was dissolved into 100 ml of water. 20% sodium hydroxide solution was dripped down to the solution. The pH value was adjusted to 9.5 and the solution was heated to 55° C.

As a silylating agent, 13.5 g of a silylated compound that R$^6$=CH$_3$, R$^7$=OCH$_3$, R$^8$=OCH$_3$, and a=1 in Formula (5) (0.9 equivalence weight to the amount of amino nitrogen of glycyl-L-alanine) was dissolved into water so as to be 15% solution. The solution was adjusted pH to 3.5 with hydrochronic acid and was stirred for 15 minutes at 50° C. Then, the solution transformed an methoxy group which directly bonds to silicon atom to a hydroxyl group.

The silylated compound solution which was transformed to the hydroxyl group was dripped down to the glycyl-L-alanine solution which was stirring at 55° C., for 30 minutes. After dripping, the solution was further stirred for 5 hours at 55° C. Then, the reaction was finished.

After neutralizing the reaction solution with diluted hydrochloric acid, the solution was desalted by electrodialyser and was adjusted pH to 6.5. 104 g of 15% of reaction product (silylated glycyl-L-alanine) solution was obtained by adjusting he concentration of the solution. The introduction rate of silyl functional group was 55%.

Compounding Amount of Silylated Peptide

A compounding amount of the silylated peptide used in the present invention is 0.01 to 30.0 wt %, and preferably 0.1 to 20.0 wt % with respect to the whole amount of a hair cosmetic preparation. The effects by compounding silylated peptide such as less stickiness of hand and smoothness of hair can not be obtained in the case where the amount of silylated peptide is less than 0.01 wt %. Also, in the case where the amount is more than 30.0 wt %, it is difficult to compound in the view of solubility and bad odor was occurred.

(E) Polyether Compound that Propylene Oxide and/or Ethylene Oxide is Additionally Polymerized to Nucleus of Polyhydric Alcohol An emulsified composition comprising polyether compound that propylene oxide and/or ethylene oxide is addition-polymerized to nucleus of polyhydric alcohol which is the second part of an oil-in-water hair cosmetic preparation of the present invention will be explained.

An oil-in-water emulsified composition of polyether compound that propylene oxide and/or ethylene oxide is addition-polymerized to nucleus of polyhydric alcohol can be used the composition which was prepared by ordinary method. Also, in considering skin irritation as like a fine dispersion composition of wax, a complex which can be obtained by mixing amphoteric surfactant and/or semi-polar surfactant and higher fatty acid as shown in Japanese Unexamined Patent Publication No. Hei 6-65596, can be used.

Polyether Compound that Propylene Oxide and/or Ethylene Oxide is Additionally Polymerized to Nucleus of Polyhydric Alcohol A polyether compound used in the present invention is the polyether compound that propylene oxide and/or ethylene oxide is addition-polymerized to nucleus of polyhydric alcohol. In this invention, a preferable polyether compound group is (1) the polyether compound that 1 to 10 mol, preferably 3 to 7 mol of ethylene oxide (EO mentioned in the following) is additionally polymerized to the backbone chain which additionally polymerized 20 to 90 mol, and preferably 50 to 70 mol of propylene oxide (PO mentioned in the following) to the nucleus of the polyhydric alcohols which has a functional group having 3 to 6 of terminal hydroxyl group such as glycerin, diglycerine, pentaerythritol, trimethylolpropane, mannitane, sorbitan, mannitol and sorbitol.

Among these compounds, it is preferably that 40 to 80 mol of PO and 3 to 10 mol of EO is additionally polymerized to the nucleus of pentaerythritol in succession.

In the polyether compound group of (1), the nucleus of the polyhydric alcohol is used by the reason which aims to increase the PO addition portion to 3–6. Also, it was selected for the purpose of increasing polarity without losing suitable oiliness. However, as a result of study, the polarity region which can sufficiently solve hair washness and a factor of adhesion of dirt cannot be obtained with only PO additional polymerization. Accordingly, additional polymerization of EO having limited mol number is required. A limited mol number of EO, namely 1 to 10 mol of EO is determined since celluloid corrosiveness is occurred in the case where mol number of EO is more than 10 mol.

Also, in the polyether compound group of (1) has molecular structure of copolymer such as block copolymer and random copolymer (comprising sandwich type). As a result of test, the compounds of block polymer is excellent in hair washness as compared with the compounds of random polymer, since terminal group of block polymer has water-solubility. This is considered that random polymer has oil solubility. Also, significance with respect to celluloid corrosiveness is not changed. The inventors studied phosphoric acid ester of polyether compound which is additionally polymerized 1 to 10 mol of EO to the backbone chain which additionally polymerized 20 to 90 mol of PO to the nucleus of the polyhydric alcohol. However, they confirmed that hair dressing retention and usability (stickiness of hand) are not preferably as compared with the polyether compounds which are used in the present invention.

Also, as for the other preferable polyether compounds, (2) a polyether compounds that 20 to 100 mol of PO or 40 to 120 mol of PO and 1 to 20 mol of EO is additionally polymerized to polyglycerines more than triglycerine, are listed.

In the polyether compounds of (2), Polyglycerine: i.e., polyglycerine mixture ore than triglycerine, the polyether compound that 20 to 100 mol, preferably 40 to 80 mol of PO or 40 to 120 mol of PO and 1 to 20 mol of EO, preferably 3 to 10 mol of EO is additionally polymerized to the polyglycerine which has 5 or more of a terminal hydroxyl group. Among of these compounds, the compound that 50 to 90 mol of PO is additionally polymerized to the nucleus of decaglycerin is most preferable.

In the case where an addition of PO with respect to polyglycerine is lower mol, celluloid corrosiveness is strong. Celluloid corrosiveness is disappeared in the case where 20 mol or more of PO is added. Also, viscosity becomes moderate and viscosity of 500 to 1500 mPa/S is shown as an oily component of hair dressing agent, in need. Further, the polyether compound which can easily wash off dirt of hand with city water, and which has favorable water dispersion even in the case where 100 mol of PO is added, since 5 to 8 of polar group of terminal hydroxyl group of polyglycerine is efficiently functioned. Also, the compound has oiliness and water dispersion is inferior in the case where the optimum PO is added to polyglycerine. However, the compound which is excellent in hair dressing ability and water solubility and which has no celluloid corrosiveness can be obtained in the case where 1 to 20 mol of EO is further added to the compound. This may have the same property with the compound which was obtained by additional polymerization of PO with ore than optimum mol number after adding 1 to 20 mol of EO to polyglycerine. Further, the inventors studied about phosphoric acid ester of these polyether compounds. However they confirmed that the polyether compounds is not favorable in hair dressing retention and fat-solubility (stickiness of hand) as compared with the polyether compound used in the present invention.

Also, in the polyether compound group of (2) has molecular structure of copolymer such as block copolymer and random copolymer (comprising sandwich type). As a result of test, the compounds of block polymer are excellent in hair washness as compared with the compounds of random polymer, since a terminal group of block polymer has water-solubility.

This is considered that random polymer has more oil solubility. Also, significance with respect to celluloid corrosiveness is not changed. The inventors studied phosphoric acid ester of polyether compound which additionally polymerized 1 to 10 mol of EO to the backbone chain which additionally polymerized 20 to 90 mol of PO to the nucleus of the polyhydric alcohol. However, they confirmed that hair dressing retention and usability (stickiness of hand) are not preferable as compared with the polyether compounds which are used in the present invention.

In addition to the polyether compound groups described in above, the polyether compound used in the hair cosmetic preparation of the present invention can be adopted the manufacturing process of ordinary method. For example, particulate caustic soda is mixed with polyhydric alcohol in $N_2$ gas. Then, PO is slowly added to the mixture under the conditions of reaction temperature of 100 to 120° C. and internal pressure 5 to 7 kg/cm²G. Propylene oxide/ethylene oxide additional polymerization of polyhydric alcohol can be obtained by adding EO to the mixture. Such polyether compound is, for example, shown in Japanese Patent Publication No. Sho 55-10567.

A polyether compound that propylene oxide and/or ethylene oxide is additionally polymerized to nucleus of polyhydric alcohol used in the present invention can be used separately or by mixing two or more. An amount of said polyether compound is preferably 1 to 30 wt %. The effects of the present invention such as hair dressing power in particular, are not obtained in the case where the amount is less than 1 wt %. On the other hand, stickiness is occurred in the case where the amount is more than 30 wt %.

Also, a weight ratio of wax/(polyether compound that propylene oxide and/or ethylene oxide is additionally polymerized to the nucleus of polyhydric alcohol) is preferably 0.2 to 10. An excellent feel of use of the present invention is spoiled in the case where the weight ratio is not within this range.

(F) Extracts from Vegetables

An extracts from vegetables used in the hair cosmetic preparation of the present invention are extracted by using water or/and a water-soluble organic solvent or an oil-soluble organic solvent. As an examples of a water-soluble organic solvent used in extraction: alcohols, for example, monohydric alcohols such as methanol, ethanol, propanol, butanol, and the like; polyhydric alcohols of propylene glycols such as 1,3-propylene glycol, butylene glycols such as 1,3-butylene glycol, and the like are preferable. These water-soluble organic solvent can be used separately or by mixing two or ore, and is preferably to use by mixing with water. In extracting by mixing with water, a ratio of water to the water-soluble organic solvent is preferably about 3:1 to 1:5, more preferably 2:1 to 1:2, most preferably about 1:1.

Also, as for the oil-soluble organic solvent, liquid petrolatum, sunflower seed oil, squalane, almond oil, persic oil and corn oil are preferable.

As a definite examples of the extracts from vegetable used in the present invention are the extracts listed in the following.

As an examples of a water-soluble vegetable extracts, angelica extract, gambir extract, hydrangea extract, althea extract, arnica extract, aloe extract, ginkgo extract, nettle extract, fennel extract, rose fruit extract, scutellaria root extract, phellodendron bark extract, japanese coptis extract, barley extract, hypericum extract, watercress extract, seaweed extract, hydrolyzed wheat protein solution, chamomile extract, cattail extract, oat extract, artemisia capillaris extract, apricot kernel extract, quince seed extract, gardenia extract, sasa albo-mar ginata extract, chlorella extract, sophora root extract, clematis extract, mulberry bark extract, geranium harb extract, black tea extract, nuphar extract, burdock root extract, wheat germ extract, rice bran extract, comfrey extract, asiasarum root extract, saponaria extract, crataegus fruit extract, zanthoxylum fruit extract, shiitake extract, rehmannia root extract, lithospermum root extract, perilla extract, linden extract, filipendula extract, paeony root extract, ginger extract, birch extract, honeysuckle extract, horsetail extract, ivy extract, sambucus extract, yarrow extract, peppermint extract, sage extract, mallow extract, cnidium rhizome extract, swertia herb extract, thyme extract, green tea extract, clove extract, citrus unshiu peel extract, centella extract, capsicum tincture, japanese angelica root extract, calendula extract, peach seed extract, biter orange peel extract, houttuynia extract, ginseng extract, wild rose extract, parsley extract, witchhazel extract, rose extract, isodonis extract, loquat leaf extract, grape leaf extract, hoelen extract, butcher broom extract, sponge gourd extract, safflower extract, paeonia extract, hops extract, horse chestnut extract, balm mint extract, sweet clover extract, peach leaf extract, cornflower extract, eucalyptus extract, saxifrage extract, lily extract, coix extract, lavender extract, rosemary extract, romanchamomile extract, burnet extract, and the like are listed.

As an examples of the oil-soluble vegetable extracts, oil-soluble arnica extract, oil-soluble camomile extract, oil-soluble shikon extract, oil-soluble linden extract, oil-soluble horsetail extract, oil-soluble yallow extract, oil-soluble sage extract, oil-soluble japanese angelica extract, oil-soluble wild rose extract, oil-soluble loquat leaf extract, oil-soluble horse chestnut extract, oil-soluble peach leaf extract, oil-soluble coix seed extract, oil-soluble rosemary extract, and the like can be listed.

The extracts which are extracted from the vegetables listed in above which can be used in a hair cosmetic preparation of the present invention can be used separately or by mixing two or more.

A favorable amount of the extract from vegetables is 0.001 to 5 wt %, and more preferably 0.01 to 3 wt % with respect to the whole amount of the hair cosmetic preparation.

In the case where the amount of the extract is less than 0.001 wt %, glossiness and moisture to a hair, and hair protecting effect are not given and an improvement effect of easiness of combing is not sufficiently displayed. On the other hand, an increase of the effect which is correspond to the increase of the amount is not observed in the case where the amount of the extract which is extracted from vegetables are more than 5 wt %. Further, stickiness and odor of base are occurred in the case where the amount of extract is extremely increased.

Also, a weight ratio of wax/(extracts from vegetables) is preferably 3 to 15000. An excellent feel of use of the present invention is spoiled in the case where the weight ratio is not within this range.

(G) Silicone Derivatives

As for a silicone derivative which can be used in emulsion part of the present invention, dimethyl polysiloxane, methyl phenyl polysiloxane, polyether denatured silicone, epoxy denatured silicone, fluorine denatured silicone, alcohol denatured silicone, alkyl denatured silicone, alkoxy denatured silicone, and the like can be exemplified. In concrete, the silicone derivatives shown in the following formula (6) to (20) are used in favorably.

(I) Dimethyl polysiloxane represented by the following Formula (6)

(6)

Formula (6):

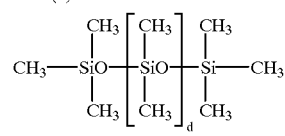

(wherein, d shows a number from 3 to 20000)

(II) Methyl phenyl siloxane represented by the following Formula (7) or (8)

Formula (7):
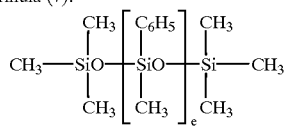
(7)

Formula (8):
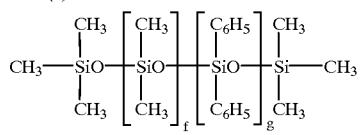
(8)

(wherein, e shows a number from 1 to 20000 and f+g shows a number from 1 to 500)

(III) Polyether denatured silicone represented by Formula (9) to (12)

Formula (9):
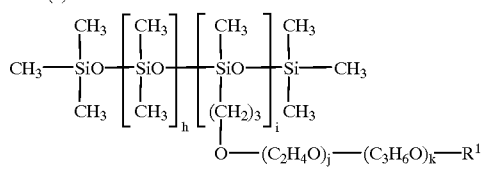
(9)

(wherein, $R^1$ shows a hydrogen atom or an alkyl group having a carbon number from 1 to 12, h, i, j, k shows 1 to 10 (preferably, 3 to 30), 1 to 50 (preferably, 1 to 30), 1 to 50 (preferably, 3 to 30), 0 to 50 (preferably, 0 to 30), respectively, and a sum of h and i is more than 15 and the sum of j and k is more than 5)

Formula (10):
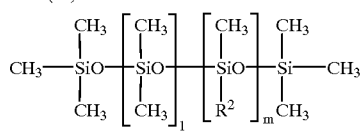
(10)

Formula (11):
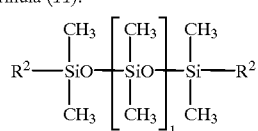
(11)

Formula (12):
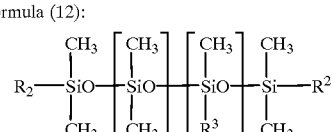
(12)

(wherein $R_2$ is $(CH_2)_3-O-(C_2H_4O)_D-(C_3H_6O)_E-A$ (A shows a hydrogen atom or an alkyl group having a carbon number from 1 to 12, D and E shows a number from 0 to 50, $D+E \geq 1$), l shows a number from 1 to 2000, m shows a number from 1 to 1000)

(IV) Epoxy denatured silicone represented by Formula (13)

Formula (13):
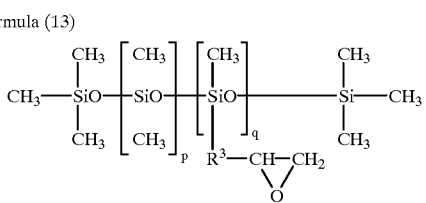
(13)

(wherein, p, q and $R^3$ shows a number from 1 to 500 (preferably, 1 to 250), a number from 1 to 50 (preferably, 1 to 30), and an alkylene group having a carbon number from 1 to 3, respectively)

(V) Fluorine denatured silicone represented by Formula (14)

Formula (14):
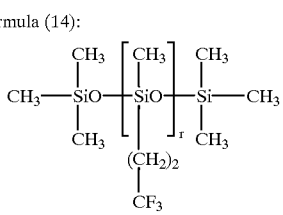
(14)

(wherein, r shows a number from 1 to 400 (preferably 1 to 250)

(VI) Alcohol denatured silicone represented by Formula (15) or (16)

Formula (15):
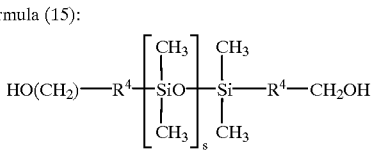
(15)

Formula (16):
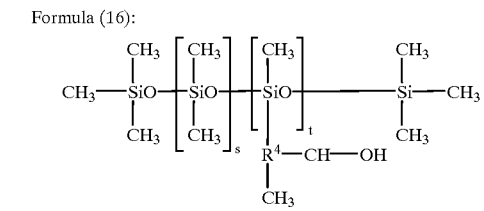
(16)

(wherein, s and t shows a number from 1 to 500 (preferably 1 to 200) and $R^4$ shows $C_FH_{2F}$ (F shows a number from 0 to 4))

(VII) Alkyl denatured silicone represented by Formula (17) or (18)

Formula (17):
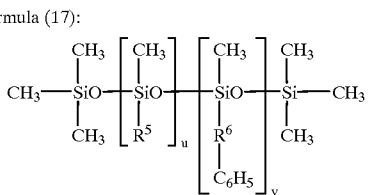
(17)

-continued

Formula (18):

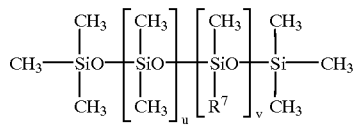
(18)

(wherein, u and v shows a number from 1 to 500 (preferably 1 to 200) and $R^5$ shows an alkyl group having a carbon number from 2 to 18, $R^6$ shows $C_G H_{2G}$ (G shows a number from 0 to 4), and $R^7$ shows an alkyl group having a carbon number from 10 to 16.)

(VIII) Alkoxy denatured silicone represented by Formula (19)

Formula (19):

$$\mathrm{CH_3-\underset{\underset{CH_3}{|}}{\overset{\overset{CH_3}{|}}{Si}}O-\left[\underset{\underset{R^8}{|}}{\overset{\overset{R^8}{|}}{Si}}O\right]_\beta-\left[\underset{\underset{(CH_2)_w}{|}}{\overset{\overset{CH3}{|}}{Si}}O\right]-\left[\underset{\underset{(CH_2)_w}{|}}{\overset{\overset{O-R^9}{|}\;\;(CH_2)_w}{Si}}O\right]_\gamma-\underset{\underset{O-R^9}{|}}{\overset{\overset{CH_3}{|}}{Si}}-CH_3}$$
(19)

(wherein, $R^8$ shows a methyl group or a phenyl group, $R^9$ shows an alkyl group having a carbon number from 1 to 28 (preferably 12 to 22), w shows an integer from 0 to 6, β shows an integer from 1 to 3000, γ and δ shows an integer that m+n=1 to 500)

(IX) Amino denatured silicone represented by Formula (20)

Formula (20):

$$R^b-\underset{\underset{R^a}{|}}{\overset{\overset{R^a}{|}}{Si}}O-\left[\underset{\underset{R^a}{|}}{\overset{\overset{R^a}{|}}{Si}}O\right]_x-\left[\underset{\underset{R^c}{|}}{\overset{\overset{R^a}{|}}{Si}}O\right]_y-\underset{\underset{R^a}{|}}{\overset{\overset{R^a}{|}}{Si}}-R^b$$
(20)

(wherein, $R^a$ shows a methyl group or a phenyl group in a part, $R^b$ shows the same with $R^c$ or a methyl group or a hydroxyl group, $R^c$ shows a substituent group having an amino group or an ammonia group represented by a formula $R^d Z\{R^d$ shows a divalent alkylene group having a carbon number from 3 to 6, Z shows a monovalent group selected from the group consisting of $-NR^E_2$, $-N^+R^E_3 A^-$, $-NR^E (CH_2)_\alpha NR^E_2$, $-NR^E(CH_2)_\alpha N^+R^E_3 A^-$, and $-NR^E(CH_2)_\alpha N(R^E)C=O(R^F)(R^E$ shows a hydrogen or an alkyl group having a carbon number from 1 to 4, $R^F$ shows an alkyl group having a carbon number of 1 to 4, A shows a chlorine atom, a bromine atom or an iodine atom, α is an integer from 2 to 6), x and y are an integer of a positive number, x+y shows an integer from 3000 to 20000, y/x is 1/500 to 1/10000)

A compounding amount of said silicone derivative is 0.1 to 35 wt %, and more preferably 3 to 30 wt %. An excellent effect of this invention such as less stickiness and smoothness can not be obtained in the case where the amount of the silicone derivative is less than 0.1 wt %. Also, in the case where the amount of the silicone derivative is more than 35 wt %, there is almost no improvement in feel of use.

A weight ratio of wax/silicone derivative is preferably 0.1 to 10. an excellent feel of use of the present invention is spoiled in the case where the weight ratio is not within this limitation.

(H) High Molecular Compound Having Film-Forming Ability

As an examples of a high molecular compound having film-forming ability, anionic high molecular compounds such as acrylate-methacrylate copolymer (Plascize, manufactured by Goo Chemical Company, Ltd.), vinyl acetate/crotonic acid copolymer (Resyn 28-1310, manufactured by National Starch & Chemical Company (NSC Comp. mentioned in follow)), vinyl acetate/crotonic acid/vinyl neodecanoate copolymer (Resyn 28-2930, manufactured by NSC Comp.), methyl vinyl ether maleic acid half ester (Gantrex ES, manufactured by ISP VAN DYK), and the like, amphoteric high molecular compounds such as acetate amphoteric compound of dialkylamino ethylmethacrylate copolymer (Yukaformer, manufactured by Mitsubishi Chemical Company Ltd.), octylacrylamide acrylates/hydroxypropyl acrylates/butyl methacrylate copolymer (Amphomer, manufactured by NSC Comp.), and the like, nonionic high molecular compounds such as polyvinylpyrrolidone (Luviskol K, manufactured by BASF Corp.), PVP/VA copolymer (PVP/VA S-630, manufactured by ISP VAN DYK), PVP/dimethylaminoethyl-methacrylate copolymer (Copolymer 937, manufactured by NSC Comp.), cationic high molecular compounds such as polyquaternium of vinylpyrrolidone/dimethylaminoethyl-methacrylate (Gafquat, manufactured by ISP VAN DYK), and the like can be listed.

Also, as for an amphoteric high molecular compound, the compounds mentioned in the prior art can be listed. However, N-methacryloyl ethyl N,N-dimethyl ammonium/α-N-methyl carboxy betaine/alkyl methacrylate copolymer (Yukaformer, manufactured by Mitsubishi Chemical Company Ltd.) which is monochrol acetate amphoteric compound of dialkylaminoethyl methacrylate copolymer such as Formula (21), is preferable in view of less stickiness in the case where a hair dressing is used.

Formula (21)

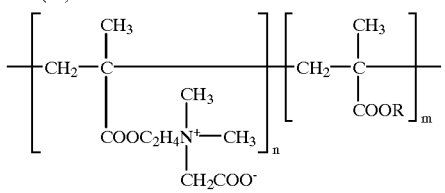
(21)

(wherein, R shows an alkyl group having a carbon number from 1 to 18, n:m is 10:90 to 90:10, and an average molecular weight is 20000 to 30000)

An amphoteric high molecular compound is excellent in a little as compared with the other high molecular compounds in view of less stickiness at the time of application.

A compounding amount of high molecular compound which has film-forming ability is 0.1 to 30 wt %, and more preferably 0.5 to 20 wt %. An excellent retention effect of hair dressing can not be obtained in the case where the amount of the high molecular compound is less than 0.1 wt %. Also, in the case where the amount of the high molecular compound is more than 30 wt %, there is almost no improvement in feel of use. The high molecular compounds shown above can be used in separately or by mixing two or more of the compounds.

A weight ratio of wax/high molecular compound which has film forming ability is preferably 0.5 to 150. an excellent feel of use of the present invention is spoiled in the case where the weight ratio is not within this limitation.

(I) Water-soluble Thickening Agent

As an examples of a water-soluble thickening agent used in the present invention, carboxyvinylpolymer, alkyl denatured carboxyvinylpolymer, carboxymethylcellulose, methylcellulose, ethylcellulose, hydroxypropyl methylcellulose, hydroxyethyl methylcellulose, xanthan gum, hydroxyethylcellulose, polyvinyl pyrrolidone/methacrylate N,N'-dimethyl aminoethyl/stearyl acrylate/tripropylene glycol diacrylate copolymer, and the like can be listed.

Compound Amount of Water-Soluble Thickening Agent

A compounding amount of water-soluble thickening agent is 0.1 to 3 wt %, and more preferably 0.5 to 2 wt %. An excellent retention effect of the present invention such as less stickiness of hand and easiness of hand combing can not be obtained in the case where the amount of the water-soluble thickening agent is less than 0.1 wt %. Also, in the case where the amount of the water-soluble thickening agent is more than 50 wt %, there is almost no improvement in feel of use.

A weight ratio of wax/water-soluble thickening agent is preferably 0.2 to 135. An excellent fee of use of the present invention is spoiled in the case where the weight ratio is not within this limitation.

(J) Polyhydric Alcohol Higher Than Bivalent Alcohol

As for a polyhydric alcohols higher than bivalent alcohol which can be used in the hair cosmetic preparation of the present invention, all the polyhydric alcohol which can be used in cosmetic are listed. For example, glycerin, ethylene glycol, polyethylene glycol, 1,2-propylene glycol, 1,3-propylene glycol, 1,3-butylene glycol, dipropylene glycol, sorbitol, mannitol, 1,2-pentanediol, 2-methyl-1,3-propanediol, 1,2,3-butanetriol, 1,2,4-butanetriol, hexylene glycol, isoprene glycol, and the like are listed.

The polyhydric alcohol higher than bivalent alcohol listed in above which is used in the present invention can used in separately or by mixing two or more.

An amount of the polyhydric alcohol higher than bivalent alcohol which is used in the present invention is preferably 0.1 to 30 wt %, and more preferably 0.5 to 20 wt % with respect to the whole amount of the hair cosmetic preparation. Spreadability in application and lack of flaking is deteriorated in the case where the amount of the polyhydric alcohol is less than 0.1 wt %. On the other hand, stickiness is occurred in the case where the amount of the polyhydric alcohol is more than 30 wt %.

Also, a weight ratio of wax/polyhydric alcohol higher than bivalent alcohol is preferably 0.5 to 150. An excellent feel of use of the present invention is spoiled in the case where the weight ratio is not within this range.

<Test Examples of Hair Cosmetic Preparation>

Next, a test examples of a hair cosmetic preparation of the present invention are shown. An all compounding amounts are shown by wt %.

The present inventors conducted an experiment shown in the following in the process of studying a hair cosmetic preparation which has an excellent property with respect to less stickiness, smoothness, and easiness of combing.

Then, the present inventors prepared a hair cosmetic preparation shown in the following so as to examine an effect of the present invention. The present inventors used the obtained Working Examples and comparative Examples or Test Examples as a sample and evaluated with respect to <stickiness of hand>, <easiness of hand combing>, <smoothness>, <glossiness>, and <hair dressing power>. Evaluation methods are shown in the following.

<Stickiness of hand>

1 g of sample was taken to a palm. After rubbing the hands, stickiness of hand was organoleptically evaluated.

◎: Largely improved as compared with the sample which only compounded the fine dispersion composition of wax of the present invention ○: Improved as compared with the sample which only compounded the fine dispersion composition of wax of the present invention Δ: Slightly improved as compared with the sample which only compounded the fine dispersion composition of wax of the present invention –: Not improved as compared with the sample which only compounded the fine dispersion composition of wax of the present invention <Easiness of hand combing>

2 g of sample was coated on to a hair strand (4 g) and arranged its form with a comb. Easiness of hand combing was evaluated in right after and after 6 hours.

◎: Largely improved as compared with the sample which only compounded the fine dispersion composition of wax of the present invention ○: Improved as compared with the sample which only compounded the fine dispersion composition of wax of the present invention Δ: Slightly improved as compared with the sample which only compounded the fine dispersion composition of wax of the present invention –: Not improved as compared with the sample which only compounded the fine dispersion composition of wax of the present invention <Smoothness>

2 g of sample was coated on to a hair strand (4 g) and arranged its form with a comb. Then, smoothness of the hair strand was evaluated in right after and after 6 hours.

◎: Largely improved as compared with the sample which only compounded the fine dispersion composition of wax of the present invention ○: Improved as compared with the sample which only compounded the fine dispersion composition of wax of the present invention Δ: Slightly improved as compared with the sample which only compounded the fine dispersion composition of wax of the present invention —: Not improved as compared with the sample which only compounded the fine dispersion composition of wax of the present invention <Hair Dressing Power>

Figure 10:
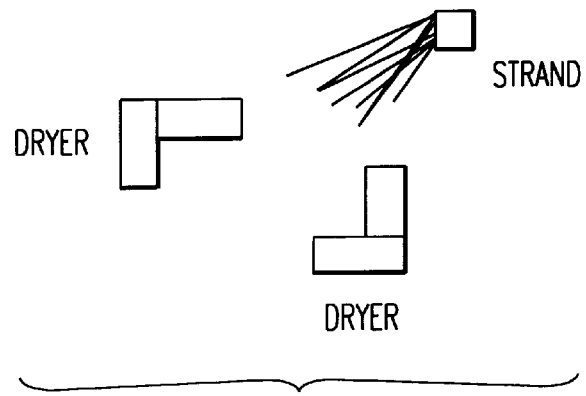
FIG. 10 shows a method for testing hair dressing power of the compositions which were prepared by working examples, comparative examples, and test examples of the present invention.

2 g of sample was coated on to a hair strand (4 g) and arranged its form with a comb. Then the strand was blown by a dryer as shown in FIG. 10. A stretch condition of the strand was evaluated with visual observation.

◎: Largely improved as compared with the sample which only compounded the fine dispersion composition of wax of the present invention ○: Improved as compared with the sample which only compounded the fine dispersion composition of wax of the present invention Δ: Slightly improved as compared with the sample which only compounded the fine dispersion composition of wax of the present invention —: Not improved as compared with the sample which only compounded the fine dispersion composition of wax of the present invention <Glossiness>

◎: Largely improved as compared with the sample which only compounded the fine dispersion composition of wax of the present invention ○: Improved as compared with the sample which only compounded the fine dispersion composition of wax of the present invention Δ: Slightly improved as compared with the sample which only compounded the fine dispersion composition of wax of the present invention —: Not improved as compared with the sample which only compounded the fine dispersion composition of wax of the present invention (A) Hydrocarbon Oil and/or Ester Oil A hair cosmetic preparation which compounds a fine dispersion composition of wax and hydrocarbon oil and/or ester oil is shown in the following.

Ingredient of the Present Invention

Test Example 19, Test Example 20, and Test Example 21 is the composition of the present invention, the composition excluding the hydrocarbon oil, and the composition excluding wax, respectively. The evaluation standard is Test Example 20 which compounds the fine dispersion composition of wax and which does not compounds the specific ingredient. The evaluations are conducted according to this standard.

TABLE 11

| Set Lotion | Test Ex. 19 | Test Ex. 20 | Test Ex. 21 |
|---|---|---|---|
| (Wax part) | | | |
| (1 Carnauba wax | 15.0 | 15.0 | — |
| (2) Polyoxyethylene behenyl ether (10EO) | 10.0 | 10.0 | 10.0 |
| (3) Cocoyl fatty acid amide dimethyl amino acetic acid betaine*1 | 5.0 | 5.0 | 5.0 |
| (4) Ion-exchanged water | 70.0 | 70.0 | 85.0 |
| (Emulsion part) | | | |
| (1) Liquid petrolatum | 40.0 | — | 40.0 |
| (2) 1,3-butylene glycol | 5.0 | 5.0 | 5.0 |
| (3) Isostearic acid*2 | 1.0 | 1.0 | 1.0 |
| (4) Sodium 2-undecyl-N,N,N-(hydroxyethylcarboxymethyl)-2-imidazolinium betaine*3 | 5.0 | 5.0 | 5.0 |
| (5) Ion-exchanged water | 49.0 | 89.0 | 49.0 |
| (Set lotion) | | | |
| (1) Emulsion part | 69.8 | 69.8 | 69.8 |
| (2) Wax part | 30.0 | 30.0 | 30.0 |
| (3) Methylparaben | 0.2 | 0.2 | 0.2 |
| Evaluation | | | |
| Stickiness of hand | ⊚ | — | Δ |
| Easiness of hand combing | | | |
| (Right after) | ⊚ | — | ○ |
| (After 6 hours) | ⊚ | — | — |
| Smoothness | | | |
| (Right after) | ⊚ | — | Δ |
| (After 6 hours) | ⊚ | — | Δ |
| Hair dressing power | | | |
| (Right after) | ⊚ | — | — |
| (After 6 hours) | ⊚ | — | — |

*1:Trade name ; Rebon2000-SF, manufactured by Sanyo Chemical Industries Ltd., (significant part 30%)
*2:Trade name ; Isostearic Acid EX, manufactured by Kokyu Alcohol Co., Ltd.)
*3:Trade name ; Ovazoline 662N-SF desalted, manufactured by Toho Chemical Industry Co., Ltd. (significant part 30%)

<Manufacturing Process of Wax Part>

The ingredients (1) to (4) were stirred about 95° C. After the mixture had transparency, the mixture was cooled down with ice and a fine dispersion composition of wax was obtained.

<Manufacturing Process of Emulsion Part>

The ingredients (1) to (4) and a part of the ingredient (5) were stirred and emulsified by a homomixer. Then, a emulsified composition was obtained by adding the rest of the ingredient (5).

<Manufacturing Process of Set Lotion>

A shake type set lotion was obtained by mixing the above-mentioned two compositions and the ingredient (3) in the ratio which is shown in TABLE 11.

As is clear from the results shown above, though Test Example 21 which did not compound wax could be obtained a little feel of use in view of less stickiness of hand, smoothness of hand combing and smoothness, it was largely inferior in hair dressing power as compared with Test Example 20. On the contrary, Test Example 19 which compounded the hydrocarbon oil and/or the ester oil was improved in all of the views such as less stickiness of hand, easiness of hand combing, smoothness, and hair dressing power. Also, it was appreciated that these effects were maintained even after 6 hours has passed.

Structure of the Emulsified Composition of the Present Invention

A hair cosmetic preparation of the present invention was obtained by mixing a fine dispersion composition of wax and an emulsified composition which comprising hydrocarbon oil and/or ester oil which were prepared separately in advance.

A composition which was almost same composition with the composition of Test Example 19 of the present invention and was prepared without dividing wax part and emulsion part, was determined as Test Example 22.

The difference between an oil-in-water hair cosmetic preparation of the present invention and Test Example 22 is explained in the following. Though emulsion particle of hydrocarbon oil and/or ester oil and dispersion particle of wax existed in separately in the present invention, both formed the same dispersion particle in the composition of Test Example 22.

| Test Example 22 | |
|---|---|
| (1) Carnauba wax | 4.5 |
| (2) Polyoxyethylene behenyl ether (10EO) | 3.0 |
| (3) Cocoyl fatty acid amide dimethyl amino acetic acid betaine*1 | 1.5 |
| (4) Liquid petrolatum | 28.0 |
| (5) 1,3-butylene glycol | 3.5 |
| (6) Isostearic acid*2 | 0.7 |
| (7) Sodium 2-undecyl-N,N,N-(hydroxyethylcarboxymethyl)-2-imidazolinium betaine*3 | 3.5 |
| (8) Ion-exchanged water | 55.3 |
| Evaluation: | |
| Stickiness of hand | Δ |
| Easiness of hand combing | Δ |
| | (After 6 hours —) |
| Smoothness | Δ |
| | (After 6 hours —) |
| Hair dressing power | — |
| | (After 6 hours —) |

<Manufacturing Process of Test Example 22>

The ingredients (1) to (7) and a part of the ingredient (8) were mixed and stirred at 95° C. and a fine dispersion composition of wax which comprised the hydrocarbon oil was obtained. Then, a set lotion was obtained by adding the rest of the ingredient (8).

As a result, it is apparent that an excellent feeling of use such as less stickiness of hand, easiness of hand combing, and smoothness can be obtained in the cases where a dispersion particle of wax and particle of hydrocarbon oil and/or ester oil are existed in separately.

Compounding Amount of Hydrocarbon Oil and/or Ester Oil

Next, the present inventors studied about a compounding amount of hydrocarbon oil and/or ester oil and a weight ratio of wax/(hydrocarbon oil and/or ester oil) by changing the compounding ratios of a fine dispersion composition of wax (wax part) and an emulsified composition comprising a hydrocarbon oil and/or an ester oil (emulsion part).

TABLE 12

| Set Lotion | Test ex. 23 | Test ex. 24 | Test ex. 25 | Test ex. 26 | Test ex. 27 | Test ex. 28 | Test ex. 29 |
|---|---|---|---|---|---|---|---|
| (Wax part) | | | | | | | |
| (1) Carnauba wax | 15.0 | 15.0 | 15.0 | 15.0 | 15.0 | 15.0 | 15.0 |
| (2) Polyoxyethylene behenyl ether (10EO) | 10.0 | 10.0 | 10.0 | 10.0 | 10.0 | 10.0 | 10.0 |
| (3) Cocoyl fatty acid amide dimethyl amino acetic acid betaine*1 | 5.0 | 5.0 | 5.0 | 5.0 | 5.0 | 5.0 | 5.0 |
| (4) Ion-exchanged water | 70.0 | 70.0 | 70.0 | 70.0 | 70.0 | 70.0 | 70.0 |
| (Emulsion part) | | | | | | | |
| (1) Liquid petrolatum | 50.0 | 50.0 | 50.0 | 50.0 | 50.0 | 50.0 | 50.0 |
| (2) 1,3-butylene glycol | 5.0 | 5.0 | 5.0 | 5.0 | 5.0 | 5.0 | 5.0 |
| (3) Isostearic acid*2 | 1.0 | 1.0 | 1.0 | 1.0 | 1.0 | 1.0 | 1.0 |
| (4) Sodium 2-undecyl-N,N,N-(hydroxyethyl carboxymethyl)-2-imidazolinium betaine*3 | 5.0 | 5.0 | 5.0 | 5.0 | 5.0 | 5.0 | 5.0 |
| (5) Ion-exchanged water | 49.0 | 49.0 | 49.0 | 49.0 | 49.0 | 49.0 | 49.0 |
| (Set lotion) | | | | | | | |
| (1) Wax part | 99.0 | 97.0 | 70.0 | 50.0 | 40.0 | 30.0 | 15.0 |
| (part of wax) | (14.85) | (14.6) | (10.5) | (7.5) | (6.0) | (4.5) | (0.75) |
| (2) Emulsion part | 0.8 | 2.8 | 29.8 | 49.8 | 59.8 | 69.8 | 84.8 |
| (part of hydrocarbon oil) | (0.4) | (1.4) | (14.9) | (24.9) | (29.9) | (34.9) | (42.4) |
| (3) Ethylparaben | 0.2 | 0.2 | 0.2 | 0.2 | 0.2 | 0.2 | 0.2 |
| Wax/Hydrocarbon Oil | 37.1 | 10.4 | 0.7 | 0.3 | 0.25 | 0.13 | 0.02 |
| Evaluation | | | | | | | |
| Stickiness of hand | Δ | ○ | ⊚ | ⊚ | ⊚ | ⊚ | ○ |
| Easiness of hand combing | Δ | ○ | ⊚ | ⊚ | ⊚ | ⊚ | ○ |
| Smoothness | Δ | ○ | ⊚ | ⊚ | ⊚ | ⊚ | ○ |
| Hair dressing power | Δ | ○ | ⊚ | ⊚ | ⊚ | ○ | Δ |

As a results shown above, a preferable compounding amount of hydrocarbon oil and/or ester oil is about 1.0 to about 50 wt %. Also, a preferable weight ratio of wax/hydrocarbon oil and/or ester oil is 0.1 to 10.

(B) Phospholipid, Protein or Protein Hydrolyzate and Derivatives Thereof

Next, a hair cosmetic preparation which compounds a fine dispersion composition of wax and phospholipid, protein or protein hydrolyzate and derivatives thereof is shown in the following.

Ingredient of the Present Invention

Test Example 30, Test Example 31, and Test Example 32 is the composition of the present invention, the composition excluding the phospholipid and protein hydrolyzate, and the composition excluding wax, respectively.

TABLE 13

| Set Lotion | Test Ex. 30 | Test Ex. 31 | Test Ex. 32 |
|---|---|---|---|
| (1) Carnauba wax | 15.0 | 15.0 | — |
| (2) Polyoxyethylene behenyl ether (10EO) | 10.0 | 10.0 | 10.0 |
| (3) )Sodium 2-undecyl-N,N,N-(hydroxyethylcarboxymethyl)-2-imidazolinium betaine*3 | 5.0 | 5.0 | 5.0 |
| (4) Ion-exchanged water | 67.8 | 69.8 | 82.8 |
| (5) Soybean lecithin | 1.0 | — | 1.0 |
| (6) Casein hydrolyzate | 1.0 | — | 1.0 |

TABLE 13-continued

| Set Lotion | Test Ex. 30 | Test Ex. 31 | Test Ex. 32 |
|---|---|---|---|
| (7) Methylparaben | 0.2 | 0.2 | 0.2 |
| Evaluation | | | |
| Stickiness of hand | ⊚ | — | Δ |
| Easiness of hand combing | | | |
| (Right after) | ⊚ | — | ○ |
| (After 6 hours) | ⊚ | — | — |
| Smoothness | | | |
| (Right after) | ⊚ | — | Δ |
| (After 6 hours) | ⊚ | — | Δ |

TABLE 13-continued

| Set Lotion | Test Ex. 30 | Test Ex. 31 | Test Ex. 32 |
|---|---|---|---|
| Hair dressing power | | | |
| (Right after) | ⊙ | — | — |
| (After 6 hours) | ⊙ | — | — |

<Manufacturing Process of Set Lotion>

The ingredients (1) and a part of the ingredient (4) were stirred about 92° C. After the mixture had transparency, the mixture was cooled down with ice and a fine dispersion composition of wax was obtained. A set lotion was obtained by mixing the dissolution of the ingredients (5) to (7) with the rest of the ingredient (4).

A set lotion was obtained by mixing the above-mentioned two compositions and the ingredient (3) in the ratio which is shown in TABLE 13.

As is clear from the results shown above, though Test Example 32 which did not compound wax could be obtained a little feel of use in view of less stickiness of hand, smoothness of hand combing and smoothness, it was largely inferior in hair dressing power as compared with Test Example 31. On the contrary, Test Example 30 which compounded the fine dispersion composition of wax of the present invention and the phospholipid and the protein hydrolyzate was improved in all of the views such as less stickiness of hand, easiness of hand combing, smoothness, and hair dressing power. Also, it was appreciated that these effects were maintained even after 6 hours has passed.

Compounding Amount of Wax/Phospholipid and Protein or Protein Hydrolyzate and Derivatives Thereof Next, the present inventors studied about a compounding amount of phospholipid, protein or protein hydrolyzate, and the derivatives thereof by changing the compounding amount of phospholipid, protein or protein hydrolyzate, and the derivatives thereof.

TABLE 14

| Set Lotion | Test ex. 33 | Test ex. 34 | Test ex. 35 | Test ex. 36 | Test ex. 37 | Test ex. 38 |
|---|---|---|---|---|---|---|
| (Wax part) | | | | | | |
| (1) Carnauba wax | 15.0 | 15.0 | 15.0 | 15.0 | 15.0 | 15.0 |
| (2) Polyoxyethylene behenyl ether (10EO) | 10.0 | 10.0 | 10.0 | 10.0 | 10.0 | 10.0 |
| (3) Cocoyl fatty acid amide dimethyl amino acetic acid betaine*[1] | 5.0 | 5.0 | 5.0 | 5.0 | 5.0 | 5.0 |
| (4) Ion-exchanged water | 69.6998 | 69.698 | 69.5 | 67.7 | 66.7 | 64.7 |
| (5) Soybean lecithin | 0.0001 | 0.001 | 0.01 | 1.0 | 1.5 | 2.5 |
| (6) Casein hydrolyzate | 0.0001 | 0.001 | 0.01 | 1.0 | 1.5 | 2.5 |
| (7) Ethylparaben | 0.2 | 0.2 | 0.2 | 0.2 | 0.2 | 0.2 |
| (8) 2-phenoxyethanol | 0.1 | 0.1 | 0.1 | 0.1 | 0.1 | 0.1 |
| Evaluation | | | | | | |
| Stickiness of hand | Δ | ○ | ⊙ | ⊙ | ⊙ | ⊙ |
| Easiness of hand combing | Δ | ○ | ⊙ | ⊙ | ⊙ | ⊙ |

TABLE 14-continued

| Set Lotion | Test ex. 33 | Test ex. 34 | Test ex. 35 | Test ex. 36 | Test ex. 37 | Test ex. 38 |
|---|---|---|---|---|---|---|
| Smoothness | Δ | ○ | ⊙ | ⊙ | ⊙ | ⊙ |
| Hair dressing power | Δ | ○ | ⊙ | ⊙ | ⊙ | ⊙ |

As a results shown above, a preferable compounding amount of phospholipid and protein or protein hydrolyzate and the derivatives thereof is about 0.001 to about 5 wt %.

Also, in the case where the phospholipid and the protein or the protein hydrolyzate and the derivatives thereof is compounded more than 5 wt %, the composition is unsuitable as a cosmetic preparation since it sometimes occurs bad odor.

(C) Keratin Decomposition Derivatives

Next, a hair cosmetic preparation which compounds a fine dispersion composition of wax and keratin decomposition derivatives is shown in the following.

Ingredient of the Present Invention

Test Example 39, Test Example 40, and Test Example 42 is the composition of the present invention, the composition excluding the keratin decomposition derivatives, and the composition excluding wax, respectively.

TABLE 15

| Set Lotion | Test Ex. 39 | Test Ex. 40 | Test Ex. 41 |
|---|---|---|---|
| (1) Carnauba wax | 15.0 | 15.0 | — |
| (2) Polyoxyethylene behenyl ether (10EO) | 10.0 | 10.0 | 10.0 |
| (3) )Sodium 2-undecyl-N,N,N-(hydroxy-ethylcarboxymethyl)-2-imidazolinium betaine*[3] | 5.0 | 5.0 | 5.0 |
| (4) Ion-exchanged water | 67.8 | 69.8 | 82.8 |
| (5) Keratin decomposition derivative of (I) of Synthesizing Example 1 | 1.0 | — | 1.0 |
| (6) Keratin decomposition derivative of (V) of Synthesizing Example 2 | 1.0 | — | 1.0 |
| (7) Methylparaben | 0.2 | 0.2 | 0.2 |
| Evaluation | | | |
| Stickiness of hand Easiness of hand combing | ⊙ | — | Δ |
| (Right after) | ⊙ | — | ○ |
| (After 6 hours) | ⊙ | — | — |
| Smoothness | | | |
| (Right after) | ⊙ | — | Δ |
| (After 6 hours) | ⊙ | — | Δ |
| Glossiness | ⊙ | — | ○ |
| Hair dressing power | | | |
| (Right after) | ⊙ | — | — |
| (After 6 hours) | ⊙ | — | — |

<Manufacturing Process of Test Example 39>

The ingredients (1) and a part of the ingredient (4) were mixed and stirred about 95° C. After the mixture had transparency, the mixture was cooled down with ice and a fine dispersion composition of wax was obtained. A set lotion was obtained by mixing the dissolution of the ingredients (5) to (7) with the rest of the ingredient (4).

<Manufacturing Process of Test Example 40>

The ingredients (1) to (3) and a part of the ingredient (4) were stirred about 95° C. After the mixture had transparency, the mixture was cooled down with ice and a fine dispersion composition of wax was obtained. A set lotion was obtained by mixing the dissolution of the ingredients (5) to (7) with the rest of the ingredient (4).

<Manufacturing Process of Test Example 41>

A set lotion was obtained by adding the ingredient (4) to the ingredients (2), (3) and (5) to (7).

As is clear from the results shown above, though Test Example 41 which did not compound wax could be obtained a little feel of use in view of less stickiness of hand, smoothness of hand combing and smoothness, it was largely inferior in hair dressing power as compared with Test Example 40. On the contrary, Test Example 39 which compounded the fine dispersion composition of wax of the present invention and the keratin decomposition derivative was improved in all of the views such as less stickiness of hand, easiness of hand combing, smoothness, and hair dressing power. Also, it was appreciated that these effects were maintained even after 6 hours has passed.

Weight Ratio of Wax/Keratin Decomposition Derivatives

Next, the present inventors studied about a compounding amount of keratin decomposition derivative and a weight ratio of wax/keratin decomposition derivative by changing the compounding amount of keratin decomposition derivatives.

TABLE 16

| Set Lotion | Test ex. 42 | Test ex. 43 | Test ex. 44 | Test ex. 45 | Test ex. 46 | Test ex. 47 | Test ex. 48 |
|---|---|---|---|---|---|---|---|
| (Wax part) | | | | | | | |
| (1) Carnauba wax | 15.0 | 15.0 | 15.0 | 15.0 | 15.0 | 15.0 | 15.0 |
| (2) Polyoxyethylene behenyl ether (10EO) | 10.0 | 10.0 | 10.0 | 10.0 | 10.0 | 10.0 | 10.0 |
| (3) Cocoyl fatty acid amide dimethyl amino acetic acid betaine*1 | 5.0 | 5.0 | 5.0 | 5.0 | 5.0 | 5.0 | 5.0 |
| (4) Ion-exchanged water | 69.6999 | 69.699 | 69.69 | 68.7 | 68.2 | 64.7 | 63.7 |
| (5) Keratin decomposition derivative of (I) of Synthesizing Example 3 | 0.0001 | 0.001 | 0.01 | 1.0 | 1.5 | 5.0 | 6.0 |
| (6) Ethylparaben | 0.2 | 0.2 | 0.2 | 0.2 | 0.2 | 0.2 | 0.2 |
| (7) 2-phenoxyethanol | 0.1 | 0.1 | 0.1 | 0.1 | 0.1 | 0.1 | 0.1 |
| Weight ratio of Wax/(Keratin decomposition derivative) | 150000 | 15000 | 1500 | 15 | 10 | 3 | 2.5 |
| Evaluation | | | | | | | |
| Stickiness of hand | Δ | ○ | ⊙ | ⊙ | ⊙ | ○ | Δ |
| Easiness of hand combing | Δ | ○ | ⊙ | ⊙ | ⊙ | ○ | Δ |
| Smoothness | Δ | ○ | ⊙ | ⊙ | ⊙ | ⊙ | ⊙ |
| Glossiness | Δ | ○ | ⊙ | ⊙ | ⊙ | ⊙ | ⊙ |
| Hair dressing power | Δ | ○ | ⊙ | ⊙ | ⊙ | ⊙ | ⊙ |

As a results shown above, a preferable compounding amount of keratin decomposition derivatives is about 0.001 to about 5 wt %.

Also, a preferable weight ratio of wax/(keratin decomposition derivative) is 3 to 15000.

(D) Silylated Peptide

Next, a hair cosmetic preparation which compounds a fine dispersion composition of wax and a silylated peptide is shown in the following.

Ingredient of the Present Invention

Test Example 49, Test Example 50, and Test Example 51 is the composition of the present invention, the composition excluding the silylated peptide and the composition excluding wax, respectively.

TABLE 17

| Set Lotion | Test Ex. 49 | Test Ex. 50 | Test Ex. 51 |
|---|---|---|---|
| (1) Carnauba wax | 15.0 | 15.0 | — |
| (2) Polyoxyethylene behenyl ether (10EO) | 10.0 | 10.0 | 10.0 |
| (3) )Sodium 2-undecyl-N,N,N-(hydroxyethylcarboxymethyl)-2-imidazolinium betaine*3 | 5.0 | 5.0 | 5.0 |
| (4) Ion-exchanged water | 67.8 | 69.8 | 82.8 |
| (5) Silylated peptide of Synthesizing Example 1 | 1.0 | — | 1.0 |
| (6) Silylated peptide of Synthesizing Example 2 | 1.0 | — | 1.0 |
| (7) Methylparaben | 0.2 | 0.2 | 0.2 |
| Evaluation | | | |
| Stickiness of hand | ⊙ | — | Δ |
| Easiness of hand combing | | | |
| (Right after) | ⊙ | — | ○ |
| (After 6 hours) | ⊙ | — | — |
| Smoothness | | | |
| (Right after) | ⊙ | — | Δ |
| (After 6 hours) | ⊙ | — | Δ |
| (After 12 hours) | ⊙ | — | — |
| Glossiness | ⊙ | — | ○ |
| Hair dressing power | | | |
| (Right after) | ⊙ | — | — |
| (After 6 hours) | ⊙ | — | — |

<Manufacturing Process of Test Example 49>

The ingredients (1) and a part of the ingredient (4) were mixed and stirred about 95° C. After the mixture had transparency, the mixture was cooled down with ice and a fine dispersion composition of wax was obtained. A set lotion was obtained by mixing the dissolution of the ingredients (5) to (7) with the rest of the ingredient (4).

<manufacturing Process of Test Example 50>

The ingredients (1) to (3) and a part of the ingredient (4) were stirred about 95° C. After the mixture had transparency, the mixture was cooled down with ice and a fine dispersion composition of wax was obtained. A set lotion was obtained by mixing the dissolution of the ingredients (5) to (7) with the rest of the ingredient (4).

<Manufacturing Process of Test Example 51>

A set lotion was obtained by adding the ingredient (4) to the ingredients (2), (3) and (5) to (7).

As is clear from the results shown above, though Test Example 51 which did not compound wax could be obtained a little feel of use in view of less stickiness of hand, smoothness of hand combing and smoothness, it was largely inferior in hair dressing power as compared with Test Example 50. On the contrary, Test Example 49 which compounded the fine dispersion composition of wax of the present invention and the silylated peptide was improved in all of the views such as less stickiness of hand, easiness of hand combing, smoothness, and hair dressing power. Also, it was appreciated that these effects were maintained even after 6 hours has passed.

Compounding Amount of Silylated Peptide

Next, the present inventors studied about a compounding amount of the silylated peptide and a weight ratio of wax/silylated peptide by changing the compounding amount of the silylated peptide.

TABLE 18

| Set Lotion | Test ex. 52 | Test ex. 53 | Test ex. 54 | Test ex. 55 | Test ex. 56 | Test ex. 57 |
|---|---|---|---|---|---|---|
| (Wax part) | | | | | | |
| (1) Carnauba wax | 15.0 | 15.0 | 15.0 | 15.0 | 15.0 | 15.0 |
| (2) Polyoxyethylene behenyl ether (10EO) | 10.0 | 10.0 | 10.0 | 10.0 | 10.0 | 10.0 |
| (3) Cocoyl fatty acid amide dimethyl amino acetic acid betaine*[1] | 5.0 | 5.0 | 5.0 | 5.0 | 5.0 | 5.0 |
| (4) Ion-exchanged water | 69.699 | 69.69 | 69.6 | 59.7 | 49.7 | 39.7 |
| (5) Silylated peptide of Synthesizing Example 1 | 0.001 | 0.01 | 0.1 | 10.0 | 20.0 | 30.0 |
| (6) Ethylparaben | 0.2 | 0.2 | 0.2 | 0.2 | 0.2 | 0.2 |
| (7) 2-phenoxyethanol | 0.1 | 0.1 | 0.1 | 0.1 | 0.1 | 0.1 |
| Weight ratio of Wax/(Silylated peptide) | 15000 | 1500 | 150 | 1.5 | 0.75 | 0.5 |
| Evaluation | | | | | | |
| Stickiness of hand | Δ | ○ | ⊚ | ⊚ | ⊚ | ⊚ |
| Easiness of hand combing | Δ | ○ | ⊚ | ⊚ | ⊚ | ⊚ |
| Smoothness | Δ | ○ | ⊚ | ⊚ | ⊚ | ⊚ |
| Glossiness | Δ | ○ | ⊚ | ⊚ | ⊚ | ⊚ |
| Hair dressing power | Δ | ○ | ⊚ | ⊚ | ⊚ | ⊚ |

As a results shown above, a preferable compounding amount of silylated peptide is 0.001 to 30 wt %, and more preferably 0.5 to 20 wt %.

Also, a preferable weight ratio of wax/(silylated peptide) is about 0.5 to 1500.

(D) Polyether Compound that Propylene Oxide and/or Ethylene Oxide is Additionally Polymerized to Nucleus of Polyhydric Alcohol Next, a hair cosmetic preparation which compounds a fine dispersion composition of wax and a polyether compound that propylene oxide and/or ethylene oxide is additionally polymerized to nucleus of polyhydric alcohol is shown in the following.

Ingredient of the Present Invention

Test Example 58, Test Example 59, and Test Example 60 is the composition of the present invention, the composition which only compounds the fine dispersion composition of wax and the composition which only compounds the polyether compound that propylene oxide and/or ethylene oxide is additionally polymerized to nucleus of polyhydric alcohol, respectively.

TABLE 19

| Set Lotion | Test Ex. 58 | Test Ex. 59 | Test Ex. 60 |
|---|---|---|---|
| (Wax part) | | | |
| (1) Carnauba wax | 15.0 | 15.0 | — |
| (2) Polyoxyethylene behenyl ether (10EO) | 10.0 | 10.0 | 10.0 |
| (3) )Sodium 2-undecyl-N,N,N-(hydroxy-ethylcarboxymethyl)-2-imidazolinium betaine*[3] | 5.0 | 5.0 | 5.0 |
| (4) Ion-exchanged water | 70.0 | 70.0 | — |
| (Emulsion part) | | | |
| (1) Pentaerythritol (PO) 65 mol (EO) 4.5 mol additions | 30.0 | — | 30.0 |
| (2) Isostearic acid*[2] | 1.0 | 1.0 | 1.0 |
| (3) )Sodium 2-undecyl-N,N,N-(hydroxy-ethylcarboxymethyl)-2-imidazolinium betaine*[3] | 5.0 | 5.0 | 5.0 |
| (4) Ion-exchanged water | 59.0 | 89.0 | 59.0 |
| (Set lotion) | | | |
| (1) Wax part | 30.0 | 30.0 | 30.0 |
| (2) Emulsion part | 69.8 | 69.8 | 69.8 |
| (3) Ethylparaben | 0.2 | 0.2 | 0.2 |
| Evaluation | | | |
| Stickiness of hand | ⊚ | — | Δ |
| Easiness of hand combing | | | |
| (Right after) | ⊚ | — | ○ |
| (After 6 hours) | ⊚ | — | — |
| Smoothness | | | |
| (Right after) | ⊚ | — | Δ |
| (After 6 hours) | ⊚ | — | Δ |
| Hair dressing power | | | |
| (Right after) | ⊚ | — | — |
| (After 6 hours) | ⊚ | — | — |
| (After 12 hours) | ⊚ | — | — |

<Manufacturing Process of Wax Part>

The ingredients (1) to (4) were stirred about 92° C. After the mixture had transparency, the mixture was cooled down with ice and a fine dispersion composition of wax was obtained.

<manufacturing Process of Emulsion Part>

The ingredients (1) to (4) and a part of the ingredient (5) were stirred and emulsified by a homomixer. Then, a emulsified composition was obtained by adding the rest of the ingredient (5).

<Manufacturing Process of Set Lotion>

A shake type set lotion was obtained by mixing the above-mentioned two compositions and the ingredient (3) in the ratio which is shown in TABLE 18.

As is clear from the results shown above, though Test Example 60 which did not compound wax could be obtained a little feel of use in view of less stickiness of hand, smoothness of hand combing and smoothness, it was largely inferior in hair dressing power as compared with Test Example 59. On the contrary, Test Example 58 which compounded the fine dispersion composition of wax of the present invention and the polyether compound that propylene oxide and/or ethylene oxide is additionally polymerized to nucleus of polyhydric alcohol was improved in all of the views such as less stickiness of hand, easiness of hand combing, smoothness, and hair dressing power. Also, it was appreciated that these effects were maintained even after 6 hours has passed. Further, it was appreciated that the improvement effect of hair dressing power was maintained for 12 hours.

A hair cosmetic preparation of the present invention is mixed the fine dispersion composition of wax with the emulsified composition which comprises the polyether compound that propylene oxide and/or ethylene oxide is additionally polymerized to nucleus of polyhydric alcohol that both are separately prepared.

Then, the composition which was almost same composition with Test Example 58 of the present invention and which was prepared without separating to the wax part and the emulsion part was determined as Test Example 61.

The difference between an oil-in-water hair cosmetic preparation of the present invention and Test Example 61 is explained in the following. Though an emulsion particle of the polyether compound that propylene oxide and/or ethylene oxide is additionally polymerized to nucleus of polyhydric alcohol and a dispersion particle of wax existed in separately in the present invention, both formed the same dispersion particle in the composition of Test Example 61.

| Test Example 61 | |
|---|---|
| (1) Carnauba wax | 4.5 |
| (2) Polyoxyethylene behenyl ether (10EO) | 3.0 |
| (3) Sodium 2-undecyl-N,N,N-(hydroxyethylcarboxymethyl)-2-imidazolinium betaine*[3] | 5.0 |
| (4) Pentaerythritol (PO) 65 mol (EO) 4.5 mol additions | 20.9 |
| (5) 1,3-butylene glycol | 3.5 |
| (6) Isostearic acid*[2] | 0.7 |
| (7) Ion-exchanged water | 55.3 |
| Evaluation: | |
| Stickiness of hand | Δ |
| Easiness of hand combing | Δ |
|  | (After 6 hours —, after 12 hours —) |

| Test Example 61 (continued) | |
|---|---|
| Smoothness | Δ |
|  | (After 6 hours —, after 12 hours —) |
| Hair dressing power | Δ |
|  | (After 6 hours —, after 12 hours —) |

<Manufacturing Process>

The ingredients (1) to (5) and a part of the ingredient (6) were mixed and stirred at 95° C. and a fine dispersion composition of wax which comprised pentaerythritol (PO) 65 mol (EO) 4.5 mol additions was obtained. Then, a set lotion was obtained by adding the rest of the ingredient (6).

As a result, it is apparent that an excellent feeling of use such as less stickiness of hand, easiness of hand combing, and smoothness can be obtained in the cases where a dispersion particle of wax and a particle of the polyether compound that propylene oxide and/or ethylene oxide is additionally polymerized to nucleus of polyhydric alcohol are existed in separately.

Compounding Amount of Polyether Compound that Propylene Oxide and/or Ethylene Oxide is Additionally Polymerized to Nucleus of Polyhydric Alcohol Next, the present inventors studied about a compounding amount of the polyether compound that propylene oxide and/or ethylene oxide is additionally polymerized to nucleus of polyhydric alcohol and a weight ratio of wax/the polyether compound that propylene oxide and/or ethylene oxide is additionally polymerized to nucleus of polyhydric alcohol by changing the compounding amount of the fine dispersion composition of wax (wax part) and the emulsified composition (emulsion part) which comprises the polyether compound that propylene oxide and/or ethylene oxide is additionally polymerized to nucleus of polyhydric alcohol (polyhydric alcohol PO/EO additions).

TABLE 20

| Set Lotion | Test ex. 62 | Test ex. 63 | Test ex. 64 | Test ex. 65 | Test ex. 66 | Test ex. 67 | Test ex. 68 |
|---|---|---|---|---|---|---|---|
| (Wax part) | | | | | | | |
| (1) Carnauba wax | 15.0 | 15.0 | 15.0 | 15.0 | 15.0 | 15.0 | 15.0 |
| (2) Polyoxyethylene behenyl ether (10EO) | 10.0 | 10.0 | 10.0 | 10.0 | 10.0 | 10.0 | 10.0 |
| (3) Cocoyl fatty acid amide dimethyl amino acetic acid betaine*[1] | 5.0 | 5.0 | 5.0 | 5.0 | 5.0 | 5.0 | 5.0 |
| (4) Ion-exchanged water | 70.0 | 70.0 | 70.0 | 70.0 | 70.0 | 70.0 | 70.0 |
| (1) Pentaerythritol(PO) 65 mol (EO) 4.5 mol additions | 50.0 | 50.0 | 50.0 | 50.0 | 50.0 | 50.0 | 50.0 |
| (2) 1,3-butylene glycol | 5.0 | 5.0 | 5.0 | 5.0 | 5.0 | 5.0 | 5.0 |
| (3) Isostearic acid*[2] | 1.0 | 1.0 | 1.0 | 1.0 | 1.0 | 1.0 | 1.0 |
| (4) Sodium 2-undecyl-N,N,N-(hydroxyethylcarboxymethyl)-2-imidazolinium betaine*[3] | 5.0 | 5.0 | 5.0 | 5.0 | 5.0 | 5.0 | 5.0 |
| (5) Ion-exchanged water | 59.0 | 59.0 | 59.0 | 59.0 | 59.0 | 59.0 | 59.0 |

TABLE 20-continued

| Set Lotion | Test ex. 62 | Test ex. 63 | Test ex. 64 | Test ex. 65 | Test ex. 66 | Test ex. 67 | Test ex. 68 |
|---|---|---|---|---|---|---|---|
| (Finished product) | | | | | | | |
| (1) Wax part | 99.0 | 97.0 | 70.0 | 60.0 | 50.0 | 40.0 | 30.0 |
| (part of wax) | (14.85) | (14.55) | (10.5) | (9.0) | (7.5) | (6.0) | (4.5) |
| (2) Emulsion part | 0.8 | 2.8 | 29.8 | 39.8 | 49.8 | 59.8 | 69.8 |
| (part of polyhydric alcohol PO/EO additions) | (0.4) | (1.4) | (14.9) | (19.9) | (24.9) | (29.9) | (34.9) |
| (3) Ethylparaben | 0.2 | 0.2 | 0.2 | 0.2 | 0.2 | 0.2 | 0.2 |
| Weight ratio of Wax/ (Polyhydric alcohol PO/EO additions) | 37.13 | 10.39 | 0.70 | 0.45 | 0.30 | 0.20 | 0.13 |
| Evaluation | | | | | | | |
| Stickiness of hand | Δ | ○ | ⊚ | ⊚ | ⊚ | ○ | Δ |
| Easiness of hand combing | Δ | ○ | ⊚ | ⊚ | ⊚ | ⊚ | ⊚ |
| Smoothness | Δ | ○ | ⊚ | ⊚ | ⊚ | ⊚ | ⊚ |
| Hair dressing power | | | | | | | |
| (Right after) | Δ | ○ | ⊚ | ⊚ | ⊚ | ⊚ | ⊚ |
| (After 6 hours) | Δ | ○ | ⊚ | ⊚ | ⊚ | ○ | Δ |
| (After 12 hours) | — | ○ | ⊚ | ⊚ | ⊚ | ○ | Δ |

As a results shown above, a preferable compounding amount of the polyether compound that propylene oxide and/or ethylene oxide is additionally polymerized to nucleus of polyhydric alcohol is about 1 to about 30 wt %.

Also, a preferable weight ratio of wax/(the polyether compound that propylene oxide and/or ethylene oxide is additionally polymerized to nucleus of polyhydric alcohol) is 0.2 to 10.

(F) Extracts from Vegetables

Next, a hair cosmetic preparation which compounds a fine dispersion composition of wax and an extracts extracted from vegetables is shown in the following.

Ingredient of the Present Invention

Test Example 69, Test Example 70, and Test Example 71 is the composition of the present invention, the composition which only comprised the fine dispersion composition of wax and the composition which only comprises an extracts from vegetables, respectively.

TABLE 21

| Set Lotion | Test Ex. 69 | Test Ex. 70 | Test Ex. 71 |
|---|---|---|---|
| (1) Carnauba wax | 15.0 | 15.0 | — |
| (2) Polyoxyethylene behenyl ether (10EO) | 10.0 | 10.0 | 10.0 |
| (3) )Sodium 2-undecyl-N,N,N-(hydroxy-ethylcarboxymethyl)-2-imidazolinium betaine*³ | 5.0 | 5.0 | 5.0 |
| (4) Ion-exchanged water | 67.8 | 69.8 | 82.8 |
| (5) Thyme extract | 1.0 | — | 1.0 |
| (6) Mallow extract | 1.0 | — | 1.0 |
| (7) Methylparaben | 0.2 | 0.2 | 0.2 |
| Evaluation | | | |
| Stickiness of hand | ⊚ | — | Δ |
| Easiness of hand combing | | | |
| (Right after) | ⊚ | — | ○ |
| (After 6 hours) | ⊚ | — | — |
| Smoothness | | | |
| (Right after) | ⊚ | — | Δ |
| (After 6 hours) | ⊚ | — | Δ |

TABLE 21-continued

| Set Lotion | Test Ex. 69 | Test Ex. 70 | Test Ex. 71 |
|---|---|---|---|
| Hair dressing power | | | |
| (Right after) | ⊚ | — | — |
| (After 6 hours) | ⊚ | — | — |

<Manufacturing Process of Test Example 69>

The ingredients (1) and a part of the ingredient (4) were mixed and stirred about 95° C. After the mixture had transparency, the mixture was cooled down with ice and a fine dispersion composition of wax was obtained. A set lotion was obtained by mixing the dissolution of the ingredients (5) to (7) with the rest of the ingredient (4).

<Manufacturing Process of Test Example 70>

The ingredients (1) to (3) and a part of the ingredient (4) were stirred about 95° C. After the mixture had transparency, the mixture was cooled down with ice and a fine dispersion composition of wax was obtained. A set lotion was obtained by mixing the dissolution of the ingredient (7) with the rest of the ingredient (4).

<Manufacturing Process of Test Example 71>

A set lotion was obtained by adding the ingredient (4) to the ingredients (2), (3) and (5) to (7).

As is clear from the results shown above, though Test Example 71 which did not compound wax could be obtained a little feel of use in view of less stickiness of hand, smoothness of hand combing and smoothness, it was largely inferior in hair dressing power as compared with Test Example 70. on the contrary, Test Example 69 which compounded the fine dispersion composition of wax of the present invention and the extracts extracted from vegetables was improved in all of the views such as less stickiness of hand, easiness of hand combing, smoothness, and hair dressing power. Also, it was appreciated that these effects were maintained even after 6 hours has passed. Also, Test Example 69 was also excellent in an activation effect of a scalp as compared with Test Example 71.

Compounding Amount of Wax/Extract from Vegetables

Next, the present inventors studied about a compounding amount of the extract from vegetables and a weight ratio of wax/extract from vegetables by changing the compounding amount of the extract from vegetables.

TABLE 22

| Set Lotion | Test ex. 72 | Test ex. 73 | Test ex. 74 | Test ex. 75 | Test ex. 76 | Test ex. 77 | Test ex. 78 |
|---|---|---|---|---|---|---|---|
| (1) Carnauba wax | 15.0 | 15.0 | 15.0 | 15.0 | 15.0 | 15.0 | 15.0 |
| (2) Polyoxyethylene behenyl ether (10EO) | 10.0 | 10.0 | 10.0 | 10.0 | 10.0 | 10.0 | 10.0 |
| (3) Cocoyl fatty acid amide dimethyl amino acetic acid betaine*1 | 5.0 | 5.0 | 5.0 | 5.0 | 5.0 | 5.0 | 5.0 |
| (4) Ion-exchanged water | 69.6999 | 69.699 | 69.69 | 68.7 | 68.2 | 64.7 | 63.7 |
| (5) Horsetail extract | 0.0001 | 0.001 | 0.01 | 1.0 | 1.5 | 5.0 | 6.0 |
| (6) Ethylparaben | 0.2 | 0.2 | 0.2 | 0.2 | 0.2 | 0.2 | 0.2 |
| (7) 2-phenoxy-ethanol | 0.1 | 0.1 | 0.1 | 0.1 | 0.1 | 0.1 | 0.1 |
| Weight ratio of Wax/(Extracts extracted from vegetables) | 150000 | 15000 | 1500 | 15 | 10 | 3 | 2.5 |
| Evaluation | | | | | | | |
| Stickiness of hand | Δ | ○ | ⊚ | ⊚ | ⊚ | ○ | Δ |
| Easiness of hand combing | Δ | ○ | ⊚ | ⊚ | ⊚ | ○ | Δ |
| Smoothness | Δ | ○ | ⊚ | ⊚ | ⊚ | ⊚ | ⊚ |
| Hair dressing power | Δ | ○ | ⊚ | ⊚ | ⊚ | ⊚ | ⊚ |

As a results shown above, a preferable compounding amount of the extracts extracted from vegetables is about 0.001 to about 5 wt %.

Also, a preferable weight ratio of wax/(extract from vegetables) is 3 to 15000.

<Working Example of Hair Cosmetic Preparation>

A working examples of a hair cosmetic preparation which comprises a fine dispersion composition of the present invention are shown in the following.

| Working Example 1   Set lotion | |
|---|---|
| (1) Carnauba wax | 3.0 |
| (2) Polyoxyethylene behenyl ether (10EO) | 3.0 |
| (3) Cocoyl amide dimethyl glycine (significant part 30%) (Trade name; Rebon 2000-SF, manufactured by Sanyo Chemical Industries Ltd.) | 4.95 |
| (4) Ion-exchanged water | 56.55 |
| (5) Ethyl alcohol | 30.0 |
| (6) Polyether denatured silicone (Trade name; Toray silicone SH 3771C, manufactured by Toray Dow Corning Silicone Co., Ltd.) | 0.5 |
| (7) Glycerin | 2.0 |
| (8) Paraben | q.s. |
| (9) Perfume | q.s. |

<Manufacturing Process>

The ingredients (1) to (3) and a part of the ingredient (4) were stirred and mixed at about 95° C. After the mixture had transparency, the mixture was cooled down with ice and a fine dispersion composition of wax was obtained. Then, a set lotion was obtained by adding the mixture of the rest of the ingredient (4) and the ingredients (5) to (9) to the fine dispersion composition of wax.

| Working Example 2   Hair mousse | |
|---|---|
| (1) Candelilla wax | 5.0 |
| (2) Microcrystalline wax | 1.0 |
| (3) Polyoxyethylene behenyl ether (20EO) | 4.0 |
| (4) Sodium 2-undecyl-N,N,N-(hydroxyethyl carboxymethyl)2-imidazolinium betaine (significant part 30%) (Trade name; Ovazoline 662N desalted, Toho chemical Industry Co., Ltd.) | 9.0 |
| (5) Ion-exchanged water | 54.0 |
| (6) Propylene glycol | 12.0 |
| (7) Ethyl alcohol | 5.0 |
| (8) UV-protecting agent | q.s. |
| (9) Perfume | q.s. |
| (10) Liquefied petroleum gas | 10.0 |

<Manufacturing Process>

The ingredients (1) to (4) and a part of the ingredient (5) were stirred and mixed at 95° C. After the mixture had transparency, the mixture was cooled down with ice and a fine dispersion composition of wax was obtained. Then, a hair mousse stock solution was obtained by adding the mixture of the rest of the ingredient (5) and the ingredients (6) to (9) to the fine dispersion composition of wax. After the hair mousse stock solution was added to an aerosol can and the aerosol can was capped, a hair mousse was obtained by filling liquefied petroleum gas as a propellant.

| Working Example 3   Set lotion | |
|---|---|
| (Wax part) | |
| (1) Carnauba wax | 10.0 |
| (2) Polyoxyethylene behenyl ether (10EO) | 10.0 |
| (3) Cocoyl amide dimethyl glycine (significant part 30%) (Trade name; Rebon 2000-SF, manufactured by Sanyo Chemical Industries Ltd.) | 15.0 |
| (4) Ion-exchanged water | 65.0 |

<Manufacturing Process of Wax Part>

The ingredients (1) to (4) were mixed and stirred at 95° C. After the mixture had transparency, a fine dispersion composition of wax was obtained by cooling down the mixture with ice.

| (Emulsion Part) | |
|---|---|
| (1) Squalane | 10.0 |
| (2) Liquid petrolatum | 10.0 |
| (3) Jojoba oil | 10.0 |
| (4) 1,3-butylene glycol | 5.0 |
| (5) Isostearic acid | 1.0 |
| (6) Sodium 2-undecyl-N,N,N-(hydroxyethyl carboxymethyl)-2-imidazolinium betaine (significant part 30%) (Trade name: Ovazoline 662N desalted, manufactured by Toho Chemical Industry Co., Ltd.) | 6.0 |
| (7) Ion-exchanged water | 48.0 |

<Manufacturing Process of Emulsion Part>

The ingredients (1) to (6) and a part of the ingredient (7) were stirred and emulsified with a homomixer. Then, an emulsified composition was obtained by adding the rest of the ingredient (7) to the emulsion.

<Manufacturing Process of Set Lotion>

A shake-type set lotion was obtained by mixing two compositions shown above and the ingredient (3) in the percentage shown in the following.

| | | |
|---|---|---|
| (1) Wax part | | 30.0 |
| (2) Emulsion part | | 69.8 |
| (3) Methylparaben | | 0.2 |

| Working Example 4  Styling Gel | | |
|---|---|---|
| (Wax part) | | |
| (1) Carnauba wax | | 6.0 |
| (2) Candelilla wax | | 4.0 |
| (3) Polyoxyethylene (15) Polyoxypropylene (2) behenyl ether | | 10.0 |
| (4) Lauryl dimethylamino acetic acid betaine (significant part 30%) (Trade name; Anon BL-SF, manufactured by NOF Corp.) | | 7.0 |
| (5) Ion-exchanged water | | 73.0 |

<Manufacturing Process of Wax Part>

The ingredients (1) to (5) were mixed and stirred at 95° C. After the mixture had transparency, a fine dispersion composition of wax was obtained by cooling down the mixture with ice.

| (Emulsion Part) | | |
|---|---|---|
| (1) Decamethylcyclo pentasiloxane | | 10.0 |
| (2) Dimethyl polysiloxane | | 4.0 |
| (3) Amino denatured polymerized silicone | | 1.0 |
| (4) 2-hexyldecyl isostearate | | 20.0 |
| (5) Propylene glycol | | 2.0 |
| (6) Polyoxyethylene hydrogenated castor oil (60EO) | | 6.0 |
| (7) Ion-exchanged water | | 57.0 |

<Manufacturing Process of Emulsion Part>

The ingredients (1) to (6) and a part of the ingredient (7) were stirred and emulsified with a homomixer. Then, an emulsified composition was obtained by adding the rest of the ingredient (7) to the emulsion.

<Manufacturing Process of Styling Gel>

A styling gel was obtained by mixing two compositions shown above and the ingredients (3) to (9) in the percentage shown in the following.

| | | |
|---|---|---|
| (1) Wax part | | 50.0 |
| (2) Emulsion part | | 10.0 |
| (3) Diglycerine | | 10.0 |
| (4) Carboxyvinylpolymer | | 0.7 |
| (5) Sodium hydroxide | | 0.2 |
| (6) Betaine dialkylaminoalkyl acrylate (Trade name ; Yukaformer AM75-SM, manufactured by Mitsubishi Chemical Company Ltd.) | | 3.0 |
| (7) Ethanol | | 2.0 |
| (8) Methylparaben | | 0.1 |
| (9) Ion-exchanged water | | 24.0 |

| Working Example 5  Styling mousse | | |
|---|---|---|
| (Wax part) | | |
| (1) Carnauba wax | | 9.0 |
| (2) Microcrystalline wax | | 1.0 |
| (3) Polyoxyethylene (10) polyoxypropylene (2) behenyl ether | | 7.0 |
| (4) )Sodium 2-undecyl-N,N,N-(hydroxyethyl carboxymethyl)-2-imidazolinium betaine (significant part 28%) (Trade name: Sofdazoline LHL desalted, manufactured by Kawaken Fine Chemicals Co., Ltd.) | | 10.0 |
| (5) Ion-exchanged water | | 73.0 |

<Manufacturing Process of Wax Part>

The ingredients (1) to (5) were mixed and stirred at 95° C. After the mixture had transparency, a fine dispersion composition of wax was obtained by cooling down the mixture with ice.

| (Emulsion Part) | | |
|---|---|---|
| (1) Isoparaffin | | 15.0 |
| (2) α-olefine oligomer | | 10.0 |
| (3) Isocetyl isostearate | | 3.0 |
| (4) Dimethylpolysiloxane (20cs) | | 8.0 |
| (5) Propylene glycol | | 2.0 |
| (6) Polyoxyethylene hydrogenated castor oil (60EO) | | 1.0 |
| (7) Oleic acid | | 1.0 |
| (8) Lauryl dimethylaminoacetic betaine (significant part 30%) (Trade name; Anon BL, manufactured by NOF Corp.) | | 6.0 |
| (9) Ion-exchanged water | | 54.0 |

<Manufacturing Process of Emulsion Part>

The ingredients (1) to (8) and a part of the ingredient (9) were stirred and emulsified with a homomixer. Then, an emulsified composition was obtained by adding the rest of the ingredient (9) to the emulsion.

<Manufacturing Process of Styling Mousse>

A hair mousse stock solution was obtained by mixing two compositions shown above and the ingredients (3) to (6) in the percentage shown in the following. After the hair mousse stock solution was added to an aerosol can and the aerosol can was capped, a hair mousse was obtained by filling the ingredient (7).

| | | |
|---|---|---|
| (1) Wax part | | 56.65 |
| (2) Emulsion part | | 20.0 |
| (3) Ethanol | | 3.0 |
| (4) Ethylparaben | | 0.15 |
| (5) 2-phenoxyethanol | | 0.2 |
| (6) Glycerin | | 10.0 |
| (7) Liquefied petroleum gas | | 10.0 |

| Working Example 6  Hair Gel | | |
|---|---|---|
| (1) Carnauba wax | | 5.0 |
| (2) Candelilla wax | | 5.0 |
| (3) Polyoxyethylene behenyl ether (15EO) | | 9.0 |
| (4) Lauryl dimethylaminoacetic acid betaine (significant part 30%) (Trade name; Anon BL, manufactured by NOF Corp.) | | 3.3 |
| (5) Ion-exchanged water | | 37.8 |

Working Example 6   Hair Gel (continued)

| | |
|---|---|
| (6) Carboxyvinylpolymer (Trade name ; Hibis Wako 104, manufactured by Wako Junyaku Co., Ltd.) | 0.7 |
| (7) Polyvinyl pyrrolidone vinyl acetate copolymer | 2.0 |
| (8) Glycerin | 5.0 |
| (9) Polyoxyethylene octyl dodecyl ether | q.s. |
| (10) Perfume | q.s. |
| (11) Chelating agent | q.s. |
| (12) Sodium hydroxide | q.s. |

<Manufacturing Process>

The ingredients (1) to (4) and a part of the ingredient (5) were emulsified by a high-pressure homogenizer under the conditions of 560 atm and 85° C. After the emulsion had transparency, the emulsion was cooled down with ice and a fine dispersion composition of wax was obtained. After the mixture of the rest of the ingredient (5) and the ingredients (6) to (11) were added to the fine dispersion composition of wax, a hair gel was obtained by adding the ingredient (12) to the fine dispersion composition.

Comparison with a Prior Art

A hair cosmetic preparations of Working Example 7 to 9 of the present invention and Comparative Examples 1 to 3 which were prepared for the purpose of conducting a general hair set of prior art and were not compounded wax were prepared.

Working Example 7   Set Lotion (Wax Part)

| | |
|---|---|
| (1) Carnauba wax | 15.0 |
| (2) Polyoxyethylene behenyl ether (10EO) | 10.0 |
| (3) Cocoyl dimethylamino glycine (significant part 30%) (Trade name : Rebon 2000-SF, manufactured by Sanyo Chemical Industries Co., Ltd.) | 5.0 |
| (4) Ion-exchanged water | 70.0 |

<Manufacturing Process of Wax Part>

The ingredients (1) to (4) were mixed and stirred at 95° C. After the mixture had transparency, a fine dispersion composition of wax as obtained by cooling down the mixture with ice.

(Emulsion Part)

| | |
|---|---|
| (1) Liquid paraffin | 30.0 |
| (2) Jojoba oil | 10.0 |
| (3) 1,3-butylene glycol | 5.0 |
| (4) Isostearic acid | 1.0 |
| (5) Sodium 2-undecyl-N,N,N-(hydroxyethyl carboxymethyl)-2-imidazolinium betaine (active ingredient 30%) (Trade name: Ovazoline 662N desalted, manufactured by Toho Chemical Industry Co., Ltd.) | 5.0 |
| (6) Ion-exchanged water | 49.0 |

<Manufacturing Process of Emulsion Part>

The ingredients (1) to (5) and a part of the ingredient (6) were stirred and emulsified with a homomixer. Then, an emulsified composition was obtained by adding the rest of the ingredient (6) to the emulsion.

<Manufacturing Process of Set Lotion>

A shake-type set lotion was obtained by mixing two compositions shown above and the ingredient (3) in the percentage shown in the following.

| | |
|---|---|
| (1) Emulsion part | 69.8 |
| (2) Wax part | 30.0 |
| (3) Methylparaben | 0.2 |

Working example 8   Styling Mousse (Wax Part)

| | |
|---|---|
| (1) Candelilla wax | 10.0 |
| (2) Polyoxyethylene behenyl ether (20EO) | 8.0 |
| (3) Sodium 2-undecyl-N,N,N-(hydroxyethyl carboxymethyl)-2-imidazolinium betaine (significant part 30%) (Trade name: Ovazoline 662N desalted, manufactured by Toho Chemical Industry Co., Ltd.) | 4.0 |
| (4) Ion-exchanged water | 78.0 |

<Manufacturing Process of Wax Parts>

The ingredients (1) to (4) were mixed and stirred at 95° C. After the mixture had transparency, a fine dispersion composition of wax was obtained by cooling down the mixture with ice.

(Emulsion Part)

| | |
|---|---|
| (1) Isoparaffin | 15.0 |
| (2) α-olefine oligomer | 10.0 |
| (3) Octyl palmitate | 5.0 |
| (4) Propylene glycol | 3.0 |
| (5) Dimethyl polysiloxane 20cs | 10.0 |
| (6) Polyoxyethylene hydrogenated castor oil (60EO) | 1.0 |
| (7) Oleic acid | 1.0 |
| (8) Lauryl dimetylacetic acid betaine (significant part 30%) (Trade name; Anon BL, manufactured by NOF Corp.) | 7.0 |
| (9) Ion-exchanged water | 38.0 |

<Manufacturing Process of Emulsion Part>

The ingredients (1) to (8) and a part of the ingredient (9) were stirred and emulsified by a homomixer. Then, an emulsified composition was obtained by adding the rest of the ingredient (9) to the emulsion.

<Manufacturing Process of Styling Mousse>

A styling mousse stock was prepared by mixing two compositions shown above and the ingredients (3) to (6) in the percentage shown in the following. After filling the mousse stock into an aerosol can and fitting a valve, a styling mousse was obtained by filling the ingredient (7).

| | |
|---|---|
| (1) Wax part | 56.65 |
| (2) Emulsion part | 20.0 |
| (3) Ethanol | 3.0 |
| (4) Ethylparaben | 0.15 |
| (5) 2-phenoxyethanol | 0.2 |
| (6) Glycerin | 10.0 |
| (7) Liquefied petroleum gas (LPG) | 10.0 |

| Working Example 9 Styling Gel | |
|---|---|
| (Wax Part) | |
| (1) Microcrystalline wax | 10.0 |
| (2) Polyoxyethylene behenyl ether (10EO) | 6.0 |
| (3) Sodium 2-undecyl-N,N-(hydroxyethyl carboxymethyl)-2-imidazolinium betaine (significant part 28%) (Trade name: Sofdazoline LHL desalted, manufactured by Kawaken Fine Chemicals Co., Ltd.) | 9.0 |
| (4) Ion-exchanged water | 79.0 |

<Manufacturing Process of Wax Part>

The ingredients (1) to (4) were mixed and stirred at 95° C. After the mixture had transparency, a fine dispersion composition of wax as obtained by cooling down the mixture with ice.

| (Emulsion Part) | |
|---|---|
| (1) Decamethylcyclopentasiloxane | 15.0 |
| (2) Amino denatured polymerized silicone | 1.0 |
| (3) 2-hexyl decyl isostearate | 20.0 |
| (4) Propylene glycol | 2.0 |
| (5) Polyoxyethylene hydrogenated castor oil (40EO) | 5.0 |
| (6) Ion-exchanged water | 57.0 |

<Manufacturing Process of Emulsion Part>

The ingredients (1) to (5) and a part of the ingredient (6) were stirred and emulsified by a homomixer. Then, an emulsified composition was obtained by adding the rest of the ingredient (6) to the emulsion.

<Manufacturing Process of Styling Gel>

A styling gel was obtained by mixing two compositions shown above and the ingredients (3) to (6) in the percentage shown in the following.

| | |
|---|---|
| (1) Wax part | 50.0 |
| (2) Emulsion part | 10.0 |
| (3) Diglycerine | 10.0 |
| (4) Carboxyvinylpolymer | 0.7 |
| (5) Sodium hydroxide | 0.2 |
| (6) Betaine dialkylaminoaryrate (Trade name; Yukaformer AM75-SM, manufactured by Mitsubishi Chemical Company Ltd.) | 3.0 |
| (7) Ethanol | 2.0 |
| (8) Methylparaben | 0.1 |
| (9) Ion-exchanged water | 24.0 |

| Comparative Example 1. Set Lotion | |
|---|---|
| (1) Polyvinylpyrrolidone/vinyl acetate copolymer | 5.0 |
| (2) Methylparaben | q.s. |
| (3) Perfume | q.s. |
| (4) Ethanol | 30.0 |
| (5) Ion-exchanged water | 62.5 |
| (6) Silicone derivative | 0.5 |
| (7) Glycerin | 2.0 |

<Manufacturing Process of Set Lotion>

The ingredients (1) to (3) were added and dissolved to the ingredient (4). A water phase which was previously dissolved (a mixture of the ingredients (5) to (7)) was added and dissolved to the mixture.

| Comparative Example 2. Styling Mousse | |
|---|---|
| (1) Acrylic resin alkanolamine solution (50%) | 8.0 |
| (2) Polyoxyethylene hydrogenated castor oil (60EO) | q.s. |
| (3) Liquid petrolatum | 5.0 |
| (4) Glycerin | 3.0 |
| (5) Perfume | q.s. |
| (6) Methylparaben | q.s. |
| (7) Ion-exchanged water | 60.0 |
| (8) Ethanol | 15.0 |
| (9) Liquefied petroleum gas | 9.0 |

<Manufacturing Process of Styling Mousse>

The ingredient (3) was added to the dissolution of the ingredients (2) and (4) and uniformly emulsified by a homomixer. A hair mousse stock solution was obtained by adding the emulsion with the solution of the other ingredients excluding the ingredient (9). After filling the mouse stock solution into an aerosol can and fitting a valve, a styling mousse was obtained by filling the ingredient (9).

| Comparative Example 3. Styling Gel | |
|---|---|
| (1) Carboxyvinylpolymer | 0.7% |
| (2) Polyvinylpyrrolidone | 2.0 |
| (3) Glycerine | q.s. |
| (4) Ethanol | 20.0 |
| (5) Polyoxyethylene octyl dodecyl ether | q.s. |
| (6) Perfume | q.s. |
| (7) Chelating agent | q.s. |
| (8) Ion-exchanged water | 77.3 |

<Manufacturing Process of Styling Gel>

The ingredients (1) to (3) were dispersed in a part of the ingredient (8). The other ingredients were dissolved in the rest of the ingredient (8) and the dissolution was added to the mixture of the ingredients (1), (3) and (8) which was stirring.

Thus obtained products of Working Examples and Comparative Examples were used as a sample. These samples were evaluated with respect to <stickiness of hand>, <easiness of hand combing>, <smoothness>, and <hair dressing power>, Evaluation method is the same method as described above.

These results are shown in the following.

TABLE 23

| | Stickiness of hand | Easiness of hand combing | Smoothness | Hair dressing power |
|---|---|---|---|---|
| Working Ex. 7 | | | | |
| Right after | ◉ | ◎ | ◎ | ◎ |
| After 6 hrs. | | ◎ | ◎ | ◎ |
| Working Ex. 8 | | | | |
| Right after | ○ | ◎ | ◎ | ◎ |
| After 6 hrs. | | ◎ | ◎ | ◎ |
| Working Ex. 9 | | | | |
| Right after | ○ | ◎ | ◎ | ◎ |
| After 6 hrs. | | ◎ | ◎ | ◎ |

TABLE 23-continued

|  | Stickiness of hand | Easiness of hand combing | Smoothness | Hair dressing power |
|---|---|---|---|---|
| Comp. Ex. 1 | | | | |
| Right after | ○ | Δ | Δ | — |
| After 6 hrs. | — | — | — | |
| Comp. Ex. 2 | | | | |
| Right after | Δ | ○ | — | — |
| After 6 hrs. | | Δ | — | — |
| Comp. Ex. 3 | | | | |
| Right after | Δ | Δ | Δ | — |
| After 6 hrs. | — | — | — | |

As a result, a hair cosmetic preparation of Working Examples 7 to 9 which compounded a fine dispersion composition of wax and a hydrocarbon oil and/or an ester oil were improved in all the views of stickiness of hand, easiness of hand combing, smoothness, and hair dressing power.

On the other hand, the compositions of Comparative Examples 1 to 3 which were not compounded wax were inferior in hair dressing power as compared with the hair cosmetic preparation of the present invention.

| Working Example 10  Set lotion | |
|---|---|
| (1) Carnauba wax | 3.0 |
| (2) Polyoxyethylene behenyl ether (10EO) | 3.0 |
| (3) Cocoyl amide dimethyl glycine (significant part 30%) (Trade name; Rebon 2000-SF, manufactured by Sanyo Chemical Industries Ltd.) | 4.95 |
| (4) Ion-exchanged water | 83.75 |
| (5) Soybean lecithin | 1.0 |
| (6) Elastin | 1.0 |
| (7) Glycerin | 2.0 |
| (8) Methylparaben | 0.3 |
| (9) Perfume | q.s. |
| (10) Ethyl alcohol | 1.0 |

<Manufacturing Process of Set Lotion>

The ingredients (1) to (3) and a part of the ingredient (4) were stirred and mixed at about 95° C. After the mixture had transparency, the mixture was cooled down with ice and a fine dispersion composition of wax was obtained. Then, a set lotion was obtained by adding the mixture of the rest of the ingredient (4) and the ingredients (5) to (8) to the fine dispersion composition of wax.

| Working Example 11  Styling mousse | |
|---|---|
| (1) Candelilla wax | 5.0 |
| (2) Microcrystalline wax | 1.0 |
| (3) Polyoxyethylene behenyl ether (10EO) | 4.0 |
| (4) Sodium 2-undecyl-N,N,N-(hydroxyethyl carboxymethyl)2-imidazolinium betaine (significant part 30%) (Trade name; Ovazoline 662N desalted, Toho chemical Industry Co., Ltd.) | 9.0 |
| (5) Ion-exchanged water | 53.6 |
| (6) Propylene glycol | 12.0 |
| (7) Keratin decomposition derivative of (I) of Synthesizing Example 3 | 0.1 |

| -continued | |
|---|---|
| Working Example 11  Styling mousse | |
| (8) Keratin decomposition derivative of (II) of Synthesizing Example 3 | 0.1 |
| (9) Collagen hydrolyzate | 0.1 |
| (10) Silylated peptide (Trade name; Promois W-52SIG, manufactured by Seiwa Kasei Co., Ltd.) | 0.1 |
| (11) Ethyl alcohol | 5.0 |
| (12) UV-protecting agent(oxybenzone) | q.s. |
| (13) Perfume | q.s. |
| (14) Liquefied petroleum gas | 10.0 |

<Manufacturing Process>

The ingredients (1) to (4) and a part of the ingredient (5) were stirred and mixed at 95° C. After the mixture had transparency, the mixture was cooled down with ice and a fine dispersion composition of wax was obtained. Then, a styling mousse stock solution was obtained by adding the mixture of the rest of the ingredient (5) and the ingredients (6) to (10) to the fine dispersion of wax. After the styling mousse stock solution was added to an aerosol can and the aerosol can was capped, a styling hair mousse was obtained by filling liquefied petroleum gas as a propellant.

| Working Example 12  Styling Gel | |
|---|---|
| (1) Carnauba wax | 5.0 |
| (2) Candelilla wax | 5.0 |
| (3) Polyoxyethylene behenyl ether (10EO) | 10.0 |
| (4) Lauryl dimetylacetic acid betaine (significant part 30%) (Trade name; Anon BL, manufactured by NOF Corp.) | 14.5 |
| (5) Ion-exchanged water | 54.78 |
| (6) Silylated peptide of Synthesizing Example 4 | 0.01 |
| (7) Silylated peptide of Synthesizing Example 6 | 0.01 |
| (8) Carboxyvinylpolymer (Trade name; Hibis wako 104, manufactured by Wako Junyaku Co., Ltd.) | 0.7 |
| (9) Polyvinylpyrrolidone/vinylacetate copolymer | 2.0 |
| (10) Diglycerine | 5.0 |
| (11) Polyoxyethylene octyl dodecyl ether | q.s. |
| (12) Perfume | q.s. |
| (13) Chelating agent | q.s. |
| (14) Sodium hydroxide | q.s. |
| (15) Ethanol | 3.0 |

<Manufacturing Process>

The ingredients (1) to (4) and a part of the ingredient (5) were stirred and mixed at 95° C. After the mixture had transparency, a fine dispersion composition of wax was obtained by mixing with ice. Then, a styling gel was obtained by adding the rest of the ingredient (5) to the mixture of the ingredients (6) to (12).

| Working Example 13  Set Lotion | |
|---|---|
| (Wax Part) | |
| (1) Carnauba wax | 15.0 |
| (2) Polyoxyethylene behenyl ether (10EO) | 10.0 |
| (3) Cocoyl diethylamine glycine (significant part 30%) (Trade name : Rebon 2000-SF, manufactured by Sanyo Chemical Industries Co., Ltd.) | 5.0 |
| (4) Ion-exchanged water | 54.8 |

<Manufacturing Process of Wax Part>

The ingredients (1) to (4) were mixed and stirred at 95° C. After the mixture had transparency, a fine dispersion composition of wax as obtained by cooling down the mixture with ice.

| (Emulsion Part) | |
| --- | --- |
| (1) Mannitol (PO) 20 mol (EO) 2 mol addition | 30.0 |
| (2) Polyglycerin (average molecular weight 350) (PO) 80 mol (EO) 10 mol addition | 10.0 |
| (3) 1,3-butylene glycol | 5.0 |
| (4) Isostearic acid | 1.0 |
| (5) Sodium 2-undecyl-N,N,N-(hydroxyethyl carboxymethyl)-2-imidazolinium betaine (active ingredient 30%) (Trade name: Ovazoline 662N desalted, manufactured by Toho Chemical Industry Co., Ltd.) | 5.0 |
| (6) Ion-exchanged water | 49.0 |

<Manufacturing Process of Emulsion Part>

The ingredients (1) to (6) and a part of the ingredient (7) were stirred and emulsified with a homomixer. Then, an emulsion composition was obtained by adding the rest of the ingredient (7) to the emulsion.

<Manufacturing Process of Set Lotion>

A shake-type set lotion was obtained by mixing two compositions shown above and the ingredient (3) in the percentage shown in the following.

| | |
| --- | --- |
| (1) Emulsion part | 69.8 |
| (2) Wax part | 30.0 |
| (3) Methylparaben | 0.2 |

| Working Example 14   Styling Mousse | |
| --- | --- |
| (1) Candelilla wax | 5.0 |
| (2) Microcrystalline wax | 1.0 |
| (3) Polyoxyethylene behenyl ether | 4.0 |
| (4) Sodium 2-undecyl-N,N,N-(hydroxyethyl carboxymethyl)-2-imidazolinium betaine (significant part 30%) (Trade name: Ovazoline 662N desalted, manufactured by Toho Chemical Industry Co., Ltd.) | 9.0 |
| (5) Ion-exchanged water | 53.6 |
| (6) Propylene glycol | 12.0 |
| (7) Hypericum extract | 0.1 |
| (8) Chlorella extract | 0.1 |
| (9) Collagen hydrolyzate | 0.1 |
| (10) Silylated peptide (Trade name; Promois W-52SIG, manufactured by Seiwa Kasei Co., Ltd.) | 0.1 |
| (11) Ethyl alcohol | 5.0 |
| (12) UV-protecting agent (oxybenzone) | q.s. |
| (13) Perfume | q.s. |
| (14) Liquefied petroleum gas | 10.0 |

<Manufacturing Process>

The ingredients (1) to (4) and a part of the ingredient (5) were stirred and mixed at 95° C. After the mixture had transparency, the mixture was cooled down with ice and a fine dispersion composition of wax as obtained. Then, the mixture of the rest of the ingredient (5) and the ingredients (6) to (10) were added to the fine dispersion composition of wax. A styling mousse stock solution was obtained by adding the mixture of the ingredients (11) to (13) to the mixture. After the styling mousse stock solution was added to an aerosol can and the aerosol can was capped, a styling mousse was obtained by filling liquefied petroleum gas as a propellant.

| Working Example 15   Glazing Agent | |
| --- | --- |
| (1) Carnauba wax | 5.0% |
| (2) Candelilla wax | 4.0 |
| (3) Microcrystalline wax | 2.0 |
| (4) Polyoxyethylene arachyl ether (10EO) | 9.0 |
| (5) Polyoxyethylene behenyl ether (20EO) | 1.0 |
| (6) Lauryl dimethylaminoacetic acid betaine (significant part 30%) (Trade name; Anon BL, manufactured by NOF Corp.) | 9.0 |
| (7) Dimethylpolysiloxane | 2.0 |
| (8) Isoparaffin | 2.0 |
| (9) Oleic acid | 0.4 |
| (10) Ion-exchanged water | Balance |

<Manufacturing Process>

The ingredients (1) to (5) and a part of the ingredients (6) and (10) were stirred and mixed at 95° C. After the mixture had transparency, a fine dispersion composition of wax was obtained by cooling the mixture with ice. Then, a glazing agent was obtained by adding an emulsion which was obtained by mixing the rest of the ingredients (6) and (10) and the ingredients (7) to (9) to the fine dispersion composition.

| Working Example 16   Car Wax | |
| --- | --- |
| (1) Carnauba wax | 8.0% |
| (2) Paraffin wax | 2.0 |
| (3) Polyoxyethylene (10) polyoxypropylene (2) behenyl ether | 1.0 |
| (4) Polyoxyethylene (20) polyoxypropylene (1) behenyl ether | 20.0 |
| (5) Lauryl dimethylaminoacetic acid betaine (significant part 30%) (Trade name; Anon BL, manufactured by NOF Corp.) | 10.0 |
| (6) Dimethylpolysiloxane (20cs) | 3.0 |
| (7) Isostearic acid | 0.5 |
| (8) Ion-exchanged water | Balance |

<Manufacturing Process>

The ingredients (1) to (4) and a part of the ingredients (5) and (8) were stirred and mixed at 95° C. After the mixture had transparency, a fine dispersion composition of wax was obtained by cooling the mixture with ice. Then, a car wax was obtained by adding an emulsion which was obtained by mixing the rest of the ingredients (5) and (8) and the ingredients (6) and (7) to the fine dispersion composition.

As explained above, according to a fine dispersion composition of wax in accordance with the present invention, an extremely fine particle of wax can be prepared by using nonionic surfactant with amphoteric surfactant and/or semipolar surfactant.

Also, since a hair cosmetic preparation in accordance with the present invention comprises a particle of wax which is comprised in said fine dispersion composition of wax and is solid or semisolid in ordinary temperature and one or more of the specific active ingredients, the hair cosmetic preparation is not only excellent in hair dressing power, but also is excellent in the feel of use such as smoothness, less stickiness, and easiness of hand combing.

Also, a fine dispersion composition of the present invention is excellent as a glazing agent.

What is claimed is:

1. A composition of wax comprising:
   an amphoteric surfactant and optionally a semi-polar surfactant;
   a nonionic surfactant; and
   a wax;
   wherein said composition is in a transparent liquid phase which is characterized by having a weighted average HLB of 6 to 15 for the total nonionic surfactant, a weight ratio of amphoteric surfactant/(amphoteric surfactant+nonionic surfactant) of 0.03 to 0.5; and
   wherein said nonionic surfactant is a polyoxyethylene polyoxypropylene alkyl ether having the formula of:

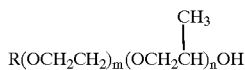

and optionally the following formula:

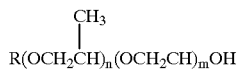

wherein R is an alkyl group of an alkyl group having a carbon number from 12 to 24, m is in the range of $5 \leq m \leq 30$, and n is in the range of $0 \leq n \leq 5$.

2. A composition of wax according to claim 1, wherein a weighted average HLB of total nonionic surfactant is 12 to 15 and the weight ratio of amphoteric surfactant/(amphoteric+nonionic surfactant) is 0.04 to 0.17.

3. A composition of wax according to claim 1, wherein a weighted average HLB of the total nonionic surfactant is 5 to 15 which is calculated by the formula:

$$HLB = 7 + 11.7 \log \frac{Mw}{Mo}$$

wherein Mw is molecular weight of hydrophilic group portion of said nonionic surfactant, and Mo is molecular weight of lipophilic group portion of said nonionic surfactant.

4. A composition of wax as in claim 1, wherein a weight ratio of amphoteric surfactant/(amphoteric surfactant+nonionic surfactant) is 0.03 to 0.5.

5. A composition of wax according to claim 1, wherein said wax is an oily component which is solid or semisolid in room temperature.

6. A composition of wax as in claim 1, wherein said transparent liquid phase of said composition is obtained by cooling said composition down to room temperature after heating said composition with temperature higher than the melting point of said wax and within a solubilization critical temperature of said wax.

7. A composition of wax as in claim 1, wherein said composition was prepared by using an emulsifier with shearing force over 400 atm and temperature higher than the melting point of said wax.

8. A hair cosmetic preparation comprising a composition of wax as in claim 1.

9. A hair cosmetic preparation according to claim 8, wherein said composition of wax are mixed with an emulsified composition comprising an oily particle having one or more of an hydrocarbon oil and optionally an ester oil, said composition of wax and said oily particle being separately existed in water.

10. A hair cosmetic preparation according to claim 9, wherein said hydrocarbon oil and optionally said ester oil is liquid in room temperature.

11. A hair cosmetic preparation according to claim 9, wherein said hydrocarbon oil and optionally said ester oil accounts for 1 to 50 wt %.

12. A process for preparing said hair cosmetic according to claim 9 comprising:
    mixing said composition of wax and said emulsified composition comprising said hydrocarbon oil and optionally said ester oil,
    wherein said composition of wax and said emulsified composition are separately prepared.

13. A process for preparing said hair cosmetic according to claim 9, wherein said emulsified composition comprises a complex which is obtained by mixing an amphoteric surfactant and optionally a semi-polar surfactant and a fatty acid selected from the group consisting of myristic acid, palmitic acid, stearic acid, behenic acid, oleic acid, 12-hydroxystearic acid, undecylenic acid, tall oil, isostearic acid, linoleic acid, linolenic acid, eicosapentaenoic acid, and docosahexaenoic acid.

14. A glazing agent comprising a composition of wax as in claim 1.

15. A composition of wax according to claim 1, wherein said composition comprises particles with diameters about 30 nm.

16. A composition of wax according to claim 1, wherein a weighted average HLB of the total nonionic surfactant is 9 and a weight ratio of amphoteric surfactant/(amphoteric+nonionic surfactant) is 0.23 to 0.40.

17. A composition of wax according to claim 1, wherein a weighted average HLB of the total nonionic surfactant is 13 and a weight ratio of amphoteric surfactant/(amphoteric+nonionic surfactant) is 0.04 to 0.17.

18. A composition of wax according to claim 1, wherein a weighted average HLB of the total nonionic surfactant is 12 and a weight ratio of amphoteric surfactant/(amphoteric+nonionic surfactant) is 0.07 to 0.18.

19. A composition of wax according to claim 1, wherein a weighted average HLB of the total nonionic surfactant is 15 and a weight ratio of amphoteric surfactant/(amphoteric+nonionic surfactant) is 0.03 to 0.5.

20. A composition of wax according to claim 3, wherein a weighted average HLB of the total nonionic surfactant is 8 and a weight ratio of amphoteric surfactant/(amphoteric+nonionic surfactant) is 0.21 to 0.38.

21. A composition of wax according to claim 3, wherein a weighted average HLB of the total nonionic surfactant is 6 and a weight ratio of amphoteric surfactant/(amphoteric+nonionic surfactant) is 0.32 to 0.45.

22. A composition of wax according to claim 3, wherein a weighted average HLB of the total nonionic surfactant is 10 and a weight ratio of amphoteric surfactant/(amphoteric+nonionic surfactant) is 0.08 to 0.20.

23. A composition of wax according to claim 3, wherein a weighted average HLB of the total nonionic surfactant is 12 and a weight ratio of amphoteric surfactant/(amphoteric+nonionic surfactant) is 0.03 to 0.16.

24. A composition of wax according to claim 3, wherein a weighted average HLB of the total nonionic surfactant is 14 and a weight ratio of amphoteric surfactant/(amphoteric+nonionic surfactant) is 0.03 to 0.5.

* * * * *